(12) United States Patent
Cheng et al.

(10) Patent No.: US 7,928,133 B2
(45) Date of Patent: Apr. 19, 2011

(54) COMPOUNDS AND COMPOSITIONS AS HEDGEHOG SIGNALING PATHWAY MODULATORS

(75) Inventors: Dai Cheng, San Diego, CA (US); Dong Han, San Diego, CA (US); Wenqi Gao, San Diego, CA (US); Jiqing Jiang, San Diego, CA (US); Shifeng Pan, San Diego, CA (US); Yongqin Wan, Irvine, CA (US); Qihui Jin, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 12/374,739

(22) PCT Filed: Jul. 24, 2007

(86) PCT No.: PCT/US2007/074268
§ 371 (c)(1),
(2), (4) Date: Aug. 17, 2009

(87) PCT Pub. No.: WO2008/014291
PCT Pub. Date: Jan. 31, 2008

(65) Prior Publication Data
US 2009/0312308 A1    Dec. 17, 2009

Related U.S. Application Data

(60) Provisional application No. 60/833,318, filed on Jul. 25, 2006, provisional application No. 60/942,650, filed on Jun. 7, 2007.

(51) Int. Cl.
| | |
|---|---|
| A61K 31/55 | (2006.01) |
| A61K 31/541 | (2006.01) |
| A61K 31/5377 | (2006.01) |
| A61K 31/517 | (2006.01) |
| A61K 31/4709 | (2006.01) |
| A61K 31/454 | (2006.01) |
| A61K 31/4439 | (2006.01) |
| A61K 31/4375 | (2006.01) |
| A61K 31/428 | (2006.01) |
| A61K 31/427 | (2006.01) |
| A61K 31/423 | (2006.01) |
| A61K 31/422 | (2006.01) |
| A61K 31/4178 | (2006.01) |
| A61K 31/4164 | (2006.01) |
| C07D 471/04 | (2006.01) |
| C07D 417/14 | (2006.01) |
| C07D 413/14 | (2006.01) |
| C07D 413/12 | (2006.01) |
| C07D 405/12 | (2006.01) |
| C07D 401/12 | (2006.01) |
| C07D 403/12 | (2006.01) |
| C07D 401/14 | (2006.01) |
| C07D 233/64 | (2006.01) |

(52) U.S. Cl. .................. 514/400; 514/234.5; 514/235.2; 514/323; 514/217.07; 514/238.8; 514/235.5; 514/313; 514/318; 514/341; 514/314; 514/233.8; 514/340; 514/234.8; 514/228.2; 540/597; 544/128; 544/127; 544/139; 544/131; 544/124; 544/119; 544/137; 544/135; 544/133; 544/58.6; 546/159; 546/160; 546/194; 546/275.1; 546/169; 548/338.1

(58) Field of Classification Search .................. 514/400, 514/234.5, 235.2, 323, 217.07, 238.8, 235.5, 514/313, 318, 341, 314, 233.8, 340, 234.8, 514/228.2; 540/597; 544/128, 127, 139, 544/131, 124, 119, 137, 135, 133, 58.6; 546/159, 546/160, 194, 275.1, 169; 548/338.1
See application file for complete search history.

(56) References Cited

U.S. PATENT DOCUMENTS
6,444,687 B1 * 9/2002 Stamford et al. ............. 514/318
2008/0161345 A1 * 7/2008 Ungashe et al. ............. 514/307

FOREIGN PATENT DOCUMENTS
| WO | WO0144201 A1 | 6/2001 |
| WO | WO2004091610 A1 | 10/2004 |
| WO | WO2006/050351 A2 | 5/2006 |

* cited by examiner

*Primary Examiner* — Joseph R Kosack
*Assistant Examiner* — Matthew P Coughlin
(74) *Attorney, Agent, or Firm* — Scott W. Reid; Genomics Institute of the Novartis Research Foundation

(57) ABSTRACT

The invention provides a method for modulating the activity of the hedgehog signaling pathway. In particular, the invention provides a method for inhibiting aberrant growth states resulting from phenotypes such as Ptc loss-of-function, hedgehog gain-of-function, smoothened gain-of-function or Gli gain-of-function, comprising contacting a cell with a sufficient amount of a compound of Formula I.

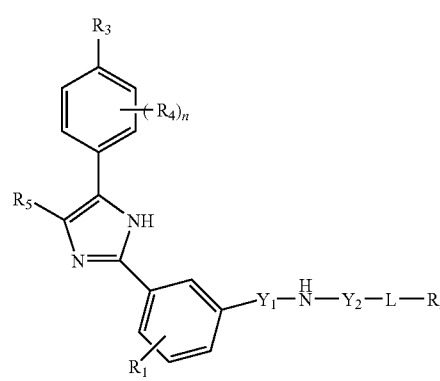

(I)

6 Claims, No Drawings

COMPOUNDS AND COMPOSITIONS AS HEDGEHOG SIGNALING PATHWAY MODULATORS

CROSS-REFERENCE TO RELATED APPLICATIONS

This application is a 371 U.S. national phase application of international application number PCT/US2007/074268 filed 24 Jul. 2007, which application claims priority to U.S. provisional patent application No. 60/833,318, filed 25 Jul. 2006 and U.S. provisional patent application No. 60/942,650 filed 7 Jun. 2007. The full disclosure of these applications is incorporated herein by reference in its entirety and for all purposes.

BACKGROUND OF THE INVENTION

1. Field of the Invention

The invention provides a method for modulating the activity of the hedgehog signaling pathway. In particular, the invention provides a method for inhibiting aberrant growth states resulting from phenotypes such as Ptc loss-of-function, hedgehog gain-of-function, smoothened gain-of-function or Gli gain-of-function, comprising contacting a cell with a sufficient amount of a compound of Formula I.

2. Background of the Invention

During embryonic development, the hedgehog signaling pathway is essential for numerous processes such as the control of cell proliferation, differentiation and tissue patterning. The aberrant activity of the hedgehog signaling pathway, for example, as a result of enhanced activation, however may have pathological consequences. In this regard, activation of the hedgehog pathway in adult tissues can result in diseases such as psoriasis and specific types of cancer that include, but are not limited to, malignant lymphoma (LM), multiple myeloma (MM), cancers of the brain, muscle and skin, prostrate, medulloblastoma, pancreatic adenocarcinomas and small-cell lung carcinomas. Enhanced activation of the hedgehog signaling pathway contributes to the pathology and/or symptomology of a number of diseases. Accordingly, molecules that modulate the activity of the hedgehog signaling pathway are useful as therapeutic agents in the treatment of such diseases.

SUMMARY OF THE INVENTION

In one aspect, the present invention provides compounds of Formula I:

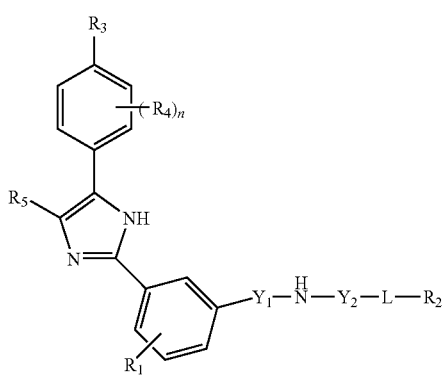

in which:
n is selected from 0, 1 and 2;
$Y_1$ is selected from a bond and C(O);
$Y_2$ is selected from a bond, C(O) and $S(O)_2$;
$R_1$ is selected from hydrogen, halo, cyano, $C_{1-2}$alkyl and halo-substituted-$C_{1-2}$alkyl;
$R_2$ is selected from hydrogen, halo, cyano, $C_{1-3}$alkyl, $C_{1-3}$alkoxy, halo-substituted-$C_{1-3}$alkyl, halo-substituted-$C_{1-3}$alkoxy, $C_{6-10}$aryl-$C_{0-4}$alkyl, $C_{1-10}$heteroaryl-$C_{0-4}$alkyl, $C_{3-12}$cycloalkyl-$C_{0-4}$alkyl, $C_{3-8}$heterocycloalkyl-$C_{0-4}$alkyl and phenoxy;
wherein said aryl, heteroaryl, cycloalkyl, heterocycloalkyl or phenoxy of $R_2$ can be optionally substituted with 1 to 3 radicals independently selected from $C_{1-6}$alkyl, halo-substituted-$C_{1-6}$alkyl, $C_{1-6}$alkoxy, halo-substituted-$C_{1-6}$alkoxy, $C_{6-10}$aryl-$C_{0-4}$alkyl, $C_{1-10}$heteroaryl-$C_{0-4}$alkyl, $C_{3-12}$cycloalkyl and $C_{3-8}$heterocycloalkyl;
wherein said aryl-alkyl substituent of $R_2$ is optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy and methyl-piperazinyl;
$R_3$ is selected from hydrogen, halo, cyano, $C_{1-2}$alkyl, $C_{1-3}$alkoxy and halo-substituted-$C_{1-2}$alkyl;
$R_4$ is selected from hydrogen, halo, cyano, $C_{1-2}$alkyl, $C_{1-3}$alkoxy and halo-substituted-$C_{1-2}$alkyl;
$R_5$ is selected from hydrogen and $C_{1-3}$alkyl;
L is a divalent radical selected from:

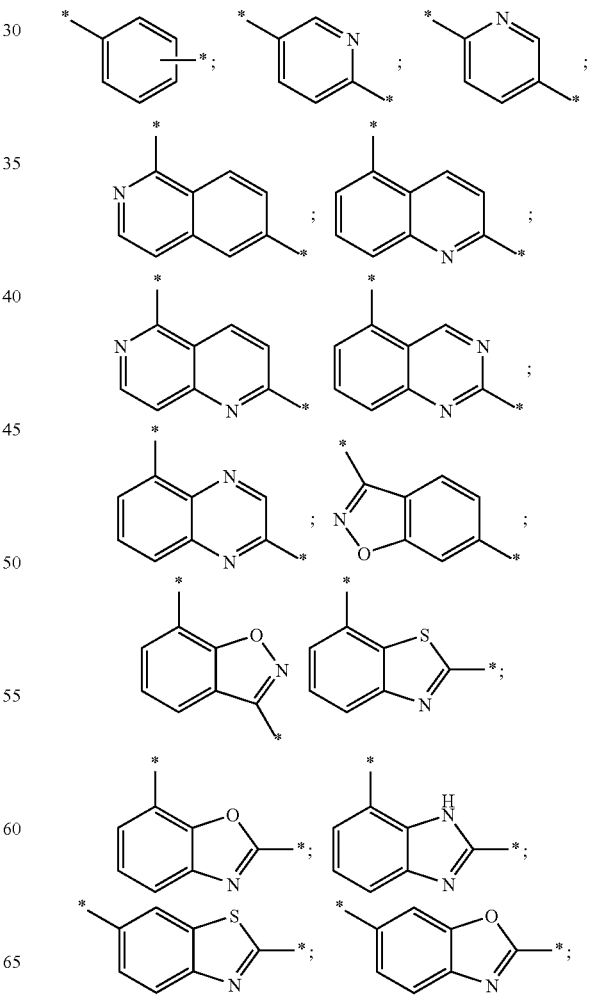

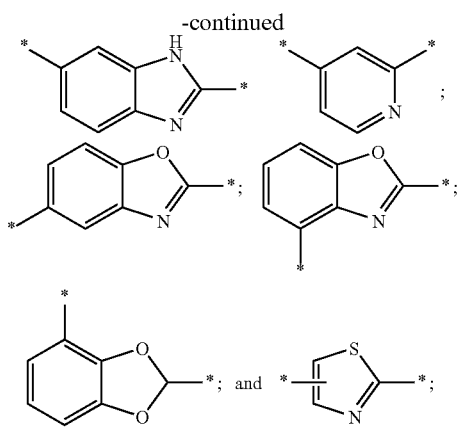

in which the asterisks indicate the point of attachment between $Y_2$ and $R_2$; wherein any divalent radical of L can be further substituted with 1 to 3 radicals independently selected from halo, hydroxy, cyano, $C_{1-4}$alkyl, $C_{1-4}$alkyl-carbonyl-amino, $C_{1-4}$alkoxy, $C_{1-4}$alkoxy-carbonyl, halo-substituted-$C_{1-4}$alkyl, $C_{1-3}$alkyl-sulfonyl, $C_{1-3}$alkyl-sulfonyl-amino, cyano-substituted-$C_{1-4}$alkyl and halo-substituted-$C_{1-4}$alkoxy; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of the hedgehog pathway activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which hedgehog pathway activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

Definitions

Unless defined otherwise, all technical and scientific terms used herein have the same meaning as commonly understood by those of ordinary skill in the art to which this invention pertains. The following references provide one of skill with a general definition of many of the terms used in this invention: *Oxford Dictionary of Biochemistry and Molecular Biology*, Smith et al. (eds.), Oxford University Press (revised ed., 2000); *Dictionary of Microbiology and Molecular Biology*, Singleton et al. (Eds.), John Wiley & Sons ($3^{rd}$ ed., 2002); and *A Dictionary of Biology (Oxford Paperback Reference)*, Martin and Hine (Eds.), Oxford University Press ($4^{th}$ ed., 2000). In addition, the following definitions are provided to assist the reader in the practice of the invention.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

As used herein, "contacting" has its normal meaning and refers to combining two or more molecules (e.g., a small molecule organic compound and a polypeptide) or combining molecules and cells (e.g., a compound and a cell). Contacting can occur in vitro, e.g., combining two or more agents or combining a compound and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

The term "hedgehog" is used to refer generically to any member of the hedgehog family, including sonic, indian, desert and tiggy winkle. The term may be used to indicate protein or gene. The term is also used to describe homolog/ortholog sequences in different animal species.

The terms "hedgehog (Hh) signaling pathway" and "hedgehog (Hh) signaling" are used interchangeably and refer to the chain of events normally mediated by various members of the signaling cascade such as hedgehog, patched (Ptch), smoothened (Smo), and Gli. The hedgehog pathway can be activated even in the absence of a hedgehog protein by activating a downstream component. For example, overexpression of Smo will activate the pathway in the absence of hedgehog.

Hh signaling components or members of Hh signaling pathway refer to gene products that participate in the Hh signaling pathway. An Hh signaling component frequently materially or substantially affects the transmission of the Hh signal in cells/tissues, typically resulting in changes in degree of downstream gene expression level and/or phenotypic changes. Hh signaling components, depending on their biological function and effects on the final outcome of the downstream gene activation/expression, may be divided into positive and negative regulators. A positive regulator is an Hh signaling component that positively affects the transmission of the Hh signal, i.e., stimulates downstream biological events when Hh is present. Examples include hedgehog, Smo, and Gli. A negative regulator is an Hh signaling component that negatively affects the transmission of the Hh signal, i.e., inhibits downstream biological events when Hh is present. Examples include (but are not limited to) Ptch and SuFu.

Hedgehog signaling antagonists, antagonists of Hh signaling or inhibitors of Hh signaling pathway refer to agents that inhibit the bioactivity of a positive Hh signaling component (such as hedgehog, Ptch, or Gli) or down-regulate the expression of the Hh signaling component. They also include agents which up-regulate a negative regulator of Hh signaling component. A hedgehog signaling antagonists may be directed to a protein encoded by any of the genes in the hedgehog pathway, including (but not limited to) sonic, indian or desert hedgehog, smoothened, ptch-1, ptch-2, gli-1, gli-2, gli-3, etc.

"Hedgehog gain-of-function" refers to an aberrant modification or mutation of a Ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the Ptc gene product to regulate the level of expression of Gli genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signaling pathway would have a 'hedgehog gain-of-function' phenotype, even if hedgehog is not mutated in that cell.

"Patched loss-of-function" refers to an aberrant modification or mutation of a Ptc gene, or a decreased level of expression of the gene, which results in a phenotype which resembles contacting a cell with a hedgehog protein, e.g., aberrant activation of a hedgehog pathway. The loss-of-function may include a loss of the ability of the Ptc gene product to regulate the level of expression of Gli genes, e.g., Gli1, Gli2 and Gli3.

"Gli gain-of-function" refers to an aberrant modification or mutation of a Gli gene, or an increased level of expression of the gene, which results in a phenotype which resembles contacting a cell with a hedgehog protein, e.g., aberrant activation of a hedgehog pathway.

The term "inhibiting" or "inhibition," in the context of tumor growth or tumor cell growth, refers to delayed appearance of primary or secondary tumors, slowed development of primary or secondary tumors, decreased occurrence of primary or secondary tumors, slowed or decreased severity of secondary effects of disease, or arrested tumor growth and regression of tumors. The term "prevent" or "prevention" refers to a complete inhibition of development of primary or secondary tumors or any secondary effects of disease. In the context of modulation of enzymatic activities, inhibition relates to reversible suppression or reduction of an enzymatic activity including competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex.

"Smoothened gain-of-function" refers to an aberrant modification or mutation of a Smo gene, or an increased level of expression of the gene, which results in a phenotype which resembles contacting a cell with a hedgehog protein, e.g., aberrant activation of a hedgehog pathway.

The term "subject" includes mammals, especially humans. It also encompasses other non-human animals such as cows, horses, sheep, pigs, cats, dogs, mice, rats, rabbits, guinea pigs, monkeys.

The term "treat" or "treatment" refers to arrested tumor growth, and to partial or complete regression of tumors. The term "treating" includes the administration of compounds or agents to prevent or delay the onset of the symptoms, complications, or biochemical indicia of a disease (e.g., lymphoma and myeloma), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The present invention relates to the discovery that signal transduction pathways regulated by hedgehog, patched (Ptc), gli and/or smoothened can be modulated by compounds of Formula I.

DESCRIPTION OF PREFERRED EMBODIMENTS

The therapeutic methods of the invention employ an antagonist of the hedgehog signaling pathway to inhibit growth and proliferation of non-melanoma skin cancer, myeloma, lymphoma, psoriasis, pancreatic cancer, prostrate cancer, medulloblastoma, basal cell carcinoma and small-cell lung cancer. These methods involve contacting such a tumor cell (in vitro or in vivo) with an inhibitor of the Hh signaling pathway, a compound of Formula I. In one embodiment, with respect to compounds of Formula I:

n is selected from 0 and 1;

$Y_1$ is selected from a bond and C(O);

$Y_2$ is selected from a bond, C(O) and $S(O)_2$;

$R_1$ is selected from hydrogen, halo and $C_{1-2}$alkyl;

$R_2$ is selected from hydrogen, halo, cyano, $C_{1-3}$alkyl, $C_{1-3}$alkoxy, halo-substituted-$C_{1-3}$alkyl, halo-substituted-$C_{1-3}$alkoxy, $C_{6-10}$aryl-$C_{0-4}$alkyl, $C_{1-10}$heteroaryl-$C_{0-4}$alkyl, $C_{3-12}$cycloalkyl-$C_{0-4}$alkyl, $C_{3-8}$heterocycloalkyl-$C_{0-4}$alkyl and phenoxy;

wherein said aryl, heteroaryl, cycloalkyl, heterocycloalkyl or phenoxy of $R_2$ can be optionally substituted with 1 to 3 radicals independently selected from $C_{1-6}$alkyl, halo-substituted-$C_{1-6}$alkyl, $C_{1-6}$alkoxy and halo-substituted-$C_{1-6}$alkoxy;

$R_3$ is selected from hydrogen, halo, cyano, $C_{1-2}$alkyl, $C_{1-3}$alkoxy, halo-substituted-$C_{1-2}$alkyl and —$NR_{6a}R_{6b}$; wherein $R_{6a}$ and $R_{6b}$ are independently selected from hydrogen and $C_{1-4}$alkyl;

$R_4$ is selected from hydrogen, halo, cyano, $C_{1-2}$alkyl and halo-substituted-$C_{1-2}$alkyl;

$R_5$ is selected from hydrogen and $C_{1-3}$alkyl;

L is a divalent radical selected from:

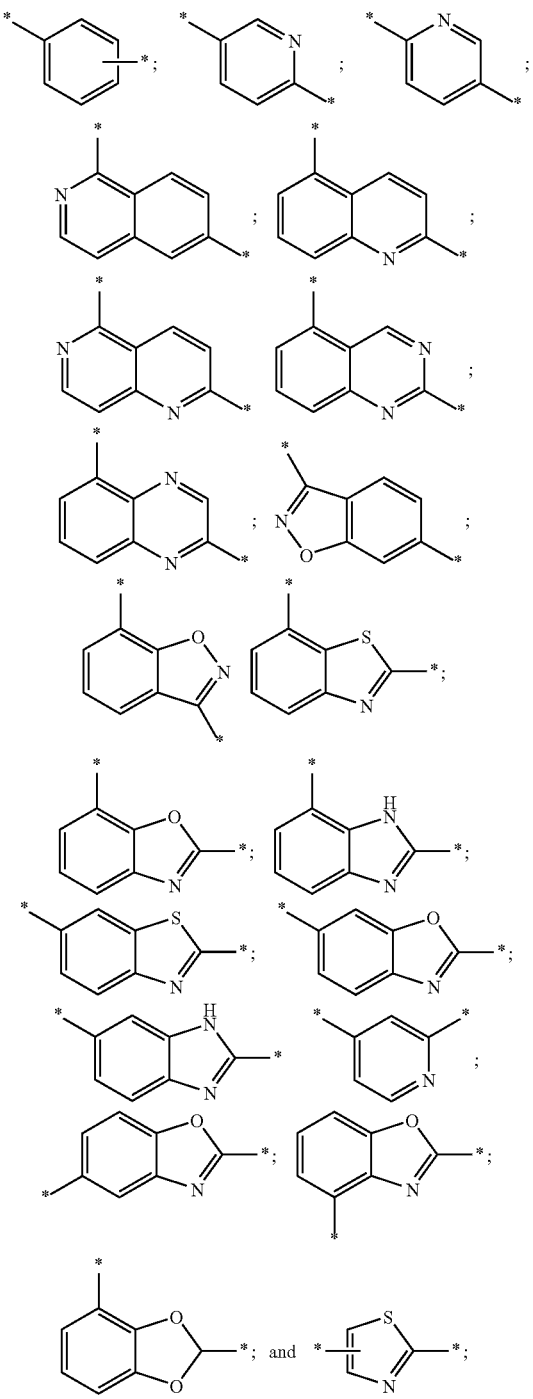

in which the asterisks indicate the point of attachment between $Y_2$ and $R_2$; wherein any divalent radical of L can be further substituted with 1 to 3 radicals independently selected from halo, hydroxy, cyano, $C_{1-4}$alkyl, $C_{1-3}$alkyl-sulfonyl, $C_{1-3}$alkyl-sulfonyl-amino, $C_{1-3}$alkyl-carbonyl-amino, $C_{1-3}$alkoxy, $C_{1-3}$alkoxy-carbonyl, halo-substituted-$C_{1-3}$alkyl, cyano-substituted-$C_{1-3}$alkyl and halo-substituted-$C_{1-3}$alkoxy.

In another embodiment, n is selected from 0 and 1; $Y_1$ is selected from a bond and C(O); $Y_2$ is selected from a bond, C(O) and $S(O)_2$; and $R_1$ is selected from hydrogen, chloro and methyl.

In another embodiment, $R_2$ is selected from hydrogen, halo, methyl, ethyl, cyano, methoxy, ethoxy, trifluoromethyl, trifluoromethoxy, phenoxy, morpholino, morpholino-methyl, cyclohexyl, thiomorpholino, 1H-tetrazol-1-yl, piperidinyl and azepan-1-yl; wherein said phenoxy, morpholino, morpholino-methyl, cyclohexyl, thiomorpholino, 1H-tetrazol-1-yl, piperidinyl or azepan-1-yl of $R_2$ can be optionally substituted with 1 to 3 methyl radicals; wherein said sulfur of thiomorpholino can be bound to 0, 1 or 2 oxygen atoms.

In another embodiment, $R_3$ is selected from hydrogen, chloro, fluoro, cyano, trifluoromethyl, methoxy and diethylamino; $R_4$ is selected from hydrogen and chloro; $R_5$ is selected from hydrogen and methyl; and L is a divalent radical selected from:

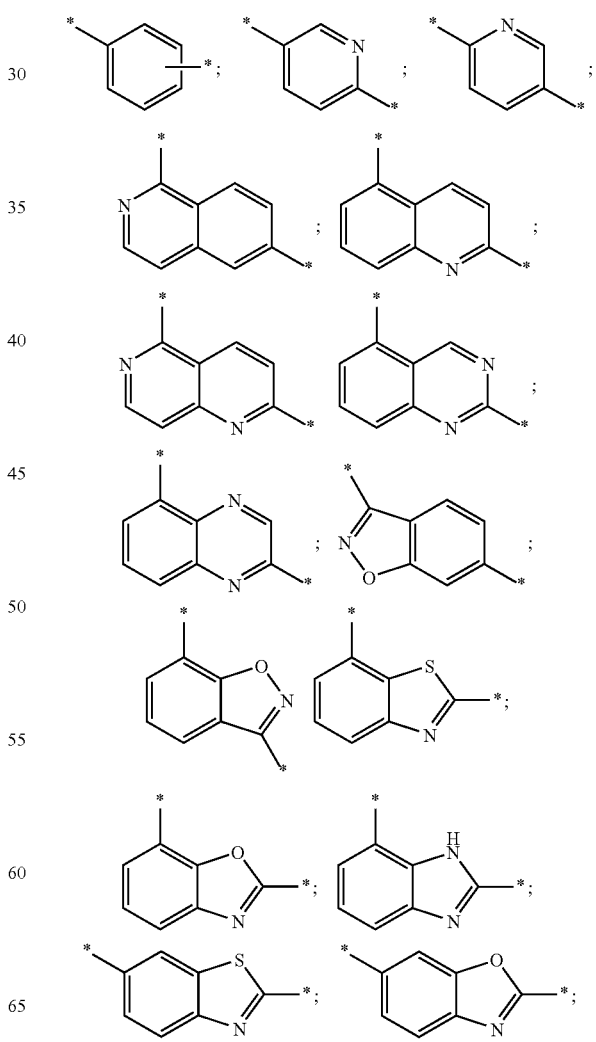

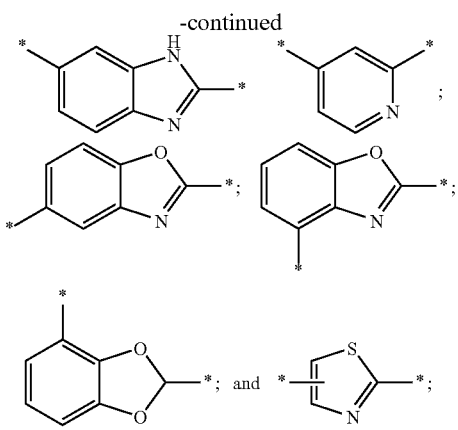

in which the asterisks indicate the point of attachment between $Y_2$ and $R_2$; wherein any divalent radical of L can be further substituted with 1 to 3 radicals independently selected from hydroxy, bromo, chloro, fluoro, methyl, ethyl, cyano, methyl-carbonyl-amino, butyl, methoxy, trifluoromethyl, trifluoroethoxy, 2-cyanopropan-2-yl, trifluoromethoxy, methoxy-carbonyl, propoxy, methyl-sulfonyl, methyl-sulfonylamino, ethyl-sulfonyl, propyl-sulfonyl, isopropyl-sulfonyl, isopropoxy and ethoxy.

Preferred compounds of Formula I are selected from [4-Chloro-3-(5-phenyl-1H-imidazol-2-yl)-phenyl]-[6-(2-methyl-morpholin-4-yl)-isoquinolin-1-yl]-amine, [4-Chloro-3-(5-phenyl-1H-imidazol-2-yl)-phenyl]-[2-(2-methyl-morpholin-4-yl)-quinolin-5-yl]-amine, [4-Chloro-3-(5-phenyl-1H-imidazol-2-yl)-phenyl]-[2-(2-methyl-morpholin-4-yl)-[1,6]naphthyridin-5-yl]-amine, [4-Chloro-3-(5-phenyl-1H-imidazol-2-yl)-phenyl]-[6-(2,6-dimethyl-morpholin-4-yl)-isoquinolin-1-yl]-amine, [4-Chloro-3-(5-phenyl-1H-imidazol-2-yl)-phenyl]-(6-morpholin-4-yl-isoquinolin-1-yl)-amine, N-[4-Chloro-3-(4-phenyl-1H-imidazol-2-yl)-phenyl]-4-morpholin-4-yl-benzamide, N-[4-Chloro-3-(4-phenyl-1H-imidazol-2-yl)-phenyl]-4-cyclohexyl-benzamide, [4-Chloro-3-(5-phenyl-1H-imidazol-2-yl)-phenyl]-(2-morpholin-4-yl-quinolin-5-yl)-amine, [4-Methyl-3-(5-phenyl-1H-imidazol-2-yl)-phenyl]-(6-piperidin-1-yl-isoquinolin-1-yl)-amine, (6-Azepan-1-yl-isoquinolin-1-yl)-[4-methyl-3-(5-phenyl-1H-imidazol-2-yl)-phenyl]-amine, N-[4-Methyl-3-(4-phenyl-1H-imidazol-2-yl)-phenyl]-4-morpholin-4-yl-benzamide, 4-Cyclohexyl-N-[4-methyl-3-(4-phenyl-1H-imidazol-2-yl)-phenyl]-benzamide, N-{3-[5-(4-Chloro-phenyl)-1H-imidazol-2-yl]-4-methyl-phenyl}-4-morpholin-4-yl-benzamide, [4-Methyl-3-(5-phenyl-1H-imidazol-2-yl)-phenyl]-(2-morpholin-4-yl-[1,6]naphthyridin-5-yl)-amine, (6-Azepan-1-yl-isoquinolin-1-yl)-[4-chloro-3-(5-phenyl-1H-imidazol-2-yl)-phenyl]-amine, [4-Chloro-3-(5-phenyl-1H-imidazol-2-yl)-phenyl]-(7-morpholin-4-yl-isoquinolin-1-yl)-amine, [4-Chloro-3-(5-phenyl-1H-imidazol-2-yl)-phenyl]-(6-piperidin-1-yl-isoquinolin-1-yl)-amine, 3,5-Dimethoxy-N-[4-methyl-3-(5-phenyl-1H-imidazol-2-yl)-phenyl]-benzamide, N-{3-[4-(4-Diethylamino-phenyl)-1H-imidazol-2-yl]-4-methyl-phenyl}-4-morpholin-4-yl-benzamide, N-{4-Chloro-3-[4-(4-chloro-phenyl)-1H-imidazol-2-yl]-phenyl}-4-morpholin-4-yl-benzamide, (6-Morpholin-4-yl-isoquinolin-1-yl)-[3-(5-phenyl-1H-imidazol-2-yl)-phenyl]-amine, N-{3-[5-(4-Fluoro-phenyl)-1H-imidazol-2-yl]-4-methyl-phenyl}-4-morpholin-4-yl-benzamide, (6-Morpholin-4-yl-isoquinolin-1-yl)-[3-(5-phenyl-1H-imidazol-2-yl)-phenyl]-amine, (2-Morpholin-4-yl-quinolin-5-yl)-[3-(5-phenyl-1H-imidazol-2-yl)-phenyl]-amine, 6-Morpholin-4-yl-N-[3-(4-phenyl-1H-imidazol-2-yl)-phenyl]-nicotinamide, N-{3-[5-(3-Chloro-phenyl)-1H-imidazol-2-yl]-4-methyl-phenyl}-4-morpholin-4-yl-benzamide, 4-Cyclohexyl-N-[3-(5-phenyl-1H-imidazol-2-yl)-phenyl]-benzamide, 4-Morpholin-4-yl-N-[3-(4-phenyl-1H-imidazol-2-yl)-phenyl]-benzamide, N-{3-[5-(2-Chloro-phenyl)-1H-imidazol-2-yl]-4-methyl-phenyl}-4-morpholin-4-yl-benzamide, 4-Cyclohexyl-N-{3-[4-(4-fluoro-phenyl)-1H-imidazol-2-yl]-phenyl}-benzamide, N-{3-[5-(4-Cyano-phenyl)-1H-imidazol-2-yl]-4-methyl-phenyl}-3,5-dimethoxy-benzamide, 6-Azepan-1-yl-N-[3-(4-phenyl-1H-imidazol-2-yl)-phenyl]-nicotinamide, 4-Morpholin-4-yl-N-[3-(5-phenyl-1H-imidazol-2-yl)-phenyl]-benzamide, N-{4-Methyl-3-[5-(4-trifluoromethyl-phenyl)-1H-imidazol-2-yl]-phenyl}-4-morpholin-4-yl-benzamide, [4-Chloro-3-(5-phenyl-1H-imidazol-2-yl)-phenyl]-isoquinolin-1-yl-amine, 4-Cyclohexyl-N-{3-[4-(4-methoxy-phenyl)-1H-imidazol-2-yl]-phenyl}-benzamide, 3,4,5,6-Tetrahydro-2H-[1,2']bipyridinyl-5'-carboxylic acid [3-(4-phenyl-1H-imidazol-2-yl)-phenyl]-amide, 6-Azepan-1-yl-N-[2-methyl-3-(4-phenyl-1H-imidazol-2-yl)-phenyl]-nicotinamide, N-{3-[4-(4-Cyano-phenyl)-1H-imidazol-2-yl]-phenyl}-4-cyclohexyl-benzamide, 4-Morpholin-4-yl-N-[3-(5-phenyl-1H-imidazol-2-yl)-phenyl]-benzenesulfonamide, [2-Methyl-3-(5-phenyl-1H-imidazol-2-yl)-phenyl]-(6-morpholin-4-yl-isoquinolin-1-yl)-amine, N-[4-Chloro-3-(5-methyl-4-phenyl-1H-imidazol-2-yl)-phenyl]-4-morpholin-4-yl-benzamide, N-[4-Methyl-3-(5-methyl-4-phenyl-1H-imidazol-2-yl)-phenyl]-4-morpholin-4-yl-benzamide, N-(6-Morpholin-4-yl-pyridin-3-yl)-3-(4-phenyl-1H-imidazol-2-yl)-benzamide, N-[2-Methyl-3-(4-phenyl-1H-imidazol-2-yl)-phenyl]-6-morpholin-4-yl-nicotinamide, 3,4,5,6-Tetrahydro-2H-[1,2']bipyridinyl-5'-carboxylic acid [2-methyl-3-(4-phenyl-1H-imidazol-2-yl)-phenyl]-amide, 4-Cyclohexyl-N-[2-methyl-3-(4-phenyl-1H-imidazol-2-yl)-phenyl]-benzamide, [4-Chloro-3-(5-phenyl-1H-imidazol-2-yl)-phenyl]-[2-(2,6-dimethyl-morpholin-4-yl)-quinolin-5-yl]-amine, [4-Chloro-3-(4-phenyl-1H-imidazol-2-yl)-phenyl]-[2-(2,6-dimethyl-morpholin-4-yl)-[1,6]naphthyridin-5-yl]-amine, N-[4-Chloro-3-(5-phenyl-1H-imidazol-2-yl)-phenyl]-2-methoxy-isonicotinamide, 2-Chloro-N-[4-chloro-3-(5-phenyl-1H-imidazol-2-yl)-phenyl]-6-methyl-isonicotinamide, 2,6-Dichloro-N-[4-chloro-3-(5-phenyl-1H-imidazol-2-yl)-phenyl]-isonicotinamide, N-[4-Chloro-3-(5-phenyl-1H-imidazol-2-yl)-phenyl]-2-methoxy-isonicotinamide, 6-Chloro-N-[4-chloro-3-(5-phenyl-1H-imidazol-2-yl)-phenyl]-nicotinamide, N-[4-Chloro-3-(5-phenyl-1H-imidazol-2-yl)-phenyl]-6-trifluoromethyl-nicotinamide, 2-Chloro-N-[4-chloro-3-(5-phenyl-1H-imidazol-2-yl)-phenyl]-6-methoxy-isonicotinamide, Quinoline-3-carboxylic acid [4-chloro-3-(5-phenyl-1H-imidazol-2-yl)-phenyl]-amide, N-[4-Chloro-3-(5-phenyl-1H-imidazol-2-yl)-phenyl]-nicotinamide, N-[4-Chloro-3-(5-phenyl-1H-imidazol-2-yl)-phenyl]-5-methoxy-2-(2,2,2-trifluoro-ethoxy)-benzamide, N-[4-Chloro-3-(5-phenyl-1H-imidazol-2-yl)-phenyl]-3,4-diethoxy-benzamide, N-[4-Chloro-3-(5-phenyl-1H-imidazol-2-yl)-phenyl]-3-methoxy-4-methyl-benzamide, 4-Chloro-N-[4-chloro-3-(5-phenyl-1H-imidazol-2-yl)-phenyl]-3-methoxy-benzamide, 2,2-Difluoro-benzo[1,3]dioxole-4-carboxylic acid [4-chloro-3-(5-phenyl-1H-imidazol-2-yl)-phenyl]-amide, N-[4-Chloro-3-(5-phenyl-1H-imidazol-2-yl)-phenyl]-3-methoxy-2-methyl-benzamide, N-[4-Chloro-3-(5-phenyl-1H-imidazol-2-yl)-phenyl]-2,5-dimethoxy-benzamide, N-[4-Chloro-3-(5-phenyl-1H-imidazol-2-yl)-phenyl]-3,5-dimethoxy-4-methyl-benzamide, 6-Methyl-benzo[1,3]dioxole-5-carboxylic acid [4-chloro-3-(5-phenyl-1H-imidazol-2-yl)- phenyl]-amide, [4-Chloro-3-(4-phenyl-1H-imidazol-2-yl)-phenyl]-[7-(2,6-dimethyl-morpholin-4-yl)-quinolin-4-yl]-amine, [4-Chloro-3-(5-phenyl-1H-imidazol-2-yl)-phenyl]-[8-methyl-2-(2-methyl-morpholin-4-yl)-quinolin-5-yl]-amine, [4-Chloro-3-(5-phenyl-1H-imidazol-2-yl)-phenyl]-[2-(2-methyl-morpholin-4-yl)-quinazolin-5-yl]-amine, [4-Chloro-3-(5-phenyl-1H-imidazol-2-yl)-phenyl]-[2-(2,6-dimethyl-morpholin-4-yl)-quinazolin-5-yl]-amine, [4-Chloro-3-(5-phenyl-1H-imidazol-2-yl)-phenyl]-[2-(2-methyl-morpholin-4-yl)-quinoxalin-5-yl]-amine, [2-(2,6-Dimethyl-morpholin-4-yl)-quinoxalin-5-yl]-[4-methyl-3-(5-phenyl-1H-imidazol-2-yl)-phenyl]-amine, [4-Chloro-3-(5-phenyl-1H-imidazol-2-yl)-phenyl]-[3-(2-methyl-morpholin-4-yl)-benzo[d]isoxazol-7-yl]-amine, [4-Chloro-3-(5-phenyl-1H-imidazol-2-yl)-phenyl]-[6-(2-methyl-morpholin-4-yl)-benzo[d]isoxazol-3-yl]-amine, [4-Chloro-3-(5-phenyl-1H-imidazol-2-yl)-phenyl]-[2-(2-methyl-morpholin-4-yl)-benzooxazol-4-yl]-amine, [4-Chloro-3-(5-phenyl-1H-imidazol-2-yl)-phenyl]-[2-(2-methyl-morpholin-4-yl)-1H-benzoimidazol-4-yl]-amine, [2-(2,6-Dimethyl-morpholin-4-yl)-benzothiazol-4-yl]-[4-methyl-3-(5-phenyl-1H-imidazol-2-yl)-phenyl]-amine, [2-(2,6-Dimethyl-morpholin-4-yl)-benzothiazol-7-yl]-[4-methyl-3-(5-phenyl-1H-imidazol-2-yl)-phenyl]-amine, [4-Chloro-3-(5-phenyl-1H-imidazol-2-yl)-phenyl]-[3-(2-methyl-morpholin-4-yl)-benzo[d]isoxazol-5-yl]-amine, [4-Chloro-3-(5-phenyl-1H-imidazol-2-yl)-phenyl]-[2-(2-methyl-morpholin-4-yl)-benzooxazol-5-yl]-amine, [2-(2,6-Dimethyl-morpholin-4-yl)-1H-benzoimidazol-4-yl]-[4-methyl-3-(5-phenyl-1H-imidazol-2-yl)-phenyl]-amine, N-(4-chloro-3-(5-phenyl-1H-imidazol-2-yl)phenyl)-3-methoxybenzamide, N-(4-chloro-3-(5-phenyl-1H-imidazol-2-yl)phenyl)-2-methylbenzamide, N-(4-chloro-3-(5-phenyl-1H-imidazol-2-yl)phenyl)-2-(trifluoromethyl)benzamide, N-(4-chloro-3-(5-phenyl-1H-imidazol-2-yl)phenyl)-2,3-dimethoxybenzamide, N-(4-chloro-3-(5-phenyl-1H-imidazol-2-yl)phenyl)benzo[d]thiazole-6-carboxamide, N-(4-chloro-3-(5-phenyl-1H-imidazol-2-yl)phenyl)picolinamide, N-(4-chloro-3-(5-phenyl-1H-imidazol-2-yl)phenyl)-3-(trifluoromethoxy)benzamide, N-(4-chloro-3-(5-phenyl-1H-imidazol-2-yl)phenyl)-4-methoxy-2-methylbenzamide, N-(4-chloro-3-(5-phenyl-1H-imidazol-2-yl)phenyl)-2-hydroxynicotinamide, N-(4-chloro-3-(5-phenyl-1H-imidazol-2-yl)phenyl)-2-hydroxy-6-methylnicotinamide, N-(4-chloro-3-(5-phenyl-1H-imidazol-2-yl)phenyl)-2-methoxyisonicotinamide, N-(4-chloro-3-(5-phenyl-1H-imidazol-2-yl)phenyl)-3-methylpicolinamide, N-(4-chloro-3-(5-phenyl-1H-imidazol-2-yl)phenyl)-3-ethoxy-2-methylbenzamide, N-(4-chloro-3-(5-phenyl-1H-imidazol-2-yl)phenyl)-6-(2,2,2-trifluoroethoxy)nicotinamide, 2-chloro-N-(4-chloro-3-(5-phenyl-1H-imidazol-2-yl)phenyl)-6-(trifluoromethyl)nicotinamide, 6-bromo-N-(4-chloro-3-(5-phenyl-1H-imidazol-2-yl)phenyl)nicotinamide, N-(4-chloro-3-(5-phenyl-1H-imidazol-2-yl)phenyl)-6-cyanonicotinamide, N-(4-chloro-3-(5-phenyl-1H-imidazol-2-yl)phenyl)-6-methylnicotinamide, N-(4-chloro-3-(5-phenyl-1H-imidazol-2-yl)phenyl)-6-hydroxynicotinamide, N-(4-chloro-3-(5-phenyl-1H-imidazol-2-yl)phenyl)-2-methoxynicotinamide, N-(4-chloro-3-(5-phenyl-1H-imidazol-2-yl)phenyl)-5-methylnicotinamide, N-(4-chloro-3-(5-phenyl-1H-imidazol-2-yl)phenyl)-5-fluoronicotinamide, 5-bromo-N-(4-chloro-3-(5-phenyl-1H-imidazol-2-yl)phenyl)nicotinamide, N-(4-chloro-3-(5-phenyl-1H-imidazol-2-yl)phenyl)-2-ethoxynicotinamide, N-(4-chloro-3-(5-phenyl-1H-imidazol-2-yl)phenyl)-2-ethyl-3-methoxybenzamide, N-(4-chloro-3-(5-phenyl-1H-imidazol-2-yl)phenyl)-6-methoxynicotinamide, N-(4-chloro-3-(5-phenyl-1H-imidazol-2-yl)phenyl)-2-fluoronicotinamide, 2-chloro-N-(4-chloro-3-(5-phenyl-1H-imidazol-2-yl)phenyl)nicotinamide, 2-chloro-N-(4-chloro-3-(5-phenyl-1H-imidazol-2-yl)phenyl)-6-methylnicotinamide, 5,6-dichloro-N-(4-chloro-3-(5-phenyl-1H-imidazol-2-yl)phenyl)nicotinamide, N-(4-chloro-3-(5-phenyl-1H-imidazol-2-yl)phenyl)-2-methylnicotinamide, N-(4-chloro-3-(5-phenyl-1H-imidazol-2-yl)phenyl)-2-ethoxyisonicotinamide, 2-chloro-N-(4-chloro-3-(5-phenyl-1H-imidazol-2-yl)phenyl) isonicotinamide, N-(4-chloro-3-(5-phenyl-1H-imidazol-2-yl)phenyl)isonicotinamide, methyl 6-(4-chloro-3-(5-phenyl-1H-imidazol-2-yl)phenylcarbamoyl)nicotinate, N-(4-chloro-3-(5-phenyl-1H-imidazol-2-yl)phenyl)-2-(2-cyanopropan-2-yl)isonicotinamide, 2-tert-butyl-N-(4-chloro-3-(5-phenyl-1H-imidazol-2-yl)phenyl) isonicotinamide, 4'-cyano-2-methyl-N-(6-thiomorpholinopyridin-3-yl)biphenyl-3-carboxamide, N-(4-chloro-3-(5-phenyl-1H-imidazol-2-yl) phenyl)-3-fluoroisonicotinamide, 2-bromo-N-(4-chloro-3-(5-phenyl-1H-imidazol-2-yl)phenyl)isonicotinamide, 3-bromo-N-(4-chloro-3-(5-phenyl-1H-imidazol-2-yl)phenyl)-2-fluorobenzamide, 2-chloro-N-(4-chloro-3-(5-phenyl-1H-imidazol-2-yl)phenyl)-3,4-dimethoxybenzamide, 3-chloro-N-(4-chloro-3-(5-phenyl-1H-imidazol-2-yl)phenyl) isonicotinamide, N-(4-chloro-3-(5-phenyl-1H-imidazol-2-yl)phenyl)-2-methylisonicotinamide, 4-chloro-N-(4-chloro-3-(5-phenyl-1H-imidazol-2-yl)phenyl)nicotinamide, 2,5-dichloro-N-(4-chloro-3-(5-phenyl-1H-imidazol-2-yl) phenyl)isonicotinamide, N-(4-chloro-3-(5-phenyl-1H-imidazol-2-yl)phenyl)-2-(1H-tetrazol-1-yl)isonicotinamide, 4-bromo-N-(4-chloro-3-(5-phenyl-1H-imidazol-2-yl)phenyl)picolinamide, 2,6-dichloro-N-(4-chloro-3-(5-phenyl-1H-imidazol-2-yl)phenyl)isonicotinamide, N-(4-chloro-3-(5-phenyl-1H-imidazol-2-yl)phenyl)-4-methylnicotinamide, N-(4-chloro-3-(5-phenyl-1H-imidazol-2-yl)phenyl)-2-hydroxy-6-(trifluoromethyl)nicotinamide, 2-acetamido-N-(4-chloro-3-(5-phenyl-1H-imidazol-2-yl)phenyl)isonicotinamide, 3-bromo-N-(4-chloro-3-(5-phenyl-1H-imidazol-2-yl)phenyl)-2-methylbenzamide, 2-chloro-N-(4-chloro-3-(5-phenyl-1H-imidazol-2-yl)phenyl)-6-methylbenzamide, N-(4-chloro-3-(5-phenyl-1H-imidazol-2-yl)phenyl)-3-(trifluoromethyl)benzamide, N-(4-chloro-3-(4-phenyl-1H-imidazol-2-yl)phenyl)-3-(morpholinomethyl)pyridin-2-amine, N-(4-chloro-3-(5-phenyl-1H-imidazol-2-yl)phenyl)-6-hydroxypicolinamide, N-(4-chloro-3-(5-phenyl-1H-imidazol-2-yl)phenyl)-3-hydroxypicolinamide, 6-bromo-N-(4-chloro-3-(5-phenyl-1H-imidazol-2-yl)phenyl)picolinamide, N-(4-chloro-3-(5-phenyl-1H-imidazol-2-yl)phenyl)-6-methylpicolinamide, 5-butyl-N-(4-chloro-3-(5-phenyl-1H-imidazol-2-yl)phenyl)picolinamide, 4-chloro-N-(4-chloro-3-(5-phenyl-1H-imidazol-2-yl)phenyl)picolinamide, N-(4-chloro-3-(5-phenyl-1H-imidazol-2-yl)phenyl)-2,6-dimethoxynicotinamide, N-(4-chloro-3-(5-phenyl-1H-imidazol-2-yl)phenyl)-6-phenoxynicotinamide, N-(4-chloro-3-(5-phenyl-1H-imidazol-2-yl)phenyl)-2,6-dimethoxyisonicotinamide, 6-chloro-N-(4-chloro-3-(5-phenyl-1H-imidazol-2-yl)phenyl)picolinamide, N-(4-chloro-3-(5-phenyl-1H-imidazol-2-yl)phenyl)-2-fluoroisonicotinamide, N-(4-chloro-3-(5-phenyl-1H-imidazol-2-yl)phenyl)-6-ethoxynicotinamide, N-(4-chloro-3-(5-phenyl-1H-imidazol-2-yl)phenyl)-2-(2,2,2-trifluoroethoxy)isonicotinamide, N-(4-chloro-3-(5-phenyl-1H-imidazol-2-yl)phenyl)-6-isopropoxynicotinamide, N-(4-chloro-3-(5-phenyl-1H-imidazol-2-yl)phenyl)-6-propoxynicotinamide, 2,3-dichloro-N-(4-chloro-3-(5-phenyl-1H-imidazol-2-yl)phenyl)isonicotinamide, N-(4-chloro-3-(5-phenyl-1H-imidazol-2-yl)phenyl)-2-hydroxy-6- methylisonicotinamide, N-(4-chloro-3-(5-phenyl-1H-imidazol-2-yl)phenyl)-2-propoxyisonicotinamide, N-(4-chloro-3-(5-phenyl-1H-imidazol-2-yl)phenyl)-2-methyl-6-(trifluoromethyl)nicotinamide, 5-chloro-N-(4-chloro-3-(5-phenyl-1H-imidazol-2-yl)phenyl)-2-methoxyisonicotinamide, 3-chloro-N-(4-chloro-3-(5-phenyl-1H-imidazol-2-yl)phenyl)-2-methoxyisonicotinamide, 3,5-dichloro-N-(4-chloro-3-(5-phenyl-1H-imidazol-2-yl)phenyl)isonicotinamide, 2,6-dichloro-N-(4-chloro-3-(5-phenyl-1H-imidazol-2-yl)phenyl)nicotinamide, 2-chloro-N-(4-chloro-3-(5-phenyl-1H-imidazol-2-yl)phenyl)-4-(methylsulfonyl)benzamide, 2,3-dichloro-N-(4-chloro-3-(5-phenyl-1H-imidazol-2-yl)phenyl)benzamide, N-(4-chloro-3-(5-phenyl-1H-imidazol-2-yl)phenyl)-4-isopropoxy-2-methylbenzamide, N-(4-chloro-3-(5-phenyl-1H-imidazol-2-yl)phenyl)-3-isopropoxy-2-methylbenzamide, N-(4-chloro-3-(5-phenyl-1H-imidazol-2-yl)phenyl)-2-isopropoxyisonicotinamide, 2-chloro-N-(4-chloro-3-(5-phenyl-1H-imidazol-2-yl)phenyl)-6-methoxynicotinamide, 2-chloro-N-(4-chloro-3-(5-phenyl-1H-imidazol-2-yl)phenyl)-4-ethoxybenzamide, 2-chloro-N-(4-chloro-3-(5-phenyl-1H-imidazol-2-yl)phenyl)-4-isopropoxybenzamide, 2-chloro-N-(4-chloro-3-(5-phenyl-1H-imidazol-2-yl)phenyl)-6-isopropoxynicotinamide, N-(4-chloro-3-(5-phenyl-1H-imidazol-2-yl)phenyl)-6-methoxy-2-methylnicotinamide, 2,3-dichloro-N-(4-chloro-3-(5-phenyl-1H-imidazol-2-yl)phenyl)-4-(ethylsulfonyl)benzamide, 2-((2S,6R)-2,6-dimethylmorpholino)-N-(4-methyl-3-(4-phenyl-1H-imidazol-2-yl)phenyl)thiazole-5-carboxamide, 2-chloro-N-(4-chloro-3-(5-phenyl-1H-imidazol-2-yl)phenyl)-4-(ethylsulfonyl)benzamide, 2-chloro-N-(4-chloro-3-(5-phenyl-1H-imidazol-2-yl)phenyl)-4-(isopropylsulfonyl)benzamide, 2-chloro-N-(4-chloro-3-(5-phenyl-1H-imidazol-2-yl)phenyl)-4-(propylsulfonyl)benzamide, and 2-chloro-N-(4-chloro-3-(5-phenyl-1H-imidazol-2-yl)phenyl)-4-(methylsulfonamido)-benzamide.

It is, therefore, specifically contemplated that compounds of Formula I which interfere with aspects of hedgehog, Ptc, or smoothened signal transduction activity will likewise be capable of inhibiting proliferation (or other biological consequences) in normal cells and/or cells having a patched loss-of-function phenotype, a hedgehog gain-of-function phenotype, a smoothened gain-of-function phenotype or a Gli gain-of-function phenotype. Thus, it is contemplated that in certain embodiments, these compounds may be useful for inhibiting hedgehog activity in normal cells, e.g., which do not have a genetic mutation that activates the hedgehog pathway. In preferred embodiments, the compounds are capable of inhibiting at least some of the biological activities of hedgehog proteins, preferably specifically in target cells.

Thus, the methods of the present invention include the use of compounds of Formula I which agonize Ptc inhibition of hedgehog signaling, such as by inhibiting activation of smoothened or downstream components of the signal pathway, in the regulation of repair and/or functional performance of a wide range of cells, tissues and organs, including normal cells, tissues, and organs, as well as those having the phenotype of Ptc loss-of-function, hedgehog gain-of-function, smoothened gain-of-function or Gli gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo).

In another embodiment, the subject method can be to treat epithelial cells having a phenotype of Ptc loss-of-function, hedgehog gain-of-function, smoothened gain-of-function, Gli gain-of-function, or an over expression of hedgehog ligands phenotype. For instance, the subject method can be used in treating or preventing basal cell carcinoma or other hedgehog pathway-related disorders.

In certain embodiments, a compound of Formula I can inhibit activation of a hedgehog pathway by binding to smoothened or its downstream proteins. In certain embodiments, a subject antagonist may inhibit activation of a hedgehog pathway by binding to patched.

In another preferred embodiment, the subject method can be used as part of a treatment regimen for malignant medulloblastomas and other primary CNS malignant neuroectodermal tumors.

In another aspect, the present invention provides pharmaceutical preparations comprising, as an active ingredient, a hedgehog signaling modulator such as a compound of Formula I, a Ptc agonist, a smoothened antagonist, or downstream hedgehog pathway protein antagonist such as described herein, formulated in an amount sufficient to inhibit, in vivo, proliferation or other biological consequences of Ptc loss-of-function, hedgehog gain-of-function, smoothened gain-of-function or Gli gain-of-function.

The subject treatments using a compound of Formula I, patched agonists, smoothened antagonists, or downstream hedgehog pathway protein antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

Pharmacology and Utility

The present invention makes available methods and compounds for inhibiting activation of the hedgehog signaling pathway, e.g., to inhibit aberrant growth states resulting from phenotypes such as Ptc loss-of-function, hedgehog gain-of-function, smoothened gain-of-function or Gli gain-of-function, comprising contacting the cell with a compound of Formula I, in a sufficient amount to agonize a normal Ptc activity, antagonize a normal hedgehog activity, antagonize smoothened activity, or antagonize Gli activity e.g., to reverse or control the aberrant growth state.

Members of the Hedgehog family of signaling molecules mediate many important short- and long-range patterning processes during vertebrate development. Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation. The effects of developmental cell interactions are varied: responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation.

The vertebrate family of hedgehog genes includes three members that exist in mammals, known as Desert (Dhh), Sonic (Shh) and Indian (Ihh) hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

An inactive Hedgehog signaling pathway is where the transmembrane protein receptor Patched (Ptc) inhibits the activity of Smoothened (Smo), a seven transmembrane protein. The transcription factor Gli, a downstream component of Hh signaling, is prevented from entering the nucleus through interactions with cytoplasmic proteins, including Fused and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc. Ligand binding results in a reversal of the repression of Smo, thereby activating a cascade that leads to the translocation of the active form of the transcription factor Gli to the nucleus. Nuclear Gli activates target gene expression, including Ptc and Gli itself.

Increased levels of Hedgehog signaling are sufficient to initiate cancer formation and are required for tumor survival. These cancers include, but are not limited to, prostate cancer ("Hedgehog signaling in prostate regeneration, neoplasia and metastasis", Karhadkar S S, Bova G S, Abdallah N, Dhara S, Gardner D, Maitra A, Isaacs J T, Berman D M, Beachy P A., Nature. Oct. 7, 2004; 431(7009):707-12; "Inhibition of prostate cancer proliferation by interference with SONIC HEDGEHOG-GLI1 signaling", Sanchez P, Hernandez A M, Stecca B, Kahler A J, DeGueme A M, Barrett A, Beyna M, Datta M W, Datta S, Ruiz i Altaba A., Proc Natl Acad Sci USA. Aug. 24, 2004;101(34):12561-6), breast cancer ("Hedgehog signaling pathway is a new therapeutic target for patients with breast cancer", Kubo M, Nakamura M, Tasaki A, Yamanaka N, Nakashima H, Nomura M, Kuroki S, Katano M., Cancer Res. Sep. 1, 2004;64(17):6071-4), medulloblastoma ("Medulloblastoma growth inhibition by hedgehog pathway blockade", Berman D M, Karhadkar S S, Hallahan A R, Pritchard J I, Eberhart C G, Watkins D N, Chen J K, Cooper M K, Taipale J, Olson J M, Beachy P A., Science. Aug. 30, 2002;297(5586):1559-61), basal cell carcinoma ("Identification of a small molecule inhibitor of the hedgehog signaling pathway: effects on basal cell carcinoma-like lesions", Williams J A, Guicherit O M, Zaharian B I, Xu Y, Chai L, Wichterle H, Kon C, Gatchalian C, Porter J A, Rubin L L, Wang F Y., Proc Natl Acad Sci USA. Apr. 15, 2003;100(8):4616-21; "Activating Smoothened mutations in sporadic basal-cell carcinoma", Xie J, Murone M, Luoh S M, Ryan A, Gu Q, Zhang C, Bonifas J M, Lam C W, Hynes M, Goddard A, Rosenthal A, Epstein E H Jr, de Sauvage F J., Nature. Jan. 1, 1998;391 (6662):90-2), pancreatic cancer ("Hedgehog is an early and late mediator of pancreatic cancer tumorigenesis", Thayer S P, di Magliano M P, Heiser P W, Nielsen C M, Roberts D J, Lauwers G Y, Qi Y P, Gysin S, Fernandez-del Castillo C, Yajnik V, Antoniu B, McMahon M, Warshaw A L, Hebrok M., Nature. Oct. 23, 2003; 425(6960):851-6; "Widespread requirement for Hedgehog ligand stimulation in growth of digestive tract tumours", Berman D M, Karhadkar S S, Maitra A, Montes De Oca R, Gerstenblith M R, Briggs K, Parker A R, Shimada Y, Eshleman J R, Watkins D N, Beachy P A., Nature. Oct. 23, 2003; 425 (6960):846-51), and small-cell lung cancer ("Hedgehog signaling within airway epithelial progenitors and in small-cell lung cancer", Watkins D N, Berman D M, Burkholder S G, Wang B, Beachy P A, Baylin S B., Nature. Mar. 20, 2003; 422(6929):313-7).

Hedgehog pathway inhibitors (e.g. cyclopamine) have been shown to be useful in the treatment of psoriasis ("Cyclopamine: inhibiting hedgehog in the treatment of psoriasis" Cutis, 2006, 78(3):185-8; Br. J. Dermatology, April 2006; 154(4):619-23, "Psoriatic skin expresses the transcription factor Gli1: possible contribution of decreased neurofibromin expression", Endo H, Momota Y, Oikawa A, Shinkai H.).

Malignant lymphoma (ML) involves the cells of the lymphatic system, and is the fifth most common cancer in the U.S. ML includes Hodgkin's disease, and non-Hodgkin's diseases which are a heterogeneous group of lymphoid proliferative diseases. Hodgkin's disease accounts for approximately 14% of all malignant lymphomas. The non-Hodgkin's lymphomas are a diverse group of malignancies that are predominately of B-cell origin. In the Working Formulation classification scheme, these lymphomas been divided into low-, intermediate-, and high-grade categories by virtue of their natural histories (see "The Non-Hodgkin's Lymphoma Pathologic Classification Project," Cancer 49:2112-2135, 1982). The low-grade lymphomas are indolent, with a median survival of 5 to 10 years (Horning and Rosenberg, N. Engl. J. Med. 311: 1471-1475, 1984). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

Multiple myeloma (MM) is malignant tumor composed of plasma cells of the type normally found in the bone marrow. These malignant plasma cells accumulate in bone marrow and typically produce monoclonal IgG or IgA molecules. The malignant plasma cells home to and expand in the bone marrow causing anemia and immunosuppression due to loss of normal hematopoiesis. Individuals suffering from multiple myeloma often experience anemia, osteolytic lesions, renal failure, hypercalcemia, and recurrent bacterial infections. MM represents the second most common hematopoietic malignancy.

The present invention is predicated in part on the discoveries by the present inventors that lymphoma and multiple myeloma diseases are dependent on the hedgehog (Hh) signaling pathway using lymphoma and plasmacytoma cells isolated from transgenic Eµ-Myc mice and Cdkn2a knockout mice, and discovering that hedgehog ligands mediate the interaction between stroma and lymphoma cells. The same was found for lymphoma and multiple myeloma samples isolated from patient samples from the bone (multiple myeloma) or from lymph nodes, bone marrow or spleens from non-Hodgkin's lymphoma (NHL) patients and also for chronic lymphocytic leukemia (CLL) samples. In addition, it was found that inhibition of the Hh signaling pathway induces apoptosis of stroma dependent lymphoma cells, and that overexpression of hedgehog pathway members inhibit cyclopamine induced apoptosis of lymphoma cells in vitro. Further, the inventors found that treating mice with hedgehog pathway inhibitors abrogates lymphoma expansion in vivo. Finally, the inventors discovered that there is no expression of Gli3 in spleen B-cells and in the majority of cyclopamine responsive lymphomas, but a predominant expression in all cyclopamine resistant lymphomas.

These data indicate that Hh signaling provides an important anti-apoptotic signal for the initial steps of transformation by c-Myc and plays an important role for lymphoma maintenance. Thus, disruption of the Hh signaling pathway provides novel means for treating lymphomas (e.g., NHL), multiple myelomas, CLL and other hematopoietic malignancies. In addition, expression of Gli3 in lymphomas provides a negative predictive factor for responsiveness to Hh inhibition and an important means for patient stratification.

In accordance with these discoveries, the invention provides methods for inhibiting growth of tumor cells, e.g., lymphoma and myeloma cells. The invention provides methods and compositions to treat lymphoma or myeloma in a subject by inhibiting growth of tumor cells. The methods are also useful to prevent tumorigenesis in a subject. Some of the methods are directed to treating lymphomas which do not have significant expression of Gli3 relative to spleen B cells. The methods involve administering to the subject in need of treatment a pharmaceutical composition that contains an antagonizing agent of Hh signaling (e.g., a compound of Formula I). Compound of the invention down-regulate cellular level or inhibit a biological activity of an Hh signaling pathway member.

This invention provides methods of prophylactic or therapeutic treatment of cancers of the blood and lymphatic systems, including lymphomas, leukemia, and myelomas. The methods employ an antagonist of hedgehog signaling pathway to inhibit growth and proliferation of lymphoma cells, leukemia cells, or myeloma cells. Lymphoma is malignant tumor of lymphoblasts derived from B lymphocytes. Myeloma is a malignant tumor composed of plasma cells of the type normally found in the bone marrow. Leukemia is an acute or chronic disease that involves the blood forming organs. NHLs are characterized by an abnormal increase in the number of leucocytes in the tissues of the body with or without a corresponding increase of those in the circulating blood and are classified according to the type of leucocyte most prominently involved.

By way of example, subjects suffering from or at risk of development of lymphoma (e.g., e.g., B-cell lymphoma, plasmoblastoma, plasmacytoma or CLL) can be treated with methods of the invention. Preferably, the subject is a human being. The methods entail administering to the subject a pharmaceutical composition containing an effective amount of a compound of Formula I to inhibit the hedgehog signaling pathway. The subject can be one who is diagnosed with lymphoma, with or without metastasis, at any stage of the disease (e.g., stage I to IV, Ann Arbor Staging System). Lymphomas suitable for treatment with methods of the invention include but are not limited to Hodgkin's disease and non-Hodgkin's disease. Hodgkin's disease is a human malignant disorder of lymph tissue (lymphoma) that appears to originate in a particular lymph node and later spreads to the spleen, liver and bone marrow. It occurs mostly in individuals between the ages of 15 and 35. It is characterized by progressive, painless enlargement of the lymph nodes, spleen and general lymph tissue. Classic Hodgkin's disease is divided into four subtypes: (1) nodular sclerosis Hodgkin's disease (NSHD); (2) mixed cellularity Hodgkin's disease (MCHD); (3) lymphocyte depletion Hodgkin's disease (LDHD); and (4) lymphocyte-rich classic Hodgkin's disease (cLRHD).

In some preferred embodiments, the present methods are used to treat non-Hodgkin's Lymphoma (NHL). Non-Hodgkin's disease is also called lymphosarcoma and refers to a group of lymphomas which differ in important ways from Hodgkin's disease and are classified according to the microscopic appearance of the cancer cells. Non-Hodgkin's lymphoma includes but is not limited to (1) slow-growing lymphomas and lymphoid leukemia (e.g., chronic lymphocytic leukemia, small lymphocytic leukemia, lymphoplasmacytoid lymphoma, follicle center lymphoma, follicular small cleaved cell, follicular mixed cell, marginal zone B-cell lymphoma, hairy cell leukemia, plasmacytoma, myeloma, large granular lymphocyte leukemia, mycosis fungoides, szary syndrome); (2) moderately aggressive lymphomas and lymphoid leukemia (e.g., prolymphocytic leukemia, mantle cell lymphoma, follicle center lymphoma, follicular small cleaved cell, follicle center lymphoma, chronic lymphocytic leukemia/prolymphocytic leukemia, angiocentric lymphoma, angioimmunoblastic lymphoma); (3) aggressive lymphomas (e.g., large B-cell lymphoma, peripheral T-cell lymphomas, intestinal T-cell lymphoma, anaplastic large cell lymphoma); and (4) highly aggressive lymphomas and lymphoid leukemia (e.g., B-cell precursor B-lymphoblastic leukemia/lymphoma, Burkitt's lymphoma, high-grade B-cell lymphoma, Burkitt's-like T-cell precursor T-lymphoblastic leukemia/lymphoma). The methods of the present invention can be used for adult or childhood forms of lymphoma, as well as lymphomas at any stage, e.g., stage I, II, III, or IV. The methods described herein can also be employed to treat other forms of leukemia, e.g., acute lymphocytic leukemia (ALL).

Some of the therapeutic methods of the invention are particularly directed to treating lymphomas or myelomas which do not express Gli3. As disclosed in the Examples below, it was observed that, while Gli1 and Gli2 were expressed in all lymphomas, detectable Gli3 expression was present mainly in lymphomas which were resistant to Hh pathway inhibition by cyclopamine. There is no expression of Gli3 in normal spleen B-cells and in the majority of cyclopamine responsive lymphomas. Thus, prior to treatment with Hh antagonists, subjects with lymphomas can be first examined for expression of Gli3 in a lymphoma cell sample obtained from the subject. Gli3 expression level in the sample can be compared to Gli3 expression level in normal spleen B cells obtained from the subject. Gli3 expression levels in the lymphoma or myeloma samples and the control cells can be determined using methods well known in the art, e.g., as described in the Examples below. A likely responsiveness to treatment with Hh antagonists described herein is indicated by the lack of detectable Gli3 expression in the lymphoma or myeloma samples or an expression level that is not significantly higher (e.g., not more than 25%, 50%, or 100% higher) than Gli3 expression level in the normal B cell. Other than being an additional step of the therapeutic methods of the invention, the pre-screening for lack of Gli3 expression can be used independently as a method for patient stratification.

In addition to lymphomas, the methods and compositions described above are also suitable for the treatment of myelomas. Multiple myeloma is a fatal neoplasm characterized by an accumulation of a clone of plasma cells, frequently accompanied by the secretion of Ig chains. Bone marrow invasion by the tumor is associated with anemia, hypogammaglobinemia, and granulocytopenia with concomitant bacterial infections. An abnormal cytokine environment, principally raised IL-6 and IL-1$\beta$ levels, often results in increased osteoclasis leading to bone pain, fractures, and hypercalcemia. Despite aggressive chemotherapy and transplantation, multiple myeloma is a universally fatal plasma proliferative disorder.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions:

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with other therapies, such as radiation therapy, bone marrow transplantation or hormone therapy.

Compounds of the invention can be administered in therapeutically effective amounts in combination with one or more therapeutic agents (pharmaceutical combinations). For example, synergistic effects can occur with immunomodulatory, anti-inflammatory substances, other anti-tumor therapeutic agents, chemotherapeutic agents, ablation or other therapeutic hormones, antineoplastic agents and/or monoclonal antibodies useful against lymphomas or myelomas. Some of the well known anti-cancer drugs are described in the art, e.g., *Cancer Therapeutics: Experimental and Clinical Agents*, Teicher (Ed.), Humana Press (1$^{st}$ ed., 1997); and *Goodman and Gilman's The Pharmacological Basis of Therapeutics*, Hardman et al. (Eds.), McGraw-Hill Professional (10$^{th}$ ed., 2001). Examples of suitable anti-cancer drugs include 5-fluorouracil, vinblastine sulfate, estramustine phosphate, suramin and strontium-89. Examples of suitable chemotherapeutic agents include Asparaginase, Bleomycin Sulfate, Cisplatin, Cytarabine, Fludarabine Phosphate, Mitomycin and Streptozocin.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Schemes:

Reaction Scheme I:

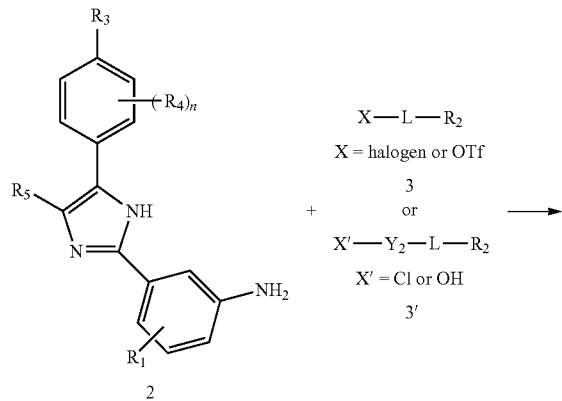

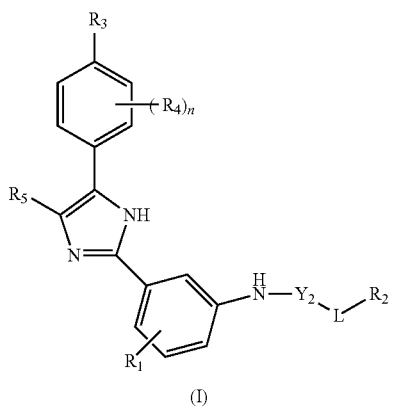

Reaction Scheme II

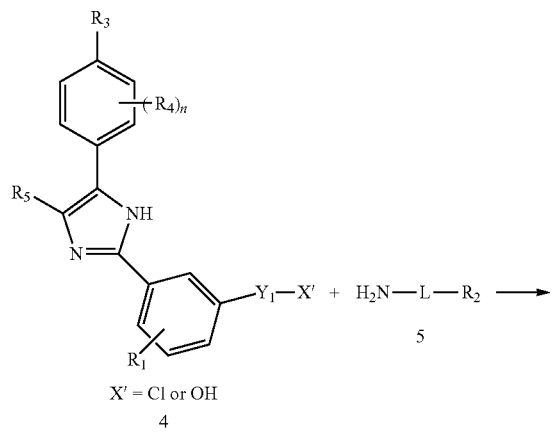

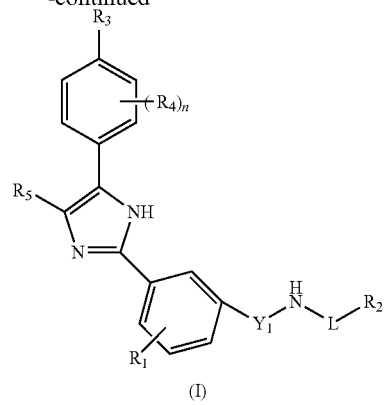

in which L, n, $Y_1$, $Y_2$, $R_1$, $R_2$, $R_3$, $R_4$ and $R_5$ are as defined for Formula I in the Summary of the Invention. In Reaction Scheme I, a compound of Formula I can be prepared by reacting a compound of formula 2 with a compound of formula 3 (or 3') in the presence or absence of suitable catalyst (e.g., palladium acetate or the like) and ligand (e.g., triphenylphosphine or the like) in a suitable solvent (e.g., dichloromethane, N,N-dimethylformide or the like), in a temperature range of about −20 to about 180° C. The reaction can take up to about 48 hours to complete. In Reaction Scheme II, a compound of Formula I can be prepared by reacting a compound of formula 4 with a compound of formula 5 in the presence of base (e.g., triethylamine or the like) in a suitable solvent (e.g., dichloromethane, N,N-dimethylformide or the like), in a temperature range of about −20 to about 100° C. The reaction can take up to about 48 hours to complete.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) those of reaction scheme I and II; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following example that illustrates the preparation of compounds of Formula I according to the invention.

Example 1

R-[4-Chloro-3-(5-phenyl-1H-imidazol-2-yl)-phenyl]-[6-(2-methyl-morpholin-4-yl)-isoquinolin-1-yl]-amine

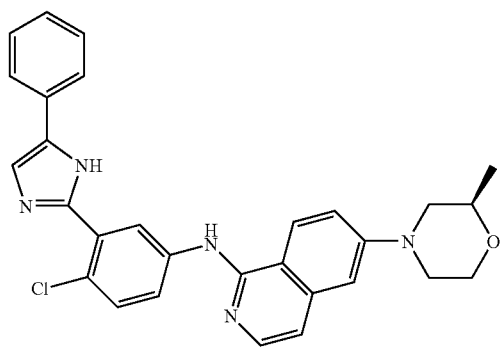

Step 1. R-2-methylmorpholine hydrochloride:

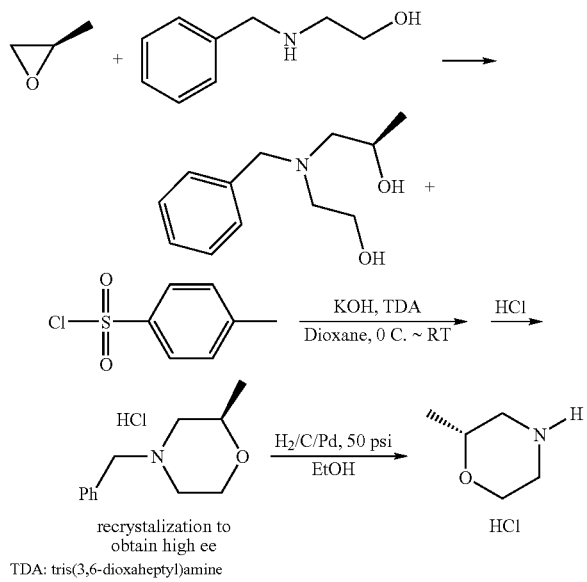

TDA: tris(3,6-dioxaheptyl)amine

N-Benzylethanolamine (9.06 g, 60 mmol) is stirred with (R)-(+)-propylene oxide (6.96 g, 99%, 120 mmol) in a sealed tube at 45° C. overnight. Evaporation of the excess of propylene oxide in vacuo gives the diol residue which is used directly for the next step.

The diol is dissolved in dioxane (60 mL, anhydrous). KOH (10.08 g, 180 mmol, powder) and tris(3,6-dioxaheptyl)amine (200 mg, 0.62 mmol) are added and the mixture is cooled to 0° C. after which tosyl chloride (12.58 g, 66 mmol, in 60 mL anhydrous dioxane) is added dropwise. The reaction mixture is allowed to stir at 0° C. for 45 minutes after which it is warmed to room temperature and stirred for an additional 4 hours. The reaction mixture is filtered (to remove insoluble material, KCl, KOH) and the filtrate is evaporated in vacuo. HCl (2 N, 200 mL) is added to the product and the resulting acidic aqueous solution is washed with ethyl acetate (150 mL×2), the solution cooled to 0° C. and neutralized by adding NaOH (pH monitored with pH paper). The product is then extracted with ethyl acetate. The organic phase is dried with $Na_2SO_4$ and then subjected to evaporation. The residue is chromatographed (5~20% ethyl acetate in DCM) to give the cyclized product.

The free base is converted to the HCl salt and recrystallized as follows: The free base obtained above is treated with HCl (2 M in ether, 50 mL) and subject to evaporation to yield the HCl salt. The salt (6.0 gram) is mixed with ethyl acetate (120 mL) and heated to reflux. EtOH is added dropwise cautiously until all solid is dissolved. It is then cooled to room temperature and kept in the refrigerator overnight. The precipitate obtained is filtered to give pure product.

A solution of the recrystallized salt (1.35 g, 5.94 mmole) in ethanol (30 mL) is hydrogenated over 10% Pd/C (0.20 g) under pressure (55 psi) at room temperature overnight. The mixture is filtered through celite (washed with EtOH) and the filtrate is evaporated to give an oil. Addition of ether and subsequent evaporation yields R-2-methylmorpholine hydrochloride as a solid. $^1$H NMR 400 MHz (MeOD) δ 4.08-4.01 (m, 1H), 3.90-3.78 (m, 2H), 3.35-3.21 (m, 2H), 3.17-3.06 (m, 1H), 2.86-2.77 (m, 1H), 1.22 (d, J=6.4 Hz, 3H).

Step 2. 4-Chloro-3-(5-phenyl-1H-imidazol-2-yl)-phenylamine

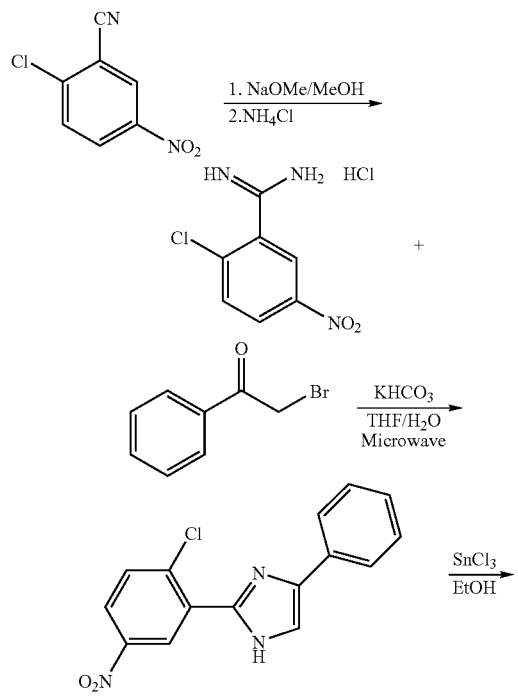

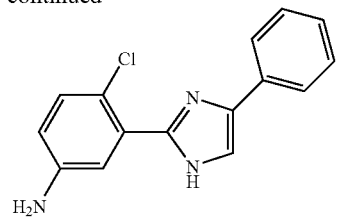

To a solution of 2-chloro-5-nitro-benzonitrile (913 mg, 5.00 mmol) in MeOH (10 ml) is added powdered sodium methoxide (135 mg, 2.50 mmol) at room temperature. The solution is stirred at 65° C. for one day. Then ammonium chloride (294 mg, 5.5 mmol) is added and the mixture is refluxed for another day. The mixture is cooled to room temperature and the solvent removed in vacuo to give the crude 2-chloro-5-nitro-benzamidine hydrochloride, which is dissolved in THF (20 ml) and water (2 ml). This solution is transferred to a quartz reaction vessel (20 ml) and 2-bromoacetophenone (800 mg, 4 mmol) and potassium hydrogencarbonate (1.5 g, 15 mmol) are added. The reaction vessel is then placed into the cavity of a microwave reactor (Emrys optimizer) and irradiated for 15 minutes at 120° C. After the mixture is cooled to room temperature, the solvent is evaporated and the residue is dissolved in EtOAc (50 ml). The organic solution is washed with water (30 ml) and brine (30 ml), dried over $MgSO_4$ and concentrated to give a crude dark oil, which is chromatographed (EtOAc/DCM=1/50) to give 2-(2-chloro-5-nitro-phenyl)-5-phenyl-1H-imidazole as a red solid.

A mixture of 2-(2-chloro-5-nitro-phenyl)-5-phenyl-1H-imidazole (430 mg, 1.43 mmol) and tin (II) chloride dihydrate (1.15 g, 5.02 mmol) in EtOH (15 ml) is heated at reflux for 3 hours. The mixture is cooled down to room temperature and the solvent is removed in vacuo. The residue obtained is treated with ethyl acetate (80 ml) and 1N NaOH solution is added until the pH is raised to around 12. The suspension is kept stirring for 10 minutes and then filtered through Celite cake. The solution obtained is concentrated to yield 4-chloro-3-(5-phenyl-1H-imidazol-2-yl)-phenylamine as a dark red foam-like solid.

Step 3. R-[4-Chloro-3-(5-phenyl-1H-imidazol-2-yl)-phenyl]-[6-(2-methyl-morpholin-4-yl)-isoquinolin-1-yl]-amine

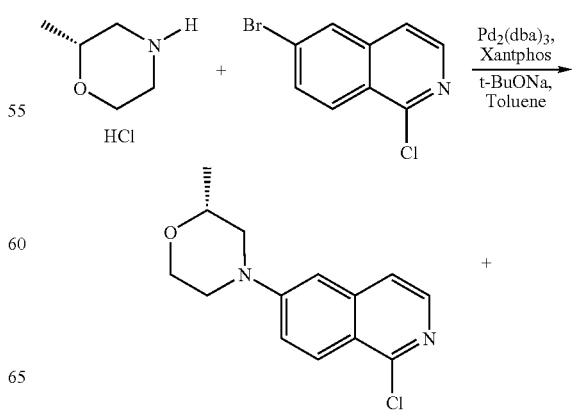

-continued

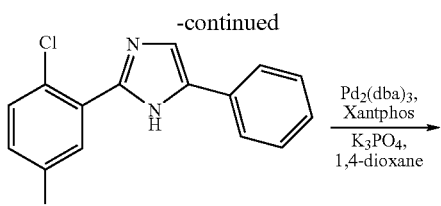

A mixture of 1-chloro-6-bromo-isoquinoline (242 mg, 1.00 mmol), which is prepared according to literature procedure [1], R-2-methylmorpholine hydrochloride (138 mg, 1.00 mmol), Pd$_2$(dba)$_3$ (18.3 mg, 0.02 mmol), xantphos 34.7 mg, 0.06 mmol), and t-BuONa (288 mg, 3.00 mmol) is subject to vacuo and backfilled with argon. Toluene (1.8 mL) is then added and the mixture was heated at 100° C. for 2 hours. After the reaction mixture is cooled to room temperature, it is directly loaded to a silica gel column and is chromatographed (DCM:EtOAC=100:3) to give 1-chloro-6-(2-R-methyl-morpholin-4-yl)-isoquinoline as an oil.

A mixture of 1-chloro-6-(2-R-methyl-morpholin-4-yl)-isoquinoline (26.3 mg, 0.1 mmol), 4-chloro-3-(5-phenyl-1H-imidazol-2-yl)-phenylamine (27.0 mg, 0.1 mmol), Pd$_2$(dba)$_3$ (9 mg, 0.01 mmol), xantphos 17 mg, 0.03 mmol), and K$_3$PO$_4$ (64 mg, 0.3 mmol) is subject to vacuo and backfilled with argon. 1,4-Dioxane (0.4 mL) is then added and the mixture is heated under stirring at 96° C. overnight. After it is cooled to room temperature, the reaction mixture is redistributed between ethyl acetate (30 mL) and saturated solution of ammonium chloride (30 mL). The organic phase is separated, dried with Na$_2$SO$_4$, and evaporated to give a residue which is subject to reverse-phase preparative LC-MS (acetonitrile/water/TFA gradient 10-90% CH$_3$CN in 7.5 min, Ultro 120 5 uM C18Q, 75×30 mmID). The collected water/MeCN solution of the TFA salt of the product is evaporated to remove the acetonitrile. A saturated aqueous solution of NaHCO$_3$ is added to raise the pH to 8~9. Then ethyl acetate is used to extract the product and the organic phase is dried with Na$_2$SO$_4$. Evaporation of the solvent yields the free-based R-[4-chloro-3-(5-phenyl-1H-imidazol-2-yl)-phenyl]-[6-(2-methyl-morpholin-4-yl)-isoquinolin-1-yl]-amine. $^1$H NMR 400 MHz (MeOD) δ 8.19 (d, J=9.2 Hz, 1H), 7.97-7.91 (m, 1H), 7.79-7.71 (m, 1H), 7.50 (s, 1H), 7.44 (d, J=8.8 Hz, 1H), 7.40-7.31 (m, 1H), 7.26-7.18 (m, 1H), 7.05-7.01 (m, 1H), 4.03-3.97 (m, 1H), 3.90-3.64 (m, 4H), 2.92-2.81 (m, 1H), 2.58-2.50 (m, 1H), 1.24 (d, J=6.0 Hz, 3H). LRMS m/z 496.3 (MH$^+$).

Example 2

R-[4-Chloro-3-(5-phenyl-1H-imidazol-2-yl)-phenyl]-[2-(2-methyl-morpholin-4-yl)-quinolin-5-yl]-amine

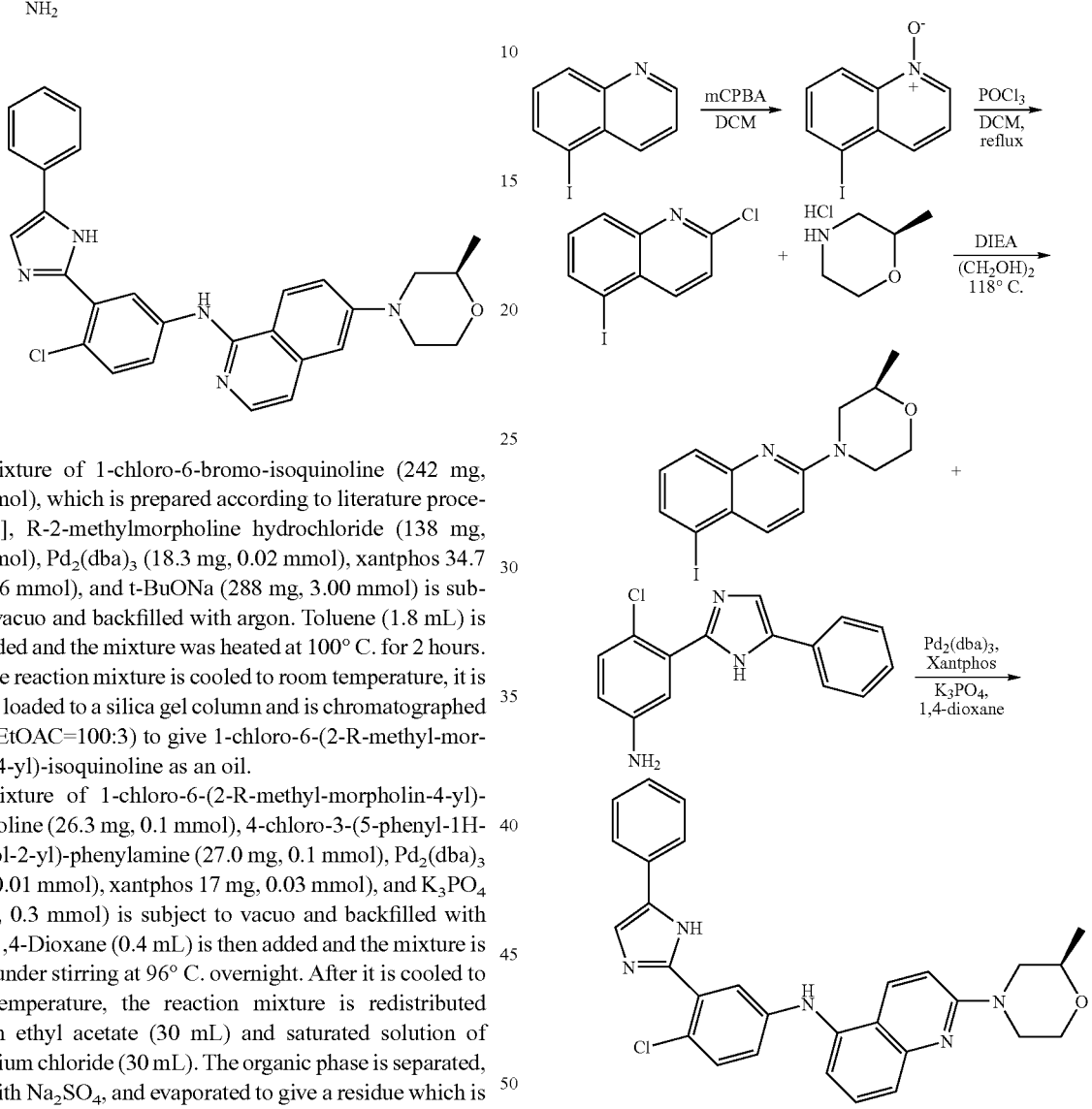

Step 1. To a solution of 5-iodoquinoline (1.02 g, 4.00 mmol) in dichloromethane (20 mL) at 0° C. is added 3-chloroperoxybenzoic acid (1.35 g, 77% maximum, ~1.5 eq.) and the mixture is stirred until reaction completed (monitored by LC-MS). Then the mixture is distributed between DCM (100 mL) and 10% solution of Na$_2$CO$_3$ (2×50 mL). The organic phase is further washed with HCl (1N, 50 mL) to extract the small amount of unoxidized quinoline derivatives and dried with Na$_2$SO$_4$.

Step 2. The N-oxide obtained is dissolved in anhydrous DCM (15 mL) and POCl$_3$ (920 mg, 1.5 eq.) is then added. The mixture is refluxed 1 hour and cooled to room temperature before it is poured into a solution of Na$_2$CO$_3$ (10% aqueous, 80 mL) at 0° C. After 30 minutes, it is diluted with DCM (50 mL) and the organic phase separated and dried with Na$_2$SO$_4$.

After evaporation, the residue is subject to column chromatography (silica gel, DCM:hexanes=1:1) to give the desired product 2-chloro-5-iodoquinoline (isomeric 4-chloro-iodoquinoline is detected and isolated).

Step 3. 2-Chloro-5-iodoquinoline (460 mg, 1.59 mmol) is then heated with R-2-methylmorpholine hydrochloride (262 mg, 1.90 mmol), diisopropylethylamine (328 mg, 2.54 mmol) with ethylene glycol (3.0 mL) as solvent at 118° C. overnight. The reaction mixture is distributed between ethyl acetate (60 mL) and a saturated solution of ammonium chloride (40 mL). The organic phase is washed once more with water (50 mL) and dried with Na$_2$SO$_4$. Evaporation gave a crude product (518 mg, 92%) which is used directly for next step.

Step 4. A mixture of the 5-iodo-2-(2-R-methyl-morpholin-4-yl)-quinoline (35.4 mg, 0.1 mmol), 4-chloro-3-(5-phenyl-1H-imidazol-2-yl)-phenylamine (27.0 mg, 0.1 mmol), Pd$_2$(dba)$_3$ (18 mg, 0.02 mmol), xantphos 34 mg, 0.03 mmol), and K$_3$PO$_4$ (64 mg, 0.3 mmol) is subject to vacuo and backfilled with argon. 1,4-Dioxane (0.4 mL) is then added and the mixture is heated under stirring at 96° C. overnight. After it is cooled to room temperature, the reaction mixture is redistributed between ethyl acetate (30 mL) and saturated solution of ammonium chloride (30 mL). The organic phase is separated, dried with Na$_2$SO$_4$, and evaporated to give a residue which is subject to reverse-phase preparative LC-MS (acetonitrile/water/TFA gradient 10-70% CH$_3$CN in 7.5 min, Ultro 120 5 uM C18Q, 75×30 mmID). The collected water/MeCN solution of the TFA salt of the product is evaporated to remove the acetonitrile. A saturated aqueous solution of NaHCO$_3$ is added to raise the pH to 8~9. Then ethyl acetate is used to extract the product and the organic phase is dried with Na$_2$SO$_4$. Evaporation of the solvent yields the free-based R-[4-chloro-3-(5-phenyl-1H-imidazol-2-yl)-phenyl]-[2-(2-methyl-morpholin-4-yl)-quinolin-5-yl]-amine. $^1$H NMR 400 MHz (MeOD) δ 8.25 (d, J=9.2 Hz, 1H), 7.75-7.70 (m, 2H), 7.50-6.95 (m, 11H), 4.38-4.33 (m, 1H), 4.30-4.24 (m, 1H), 4.04-3.96 (m, 1H), 3.72-3.65 (m, 2H), 3.07-2.98 (m, 1H), 2.72-2.64 (m, 1H), 1.25 (d, J=6.0 Hz, 3H). LRMS m/z 496.3 (MH$^+$).

Example 3

R-[4-Chloro-3-(5-phenyl-1H-imidazol-2-yl)-phenyl]-[2-(2-methyl-morpholin-4-yl)-[1,6]naphthyridin-5-yl]-amine

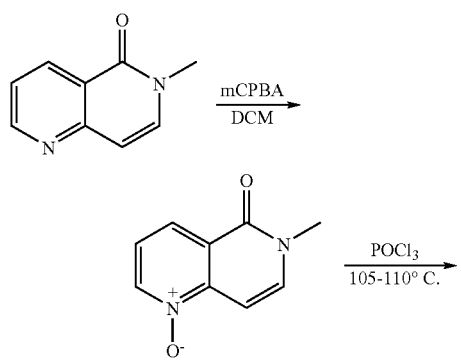

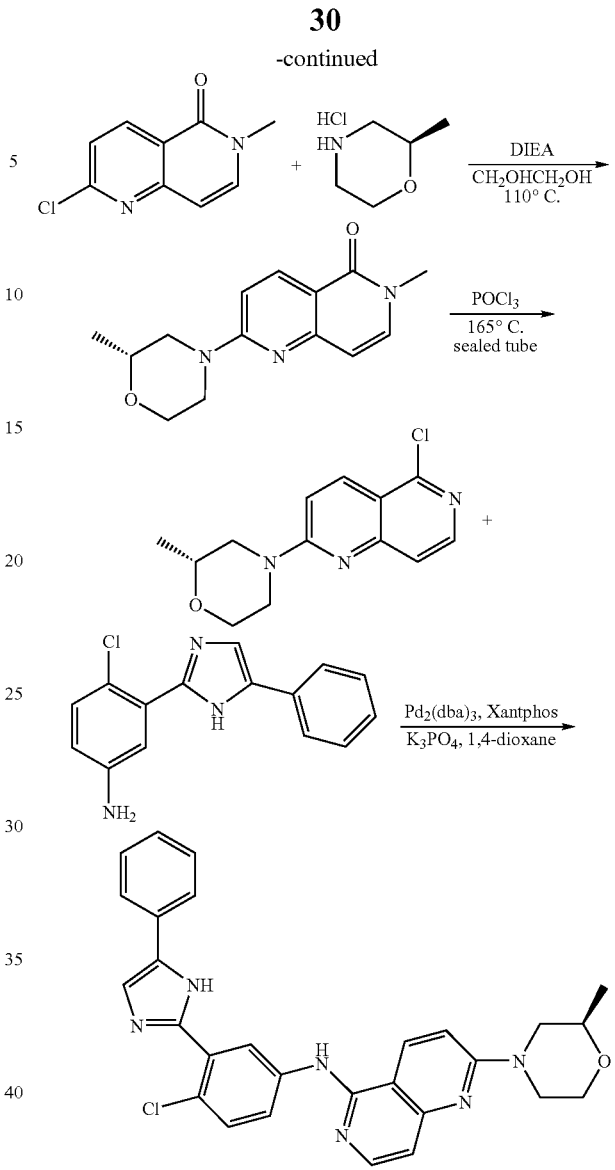

Step 1. To a solution of 6-methyl-6H-[1,6]naphthyridin-5-one (made according to literature [3], 2.40 g, 15.0 mmol) in DCM (50 mL) at 0° C. is added 3-chloroperoxybenzoic acid (5.50 g, 77% maximum, ~1.6 eq.). After 1 hour of stirring at 0° C., the reaction mixture is evaporated and the residue is dry-loaded to a short silica gel column and chromatographed (DCM:methonal=100:6) to give the 6-methyl-1-oxy-6H-[1,6]naphthyridin-5-one.

Step 2. The N-oxide obtained (2.20 g, 12.5 mmol) is heated with POCl$_3$ (8.0 mL) at 105-110° C. until all N-oxide solid is dissolved. It is then cooled to and maintained at 60° C. over the weekend. After it is cooled to room it is poured into a solution of Na$_2$CO$_3$ (10% aqueous, 700 mL) at 0° C. After 30 minutes, it is extracted with DCM (250 mL×2) and the organic phase separated and dried with Na$_2$SO$_4$. After evaporation, the residue is subject to column chromatography (silica gel, DCM:methanol=100:3) to give the desired 2-chloro-6-methyl-6H-[1,6]naphthyridin-5-one. The isomeric 4-chloro-6-methyl-6H-[1,6]naphthyridin-5-one is also obtained.

Step 3. 2-Chloro-6-methyl-6H-[1,6]naphthyridin-5-one (424 mg, 2.18 mmol) is then heated with R-2-methylmorpholine hydrochloride (316 mg, 2.30 mmol), diisopropylethylamine (664 mg, 2.5 eq.) and ethylene glycol (2.0 mL) as solvent at 110° C. overnight. The reaction mixture is distributed between ethyl acetate (60 mL) and a saturated solution of ammonium chloride (40 mL). The organic phase is dried with $Na_2SO_4$. The residue obtained after evaporation is chromatographed (DCM:methanol=100:1) to give R-6-methyl-2-(2-methyl-morpholin-4-yl)-6H-[1,6]naphthyridin-5-one.

Step 4. R-6-methyl-2-(2-methyl-morpholin-4-yl)-6H-[1,6]naphthyridin-5-one (172 mg, 0.66 mmol) is heated with $POCl_3$ (2.0 mL) in a sealed tube at 165° C. for 18 hours before it is cooled to room temperature and poured into a solution of $Na_2CO_3$ (10%, 100 mL) at 0° C. After 30 minutes, it is extracted with ethyl acetate (40 mL×2) and the combined organic phases are dried with $Na_2SO_4$ and subject to evaporation to give crude R-5-chloro-2-(2-methyl-morpholin-4-yl)-[1,6]-naphthyridine which is used directly in the next step.

Step 5. A mixture of the R-5-chloro-2-(2-methyl-morpholin-4-yl)-[1,6]naphthyridine (26.3 mg, 0.1 mmol), 4-chloro-3-(5-phenyl-1H-imidazol-2-yl)-phenylamine (27.0 mg, 0.1 mmol), $Pd_2(dba)_3$ (18 mg, 0.02 mmol), xantphos 34 mg, 0.03 mmol), and $K_3PO_4$ (64 mg, 0.3 mmol) is subject to vacuo and backfilled with argon. 1,4-Dioxane (0.4 mL) is then added and the mixture is heated under stirring at 96° C. overnight. After it is cooled to room temperature, the reaction mixture is redistributed between ethyl acetate (30 mL) and saturated solution of ammonium chloride (30 mL). The organic phase is separated, dried with $Na_2SO_4$, and evaporated to give a residue which is subject to reverse-phase preparative LC-MS (acetonitrile/water/TFA gradient 10-70% $CH_3CN$ in 7.5 min, Ultro 120 5 uM C18Q, 75×30 mmID). The collected water/MeCN solution of the TFA salt of the product is evaporated to remove the acetonitrile. A saturated aqueous solution of $NaHCO_3$ is added to raise the pH to 8~9. Then ethyl acetate is used to extract the product and the organic phase is dried with $Na_2SO_4$. Evaporation of the solvent yields the free-based R-[4-chloro-3-(5-phenyl-1H-imidazol-2-yl)-phenyl]-[2-(2-methyl-morpholin-4-yl)-[1,6]naphthyridin-5-yl]-amine. $^1H$ NMR 400 MHz ($CDCl_3$) δ 8.14-8.00 (m, 3H), 7.77-7.70 (m, 3H), 7.42-7.34 (m, 3H), 7.30-7.24 (m, 2H), 7.21 (d, J=8.8 Hz, 1H), 6.97 (d, J=6.0 Hz, 1H), 6.76 (d, J=9.2 Hz, 1H), 4.38-4.20 (m, 2H), 4.03-3.98 (m, 1H), 3.72-3.58 (m, 2H), 3.15-3.04 (m, 1H), 2.77-2.68 (m, 1H), 1.27 (d, J=6.0 Hz, 3H). LRMS m/z 497.2 ($MH^+$).

By repeating the procedures described in the above examples, using appropriate starting materials, the following compounds of Formula I, as identified in Table 1, are obtained.

TABLE 1

| Compound Number | Structure | Physical Data MS (m/z)/(M + 1) |
|---|---|---|
| 1 | 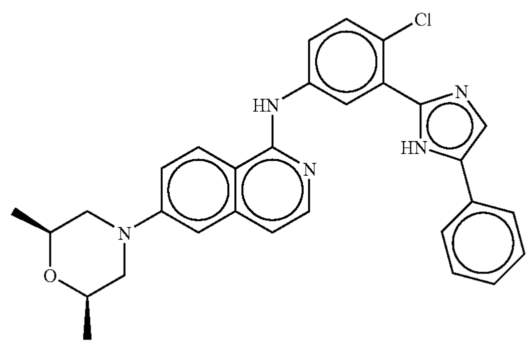 | 510.2 |
| 2 | 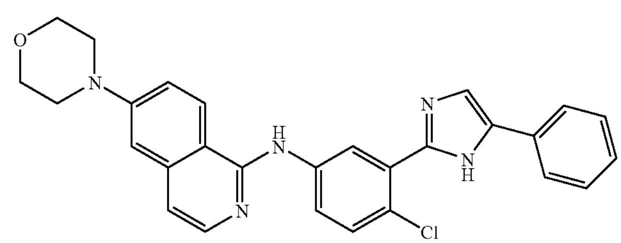 | 482.2 |
| 3 | 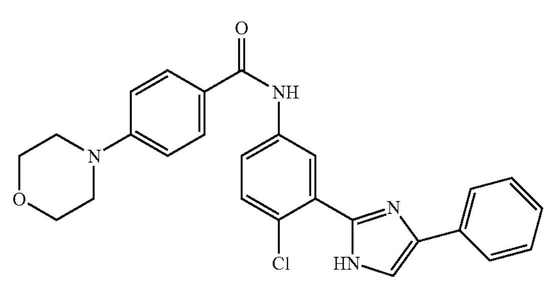 | 459.2 |

TABLE 1-continued

| Compound Number | Structure | Physical Data MS (m/z)/(M + 1) |
|---|---|---|
| 4 | 4-cyclohexyl-N-[4-chloro-3-(4-phenyl-1H-imidazol-2-yl)phenyl]benzamide | 456.2 |
| 5 | N-[4-chloro-3-(4-phenyl-1H-imidazol-2-yl)phenyl]-2-morpholinoquinolin-5-amine | 482.2 |
| 6 | N-[4-methyl-3-(4-phenyl-1H-imidazol-2-yl)phenyl]-6-(piperidin-1-yl)isoquinolin-1-amine | 460.2 |
| 7 | 6-(azepan-1-yl)-N-[4-methyl-3-(4-phenyl-1H-imidazol-2-yl)phenyl]isoquinolin-1-amine | 474.3 |
| 8 | 4-morpholino-N-[4-methyl-3-(4-phenyl-1H-imidazol-2-yl)phenyl]benzamide | 439.2 |
| 9 | 4-cyclohexyl-N-[4-methyl-3-(4-phenyl-1H-imidazol-2-yl)phenyl]benzamide | 436.2 |

TABLE 1-continued

| Compound Number | Structure | Physical Data MS (m/z)/(M + 1) |
| --- | --- | --- |
| 10 | 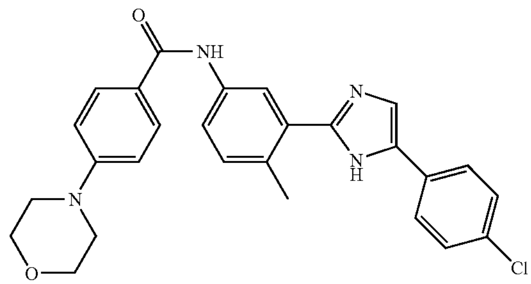 | 473.2 |
| 11 | 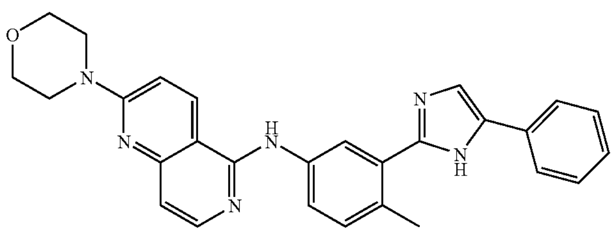 | 463.2 |
| 12 | 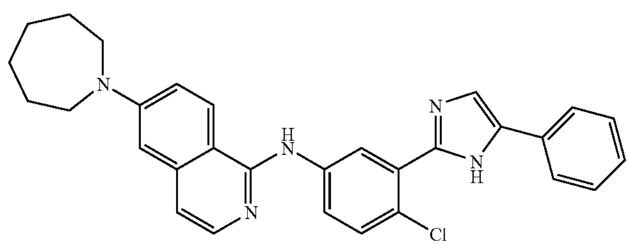 | 494.2 |
| 13 | 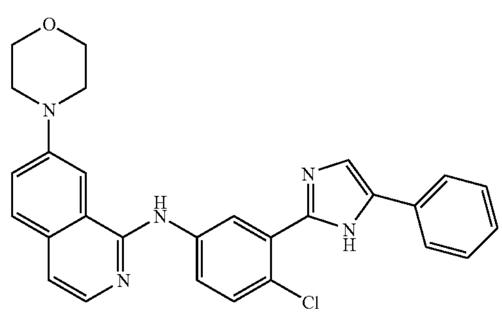 | 482.2 |
| 14 | 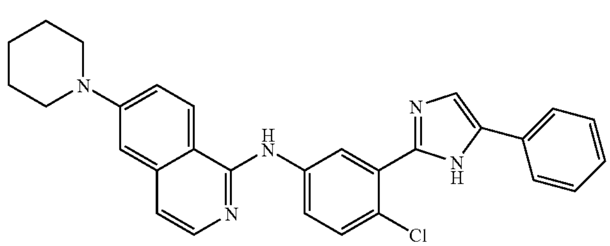 | 480.2 |

TABLE 1-continued

| Compound Number | Structure | Physical Data MS (m/z)/(M + 1) |
|---|---|---|
| 15 | 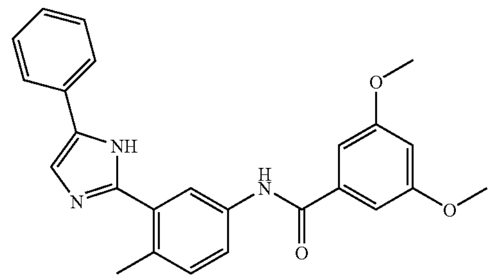 | 414.2 |
| 16 | 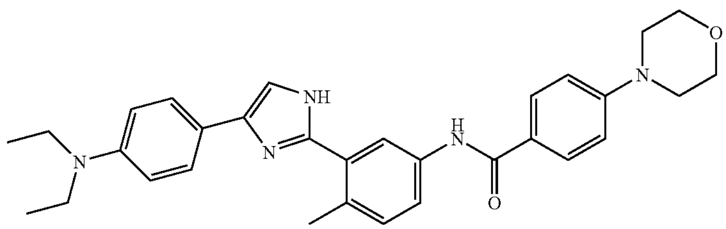 | 510.3 |
| 17 | 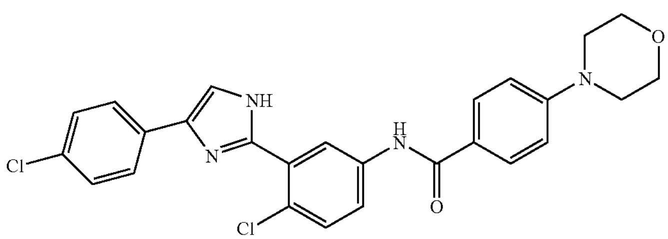 | 493.1 |
| 18 | 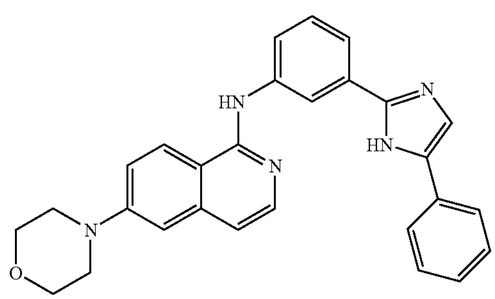 | 448.2 |
| 19 | 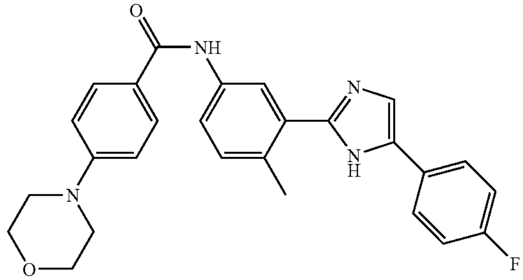 | 457.2 |

TABLE 1-continued
| Compound Number | Structure | Physical Data MS (m/z)/(M + 1) |
|---|---|---|
| 20 | 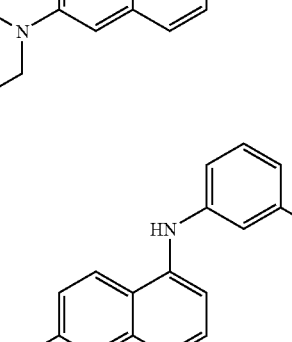 | 448.2 |
| 21 | 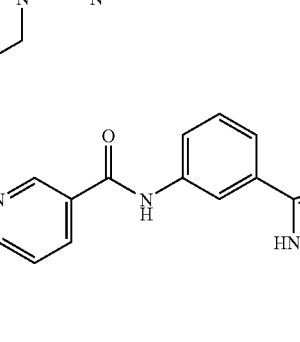 | 448.2 |
| 22 | 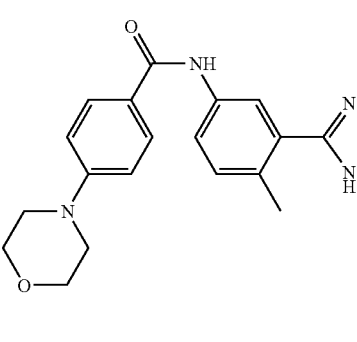 | 426.2 |
| 23 | 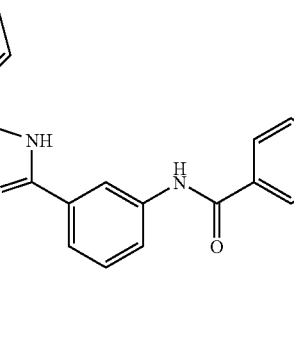 | 473.2 |
| 24 | 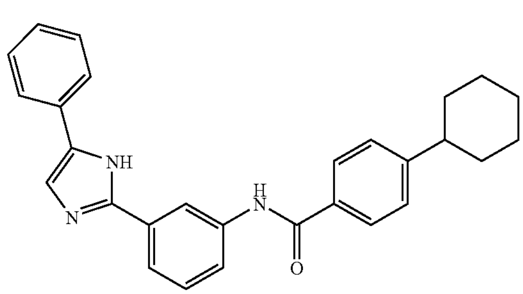 | 422.2 |

TABLE 1-continued
| Compound Number | Structure | Physical Data MS (m/z)/(M + 1) |
|---|---|---|
| 25 | 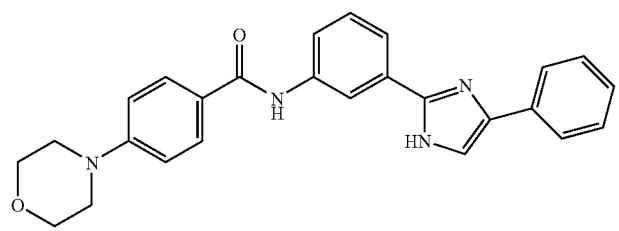 | 425.2 |
| 26 | 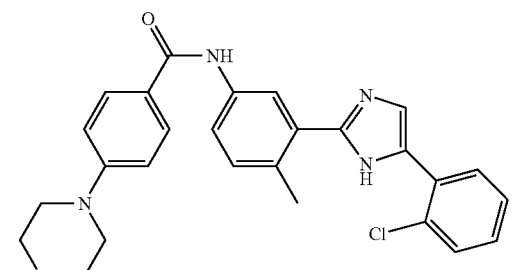 | 473.2 |
| 27 | 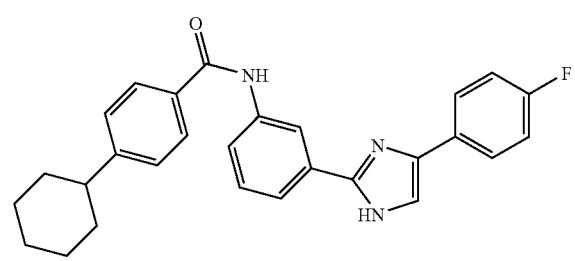 | 440.2 |
| 28 | 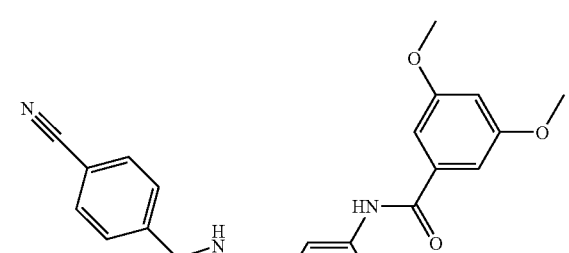 | 439.2 |
| 29 | 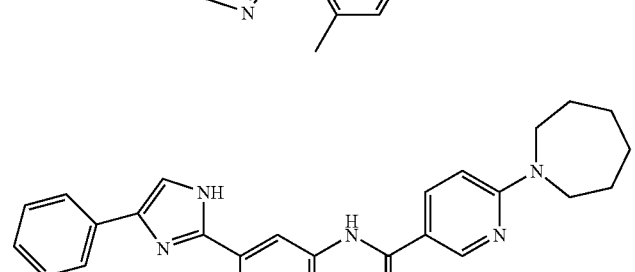 | 438.2 |

TABLE 1-continued
| Compound Number | Structure | Physical Data MS (m/z)/(M + 1) |
|---|---|---|
| 30 | 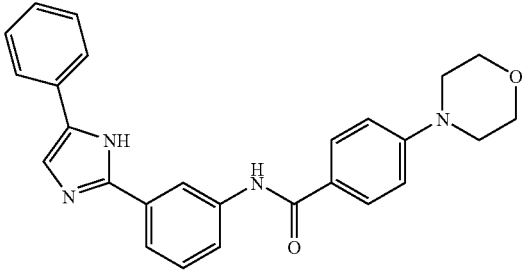 | 425.2 |
| 31 | 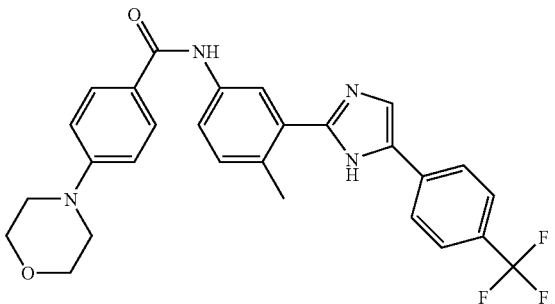 | 507.2 |
| 32 | 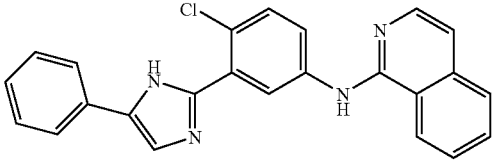 | 400.1 |
| 33 | 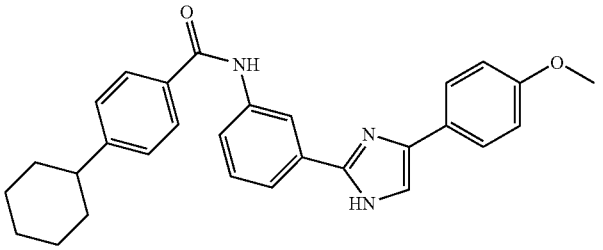 | 452.2 |
| 34 | 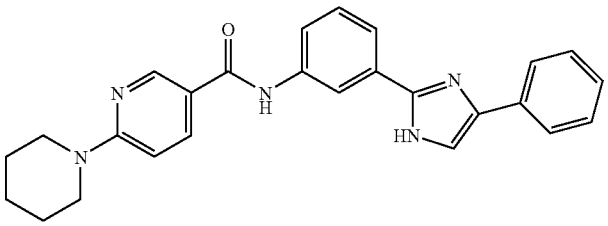 | 424.2 |
| 35 | 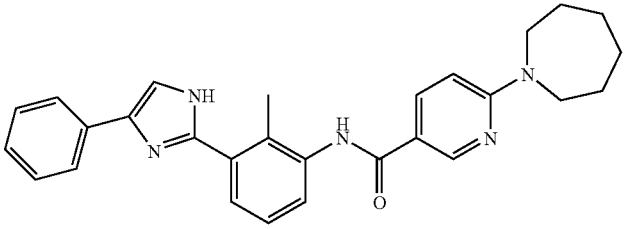 | 452.2 |

TABLE 1-continued

| Compound Number | Structure | Physical Data MS (m/z)/(M + 1) |
|---|---|---|
| 36 | 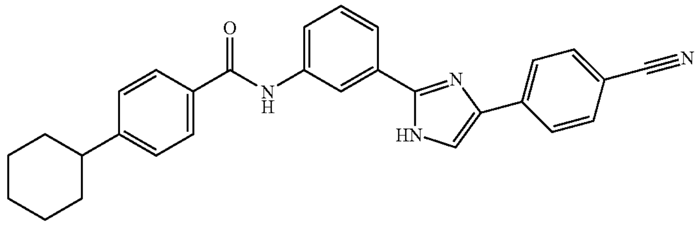 | 447.2 |
| 37 | 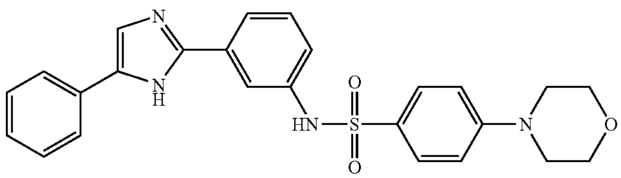 | 461.2 |
| 38 | 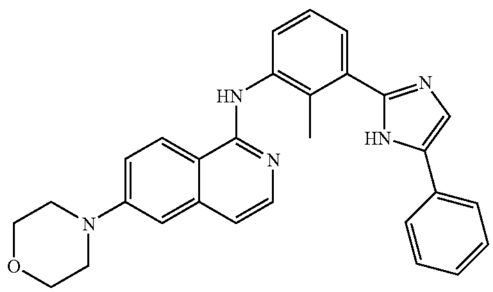 | 462.2 |
| 39 | 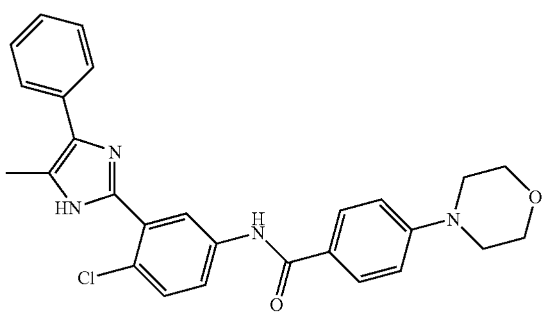 | 473.2 |
| 40 | 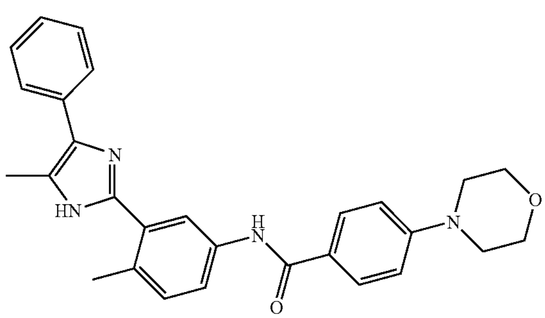 | 453.2 |

TABLE 1-continued
| Compound Number | Structure | Physical Data MS (m/z)/(M + 1) |
|---|---|---|
| 41 | 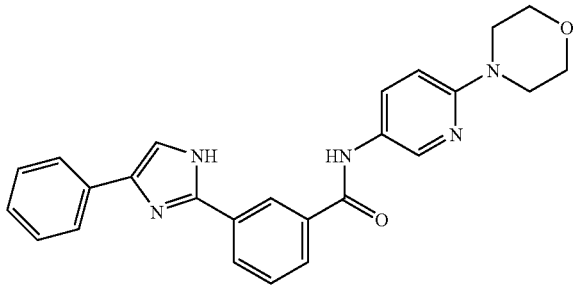 | 426.2 |
| 42 | 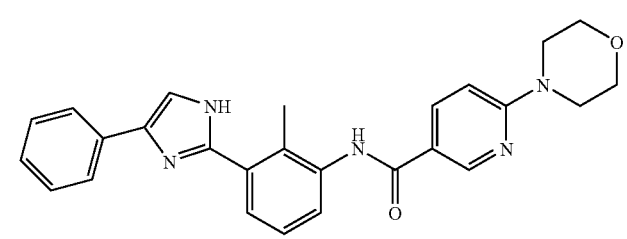 | 440.2 |
| 43 | 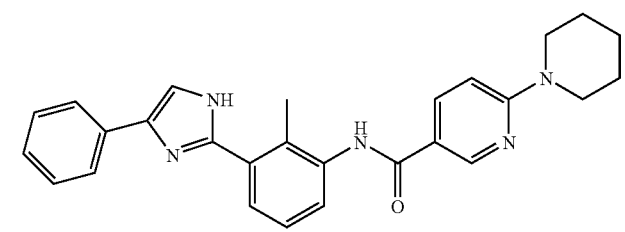 | 438.2 |
| 44 | 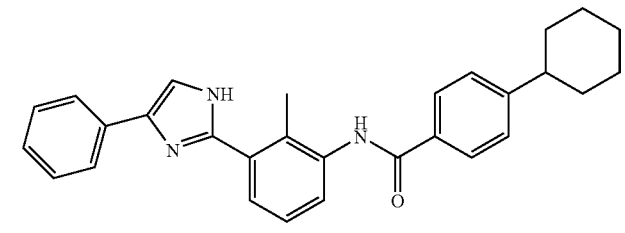 | 436.2 |
| 45 | 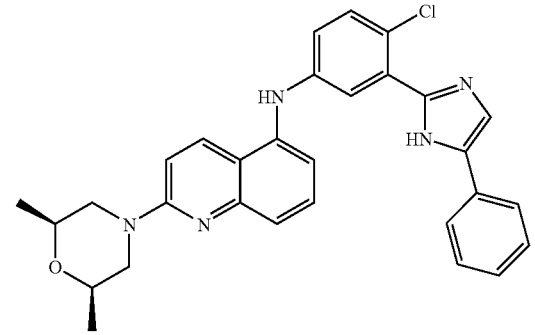 | 510.2 |

TABLE 1-continued

| Compound Number | Structure | Physical Data MS (m/z)/(M + 1) |
|---|---|---|
| 46 | 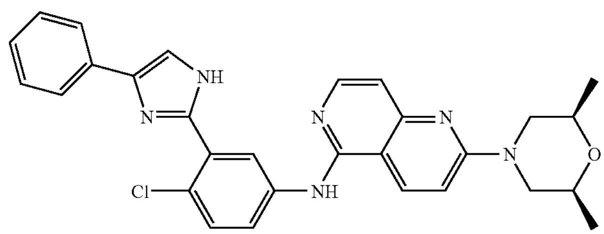 | 511.2 |
| 47 | 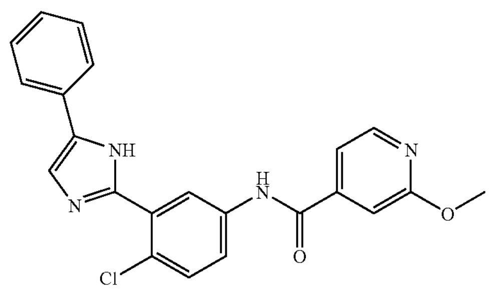 | 405.1 |
| 48 | 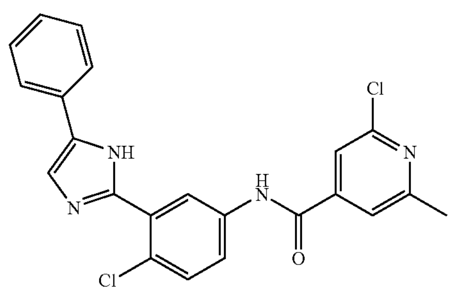 | 423.1 |
| 49 | 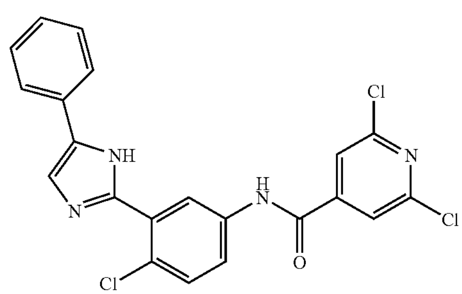 | 443.0 |
| 51 | 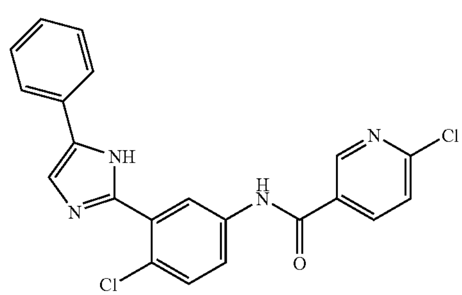 | 409.1 |

TABLE 1-continued

| Compound Number | Structure | Physical Data MS (m/z)/(M + 1) |
|---|---|---|
| 52 | 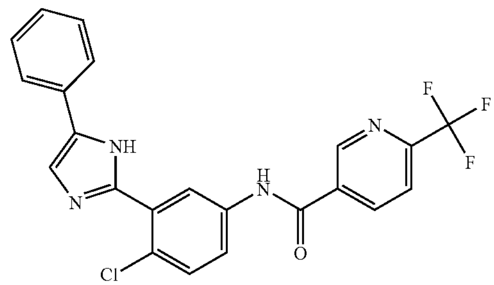 | 443.1 |
| 53 | 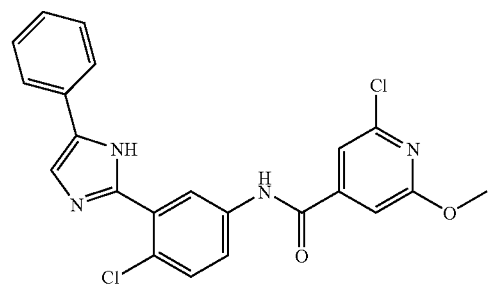 | 439.1 |
| 54 | 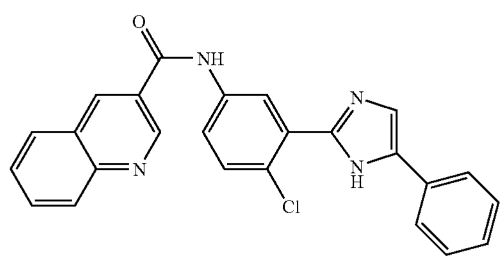 | 425.1 |
| 55 | 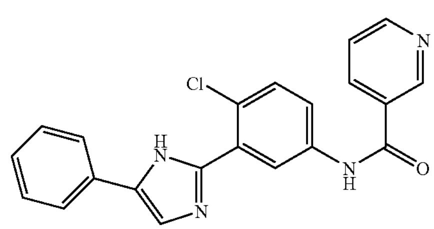 | 375.1 |
| 56 | 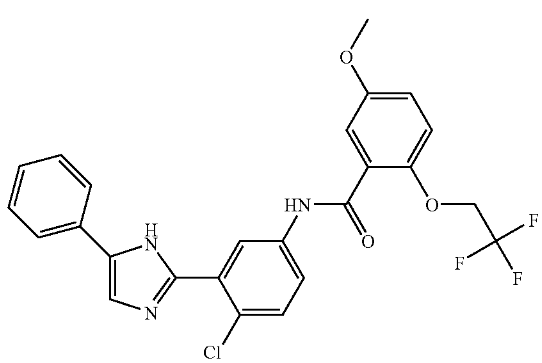 | 502.1 |

TABLE 1-continued

| Compound Number | Structure | Physical Data MS (m/z)/(M + 1) |
|---|---|---|
| 57 | 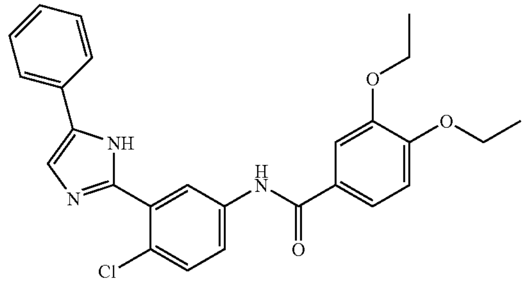 | 462.2 |
| 58 | 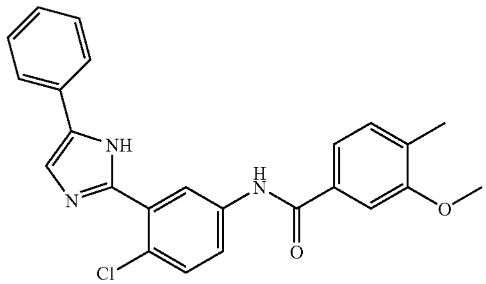 | 418.1 |
| 59 | 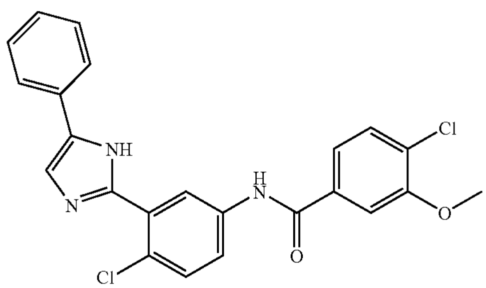 | 438.1 |
| 60 | 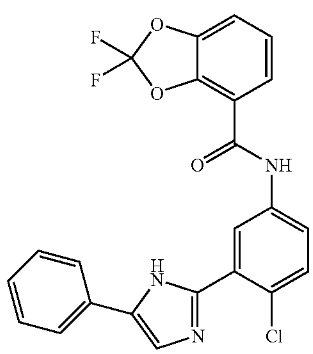 | 454.1 |
| 61 | 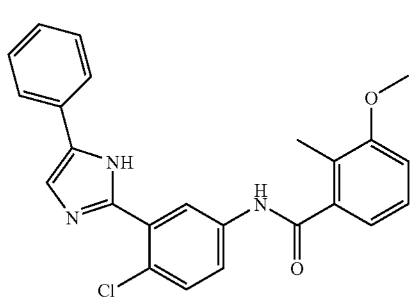 | 418.1 |

TABLE 1-continued
| Compound Number | Structure | Physical Data MS (m/z)/(M + 1) |
|---|---|---|
| 62 | 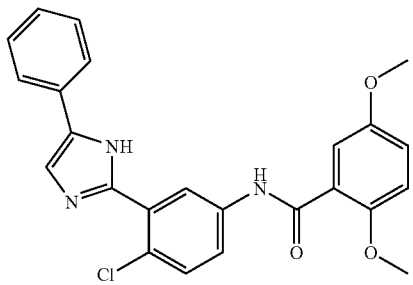 | 434.1 |
| 63 | 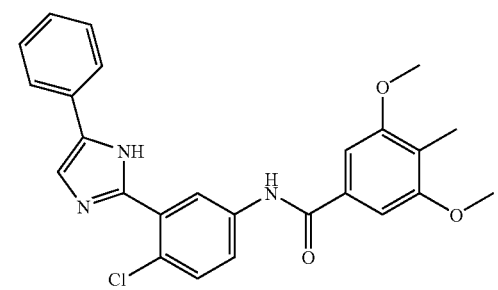 | 448.1 |
| 64 | 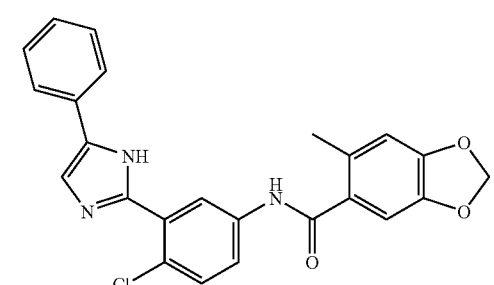 | 432.1 |
| 65 | 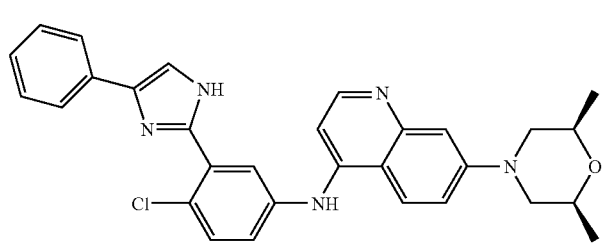 | 510.2 |
| 66 | 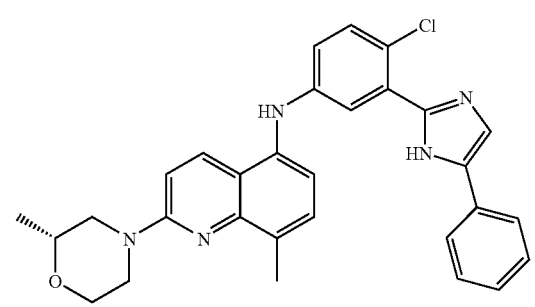 | 510.2 |

TABLE 1-continued

| Compound Number | Structure | Physical Data MS (m/z)/(M + 1) |
|---|---|---|
| 67 | 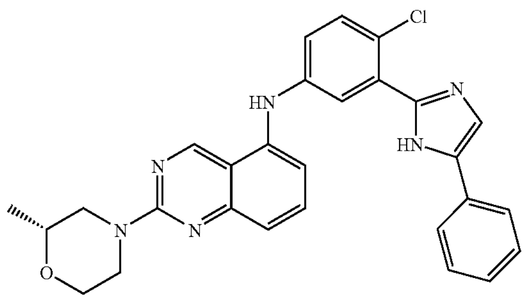 | |
| 68 | 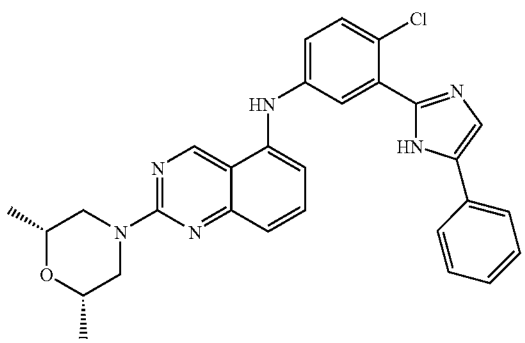 | |
| 69 | 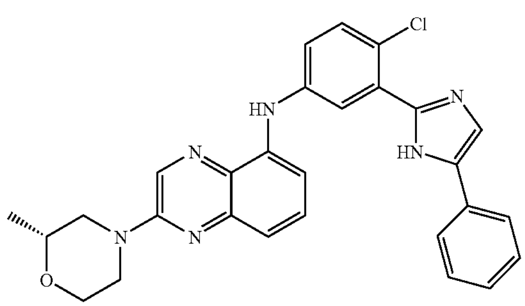 | |
| 70 | 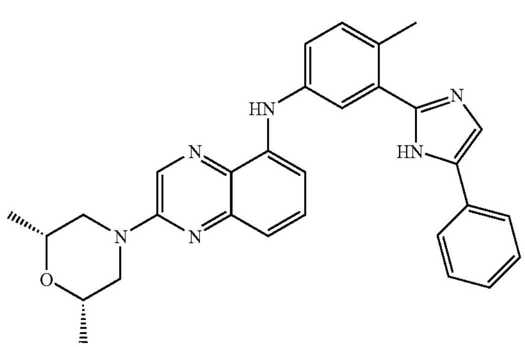 | 491.3 |

TABLE 1-continued

| Compound Number | Structure | Physical Data MS (m/z)/(M + 1) |
|---|---|---|
| 71 | 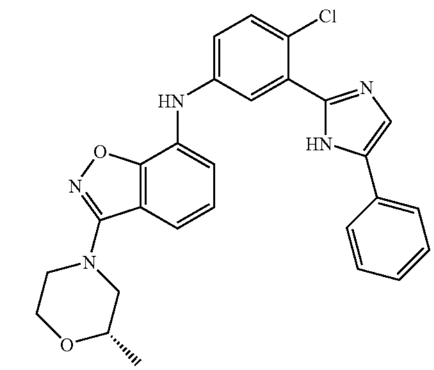 | |
| 72 | 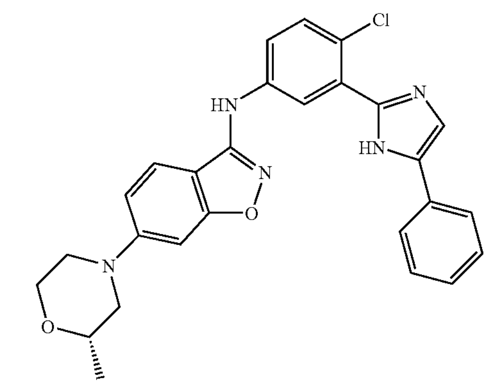 | |
| 73 | 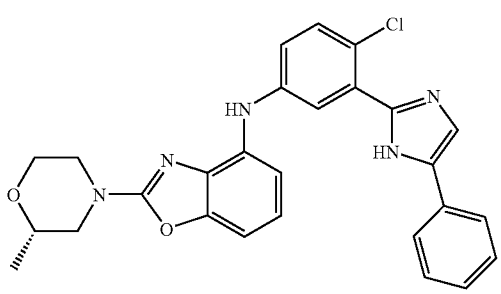 | |
| 74 | 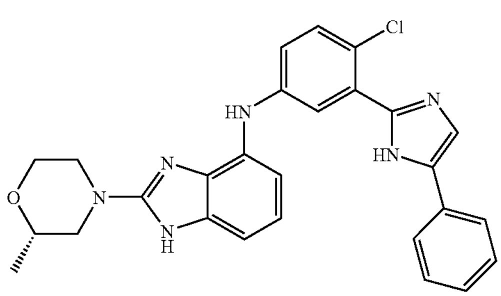 | |

TABLE 1-continued

| Compound Number | Structure | Physical Data MS (m/z)/(M + 1) |
|---|---|---|
| 75 | 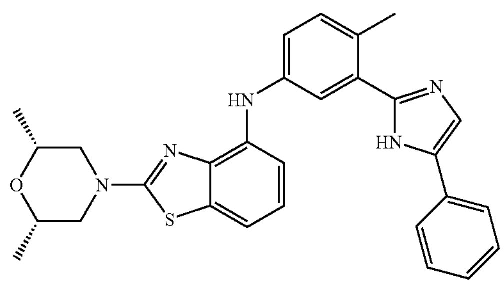 | 496.2 |
| 76 | 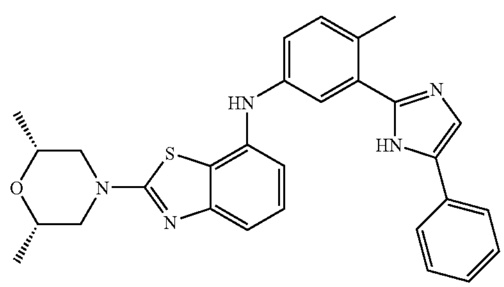 | 496.2 |
| 77 | 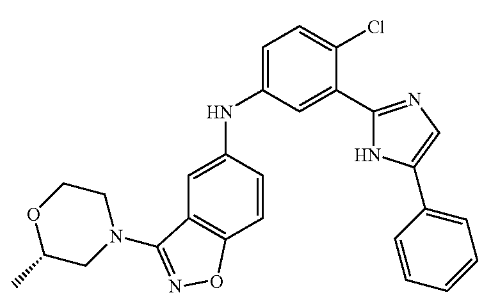 | |
| 78 | 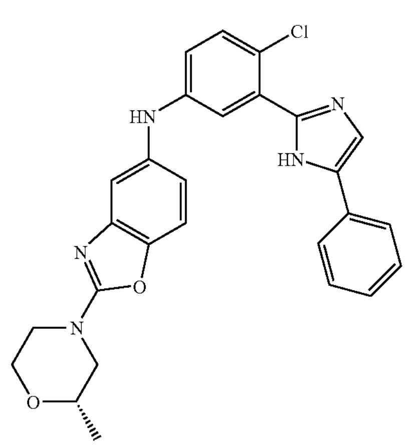 | |

TABLE 1-continued

| Compound Number | Structure | Physical Data MS (m/z)/(M + 1) |
|---|---|---|
| 79 | 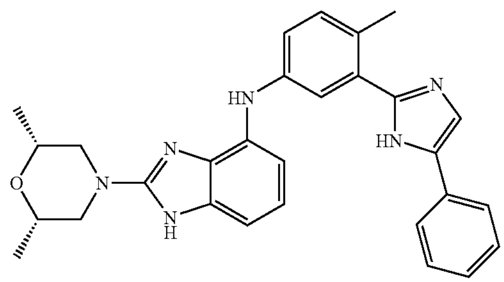 | 479.3 |
| 80 | 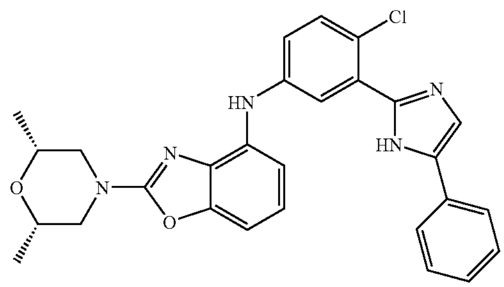 | 500.2 |
| 81 | 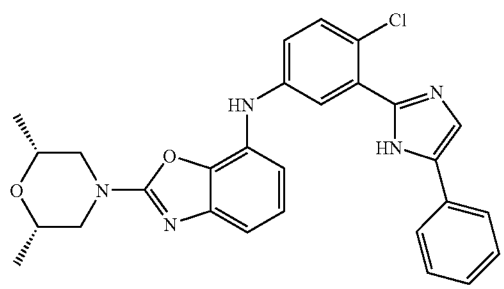 | 500.2 |
| 82 | 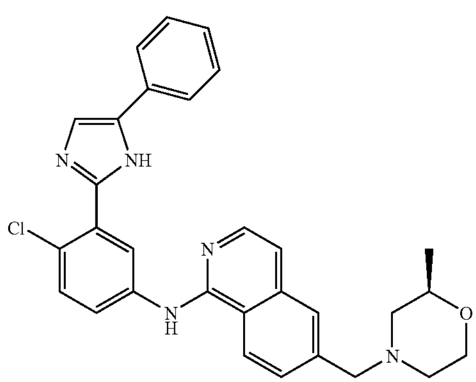 | 510.2 |

TABLE 1-continued

| Compound Number | Structure | Physical Data MS (m/z)/(M + 1) |
|---|---|---|
| 83 | 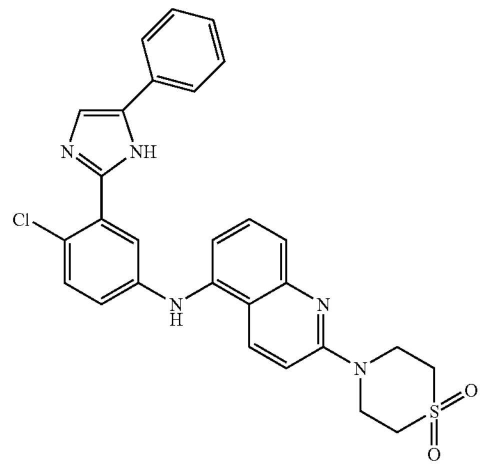 | 530.1 |
| 84 | 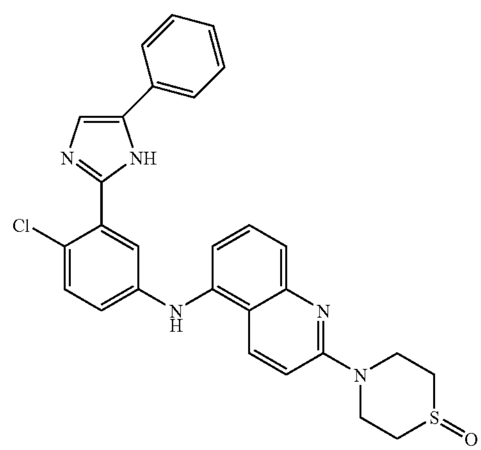 | 514.1 |
| 85 | 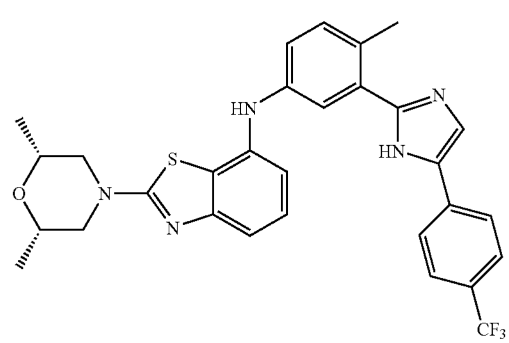 | 564.2 |

TABLE 1-continued

| Compound Number | Structure | Physical Data MS (m/z)/(M + 1) |
|---|---|---|
| 86 | 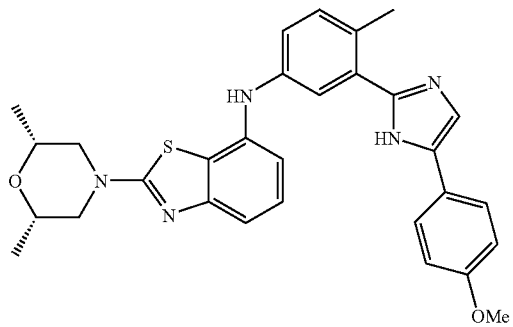 | 526.2 |
| 87 | 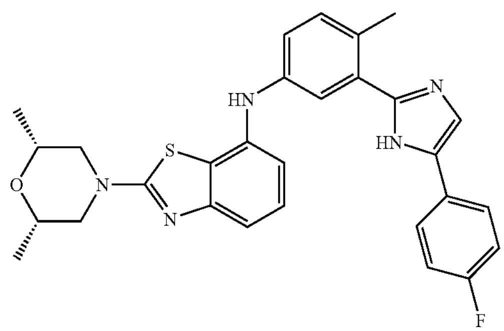 | 514.2 |
| 88 | 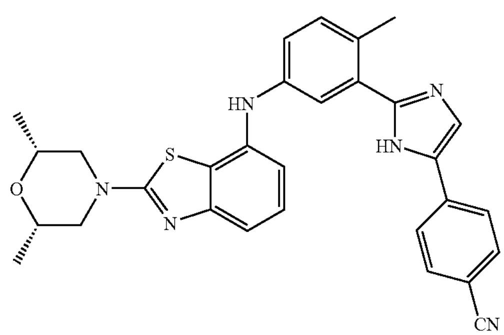 | 521.2 |
| 89 | 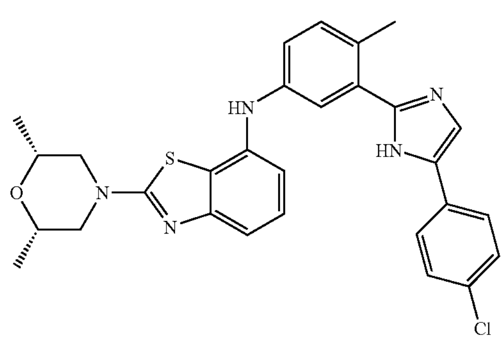 | 530.2 |

TABLE 1-continued

| Compound Number | Structure | Physical Data MS (m/z)/(M + 1) |
|---|---|---|
| 90 | 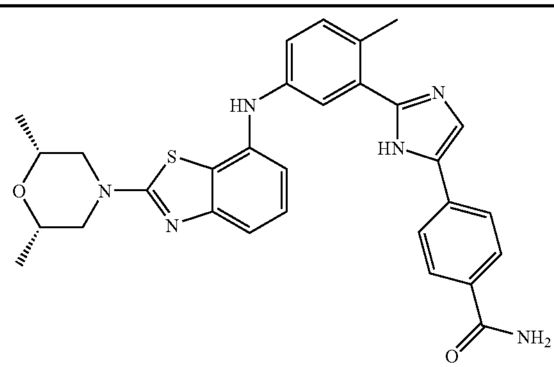 | 539.2 |
| 91 | 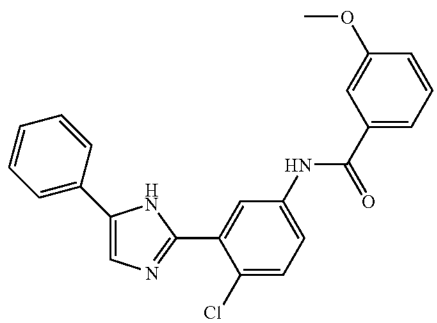 | 404.1 |
| 92 | 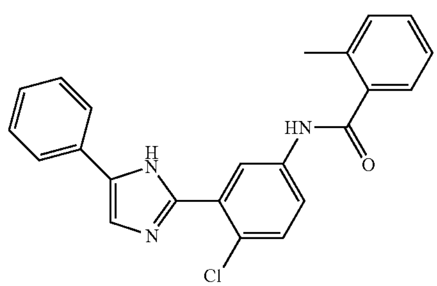 | 388.1 |
| 93 | 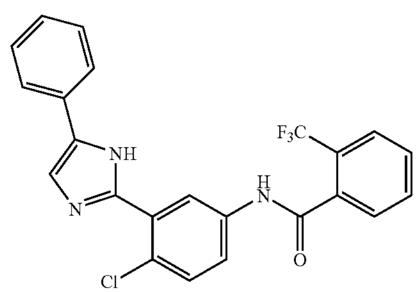 | 442.1 |
| 94 | 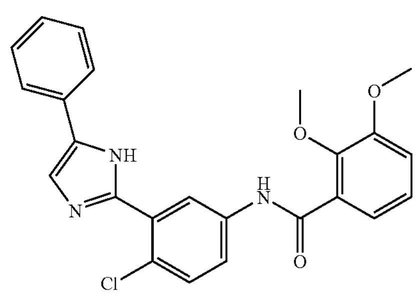 | 434.1 |

TABLE 1-continued

| Compound Number | Structure | Physical Data MS (m/z)/(M + 1) |
| --- | --- | --- |
| 95 | 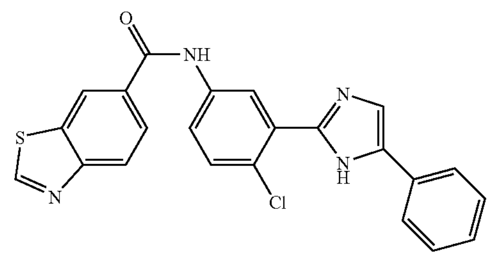 | 431.1 |
| 96 | 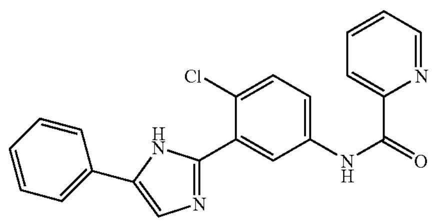 | 375.1 |
| 97 | 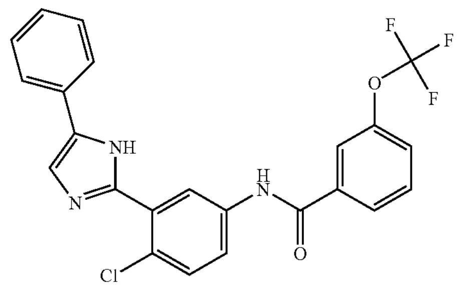 | 458.1 |
| 98 | 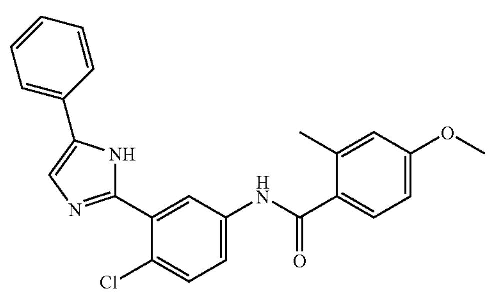 | 418.1 |
| 99 | 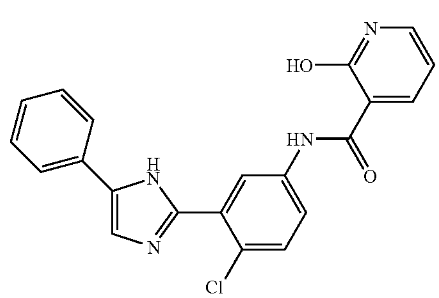 | 391.1 |

TABLE 1-continued

| Compound Number | Structure | Physical Data MS (m/z)/(M + 1) |
|---|---|---|
| 100 | 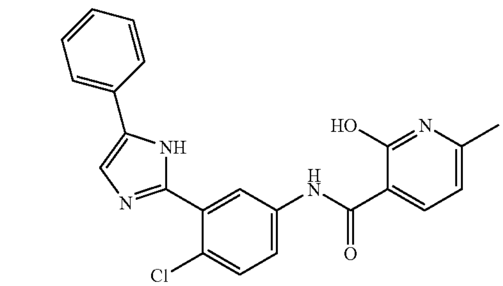 | 405.1 |
| 101 | 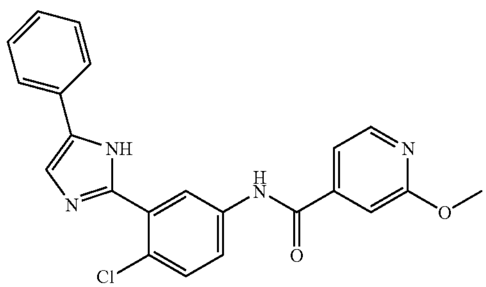 | 405.1 |
| 102 | 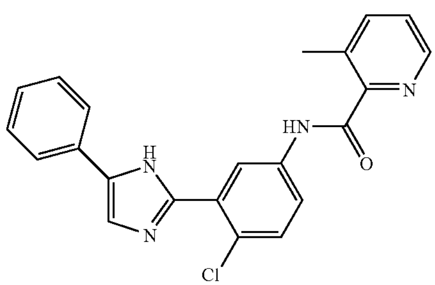 | 389.1 |
| 103 | 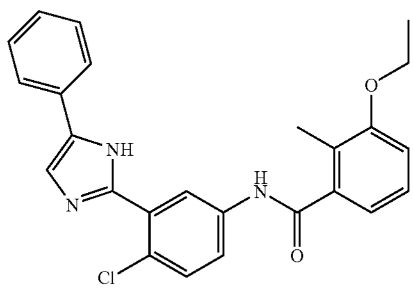 | 432.1 |
| 104 | 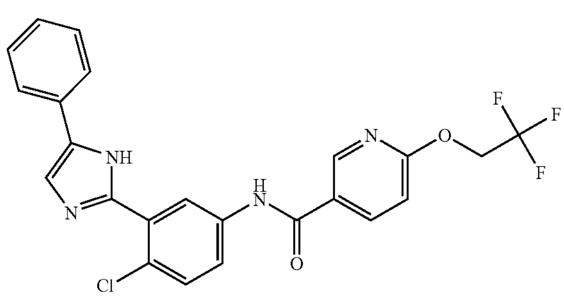 | 473.1 |

TABLE 1-continued

| Compound Number | Structure | Physical Data MS (m/z)/(M + 1) |
|---|---|---|
| 105 | 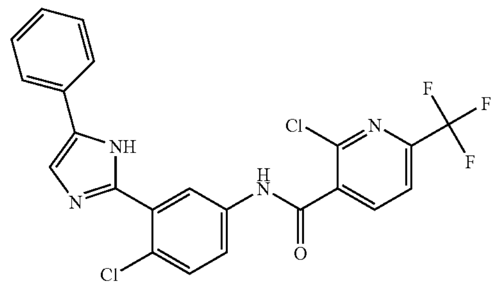 | 477.0 |
| 106 | 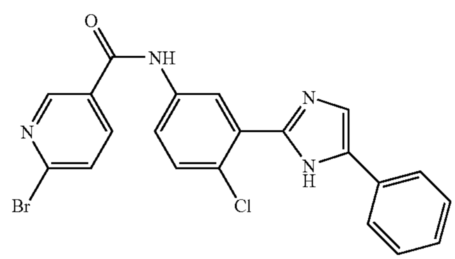 | 453.0 |
| 107 | 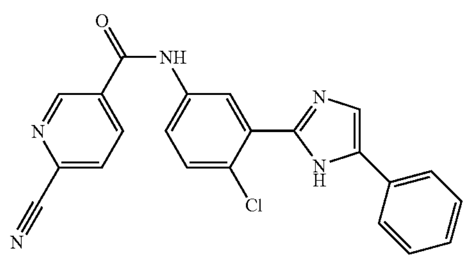 | 400.1 |
| 108 | 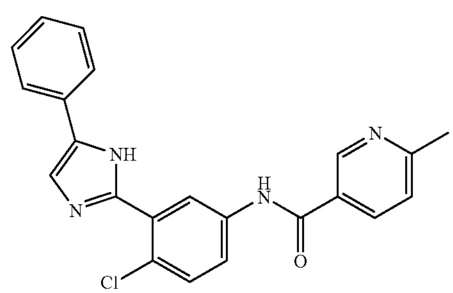 | 389.1 |
| 109 | 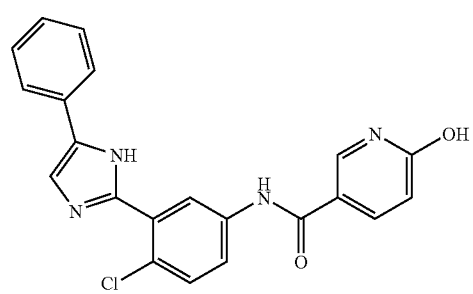 | 391.1 |

TABLE 1-continued

| Compound Number | Structure | Physical Data MS (m/z)/(M + 1) |
|---|---|---|
| 110 | 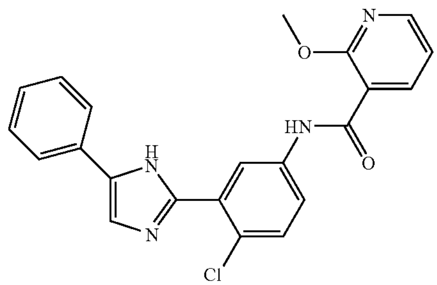 | 405.1 |
| 111 | 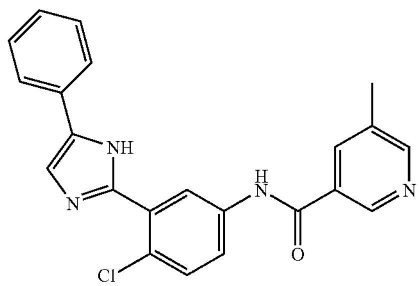 | 389.1 |
| 112 | 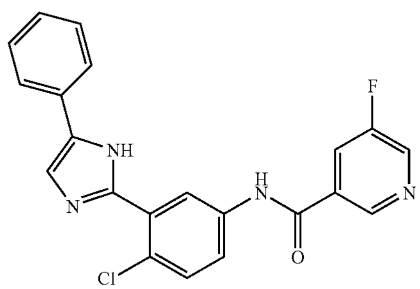 | 393.1 |
| 113 | 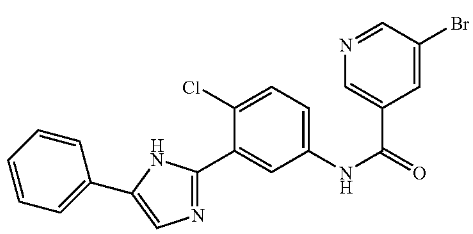 | 453.0 |
| 114 | 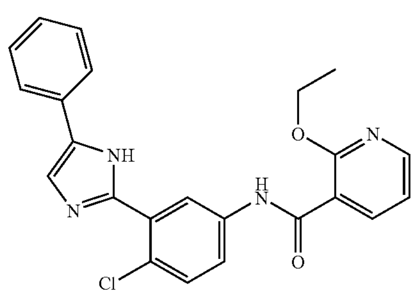 | 419.1 |

TABLE 1-continued

| Compound Number | Structure | Physical Data MS (m/z)/(M + 1) |
|---|---|---|
| 115 | 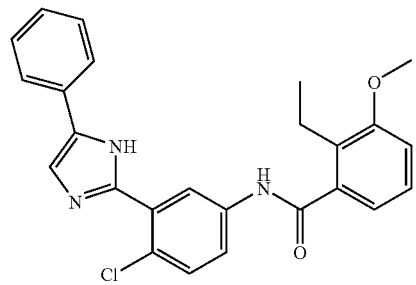 | 432.1 |
| 116 | 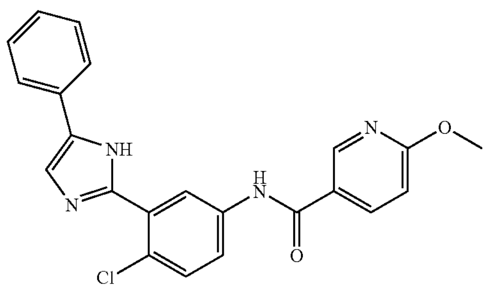 | 405.1 |
| 117 | 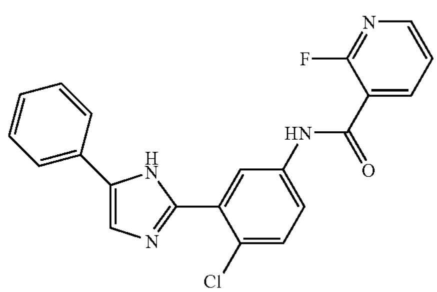 | 393.1 |
| 118 | 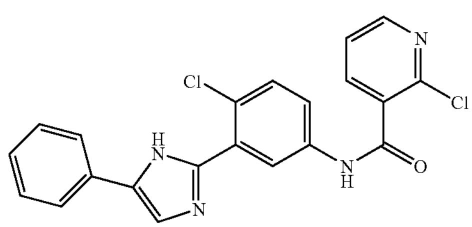 | 409.1 |
| 119 | 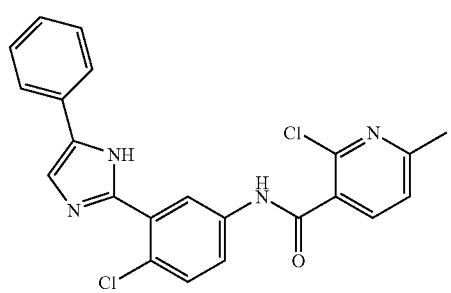 | 423.1 |

TABLE 1-continued

| Compound Number | Structure | Physical Data MS (m/z)/(M + 1) |
|---|---|---|
| 120 | 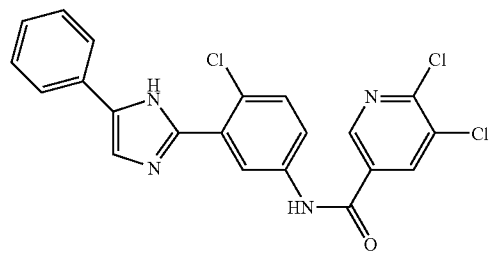 | 443.0 |
| 121 | 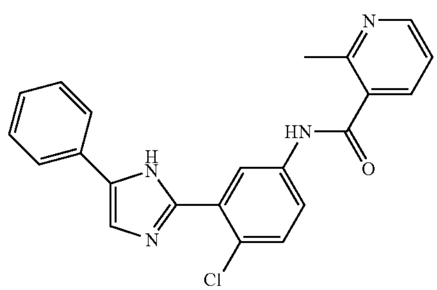 | 389.1 |
| 122 | 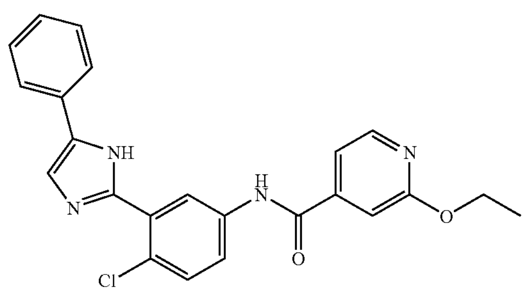 | 419.1 |
| 123 | 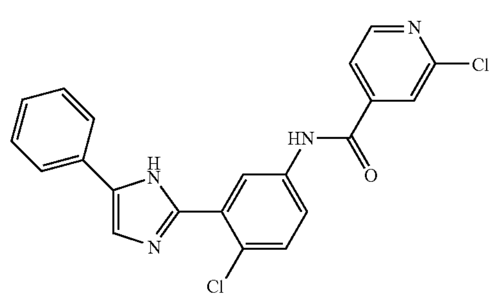 | 409.0 |
| 124 | 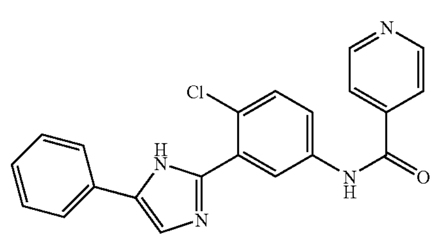 | 375.1 |

TABLE 1-continued
| Compound Number | Structure | Physical Data MS (m/z)/(M + 1) |
|---|---|---|
| 125 | 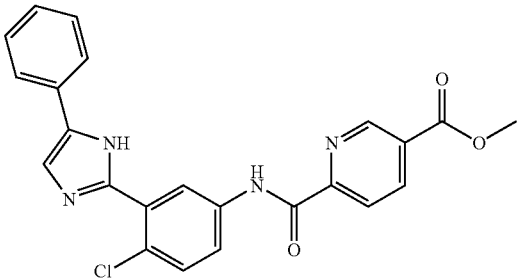 | 433.1 |
| 126 | 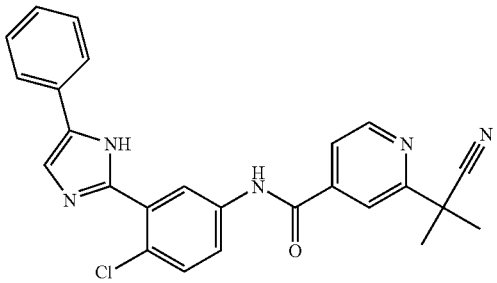 | 442.1 |
| 127 | 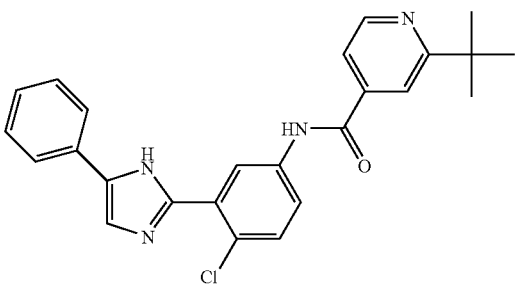 | 431.2 |
| 129 | 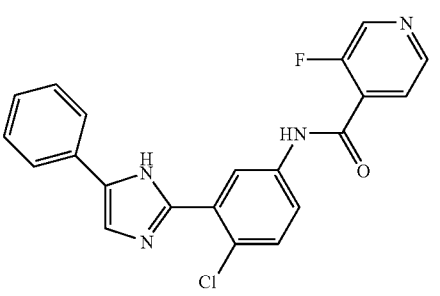 | 393.1 |
| 130 | 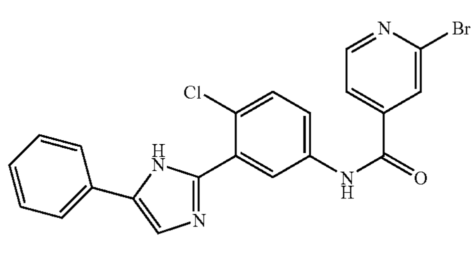 | 453.0 |

TABLE 1-continued

| Compound Number | Structure | Physical Data MS (m/z)/(M + 1) |
|---|---|---|
| 131 | 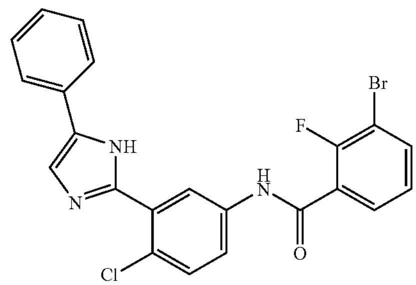 | 470.0 |
| 132 | 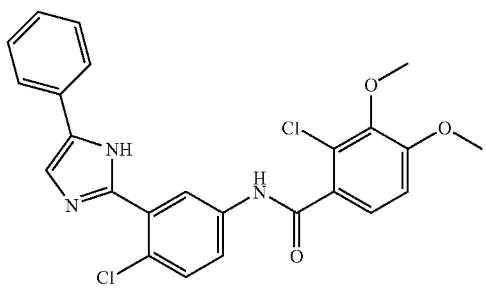 | 468.1 |
| 133 | 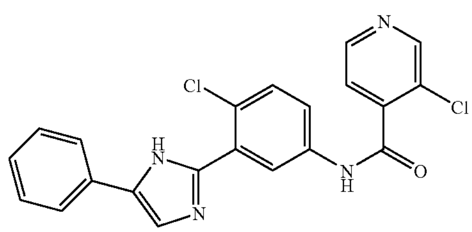 | 409.1 |
| 134 | 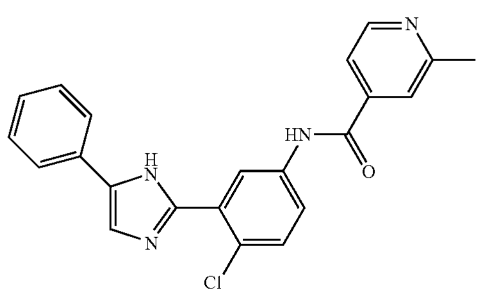 | 389.1 |
| 135 | 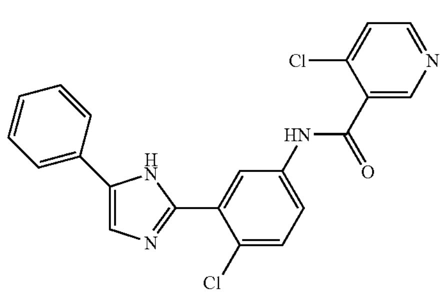 | 409.1 |

TABLE 1-continued

| Compound Number | Structure | Physical Data MS (m/z)/(M + 1) |
|---|---|---|
| 136 | 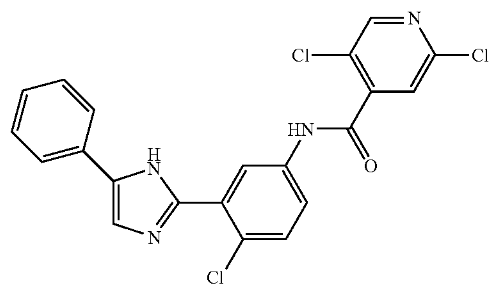 | 443.0 |
| 137 | 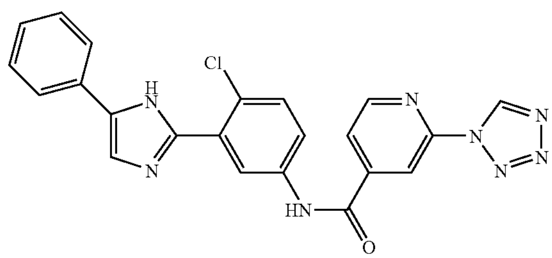 | 443.1 |
| 138 | 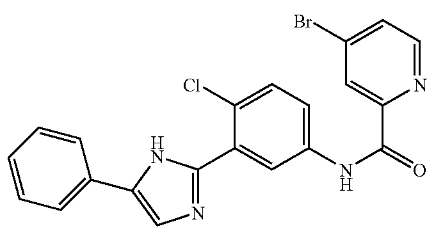 | 453.0 |
| 139 | 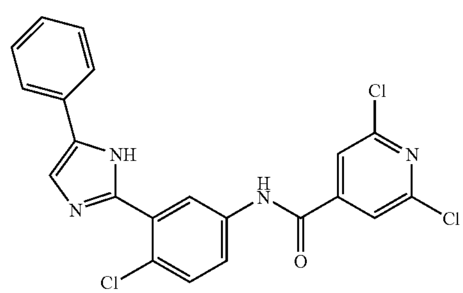 | 443.0 |
| 140 | 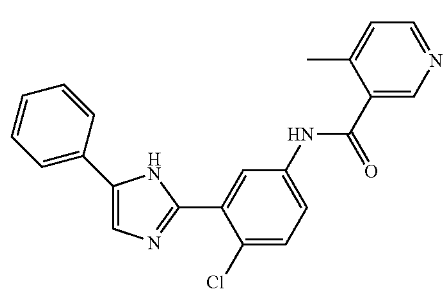 | 389.1 |

TABLE 1-continued

| Compound Number | Structure | Physical Data MS (m/z)/(M + 1) |
|---|---|---|
| 141 | 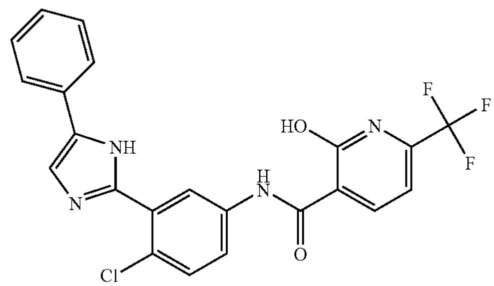 | 459.1 |
| 142 | 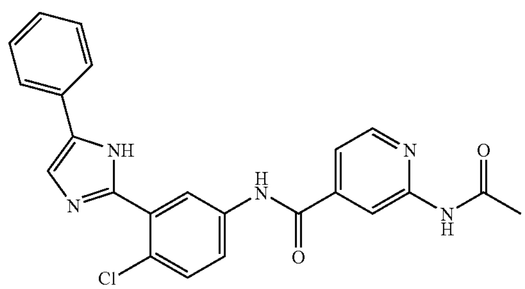 | 432.1 |
| 143 | 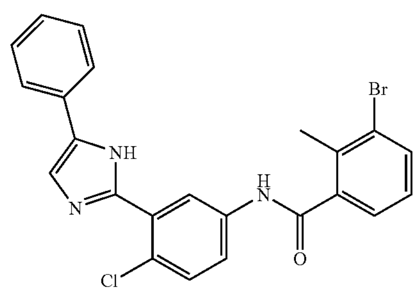 | 466.0 |
| 144 | 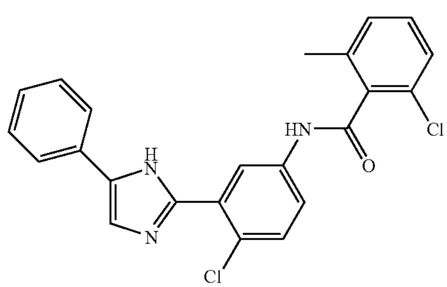 | 422.1 |
| 145 | 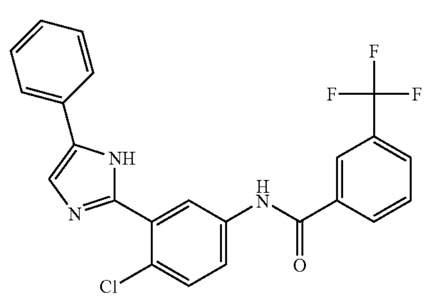 | 442.1 |

TABLE 1-continued

| Compound Number | Structure | Physical Data MS (m/z)/(M + 1) |
|---|---|---|
| 146 | 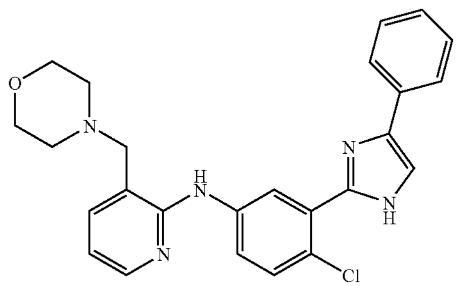 | 446.2 |
| 147 | 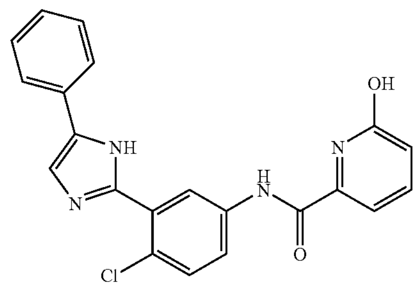 | 391.1 |
| 148 | 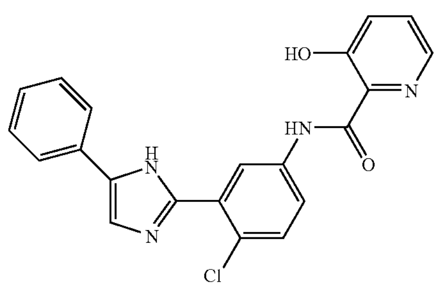 | 391.1 |
| 149 | 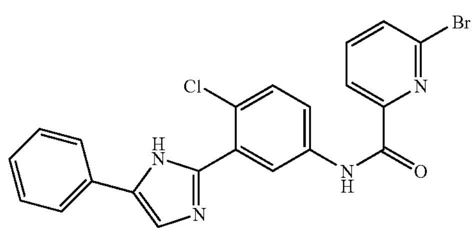 | 453.0 |
| 150 | 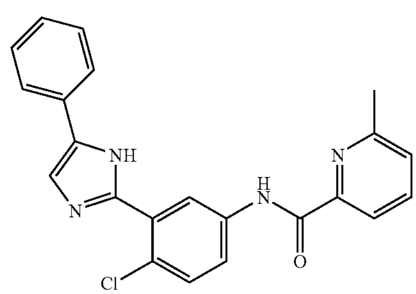 | 389.1 |

TABLE 1-continued

| Compound Number | Structure | Physical Data MS (m/z)/(M + 1) |
|---|---|---|
| 151 | 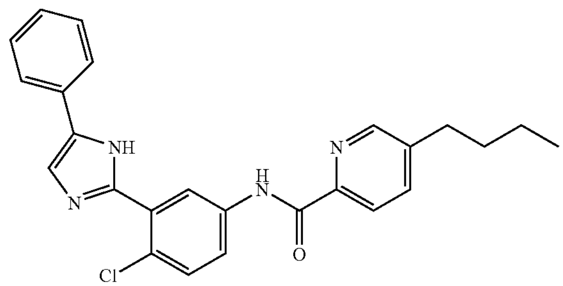 | 431.2 |
| 152 | 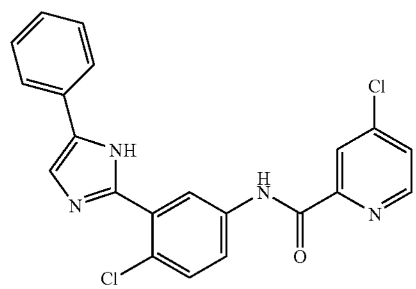 | 409.1 |
| 153 | 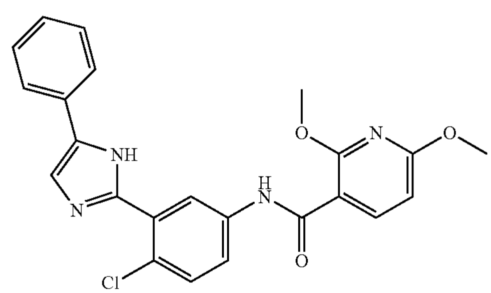 | 435.1 |
| 154 | 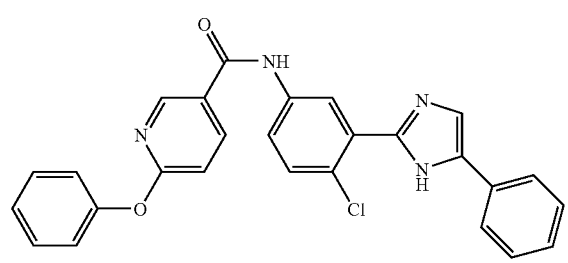 | 467.1 |
| 155 | 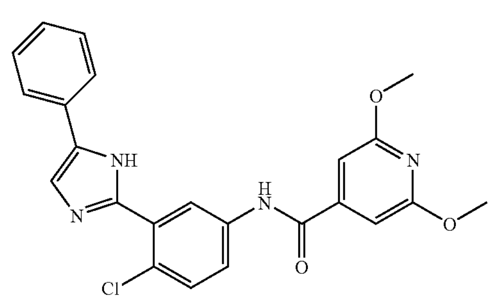 | 435.1 |

TABLE 1-continued
| Compound Number | Structure | Physical Data MS (m/z)/(M + 1) |
|---|---|---|
| 156 | 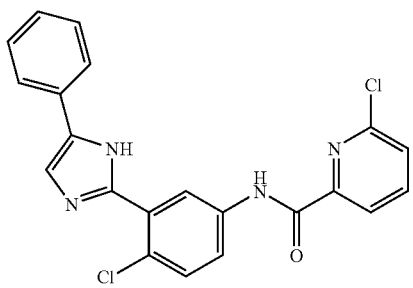 | 409.1 |
| 157 | 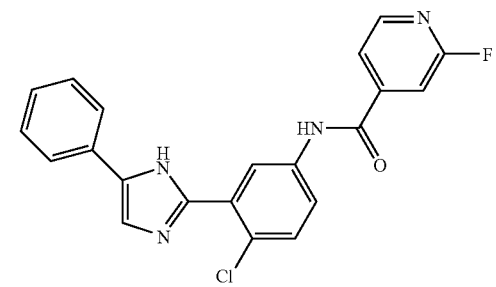 | 393.1 |
| 158 | 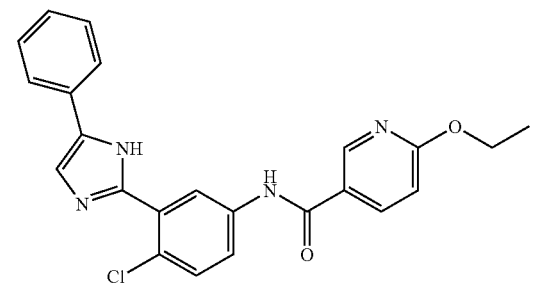 | 419.1 |
| 159 | 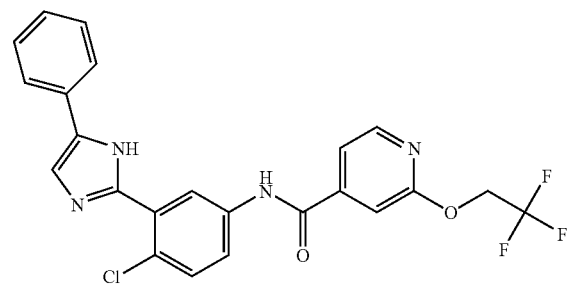 | 473.1 |
| 160 | 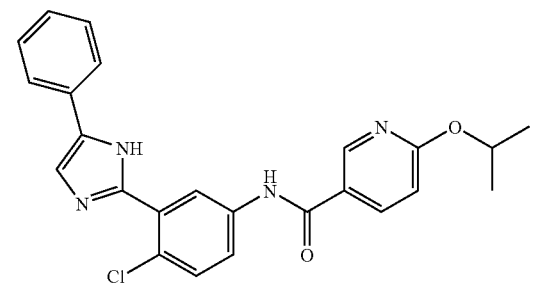 | 433.1 |

TABLE 1-continued
| Compound Number | Structure | Physical Data MS (m/z)/(M + 1) |
|---|---|---|
| 161 | 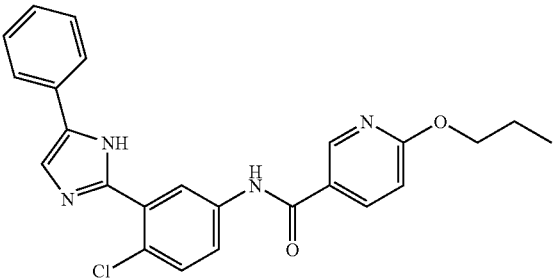 | 433.1 |
| 162 | 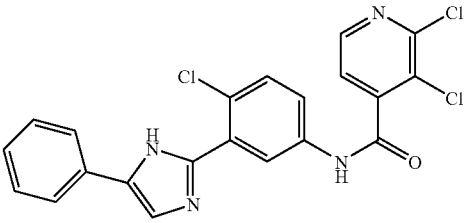 | 443.0 |
| 163 | 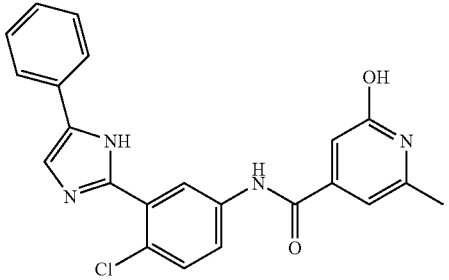 | 405.1 |
| 164 | 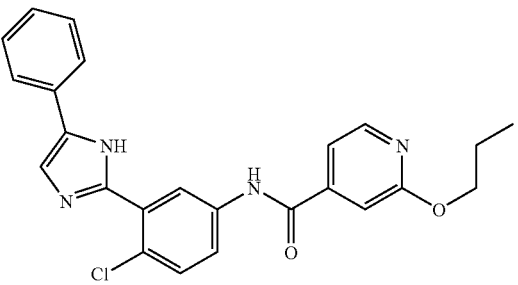 | 433.1 |
| 165 | 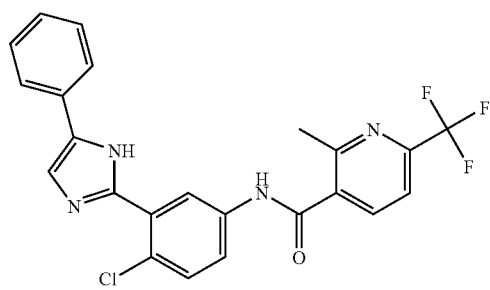 | 457.1 |

TABLE 1-continued

| Compound Number | Structure | Physical Data MS (m/z)/(M + 1) |
|---|---|---|
| 166 | 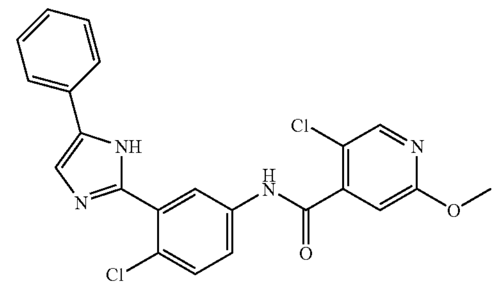 | 439.1 |
| 167 | 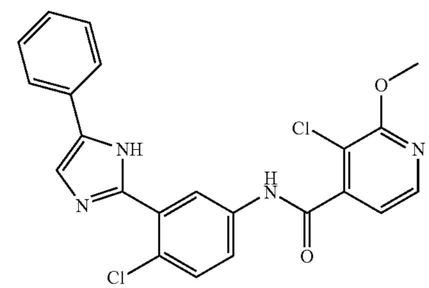 | 439.1 |
| 168 | 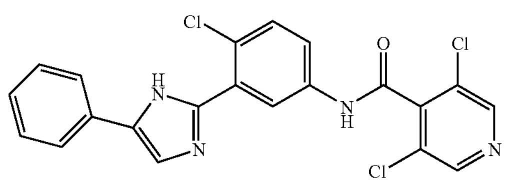 | 443.0 |
| 169 | 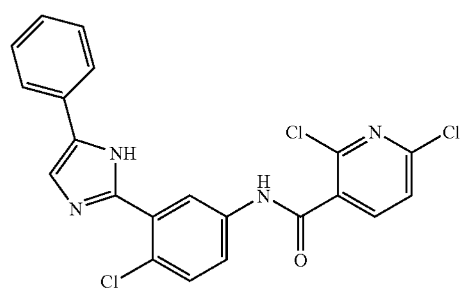 | 443.0 |
| 170 | 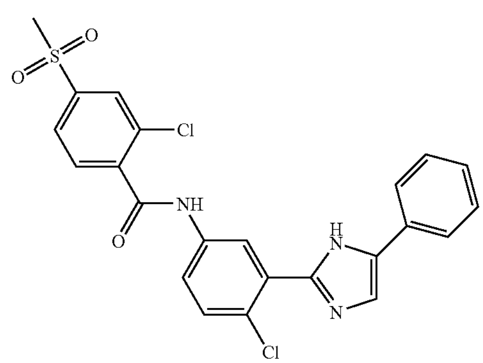 | 486.0 |

TABLE 1-continued

| Compound Number | Structure | Physical Data MS (m/z)/(M + 1) |
|---|---|---|
| 171 | 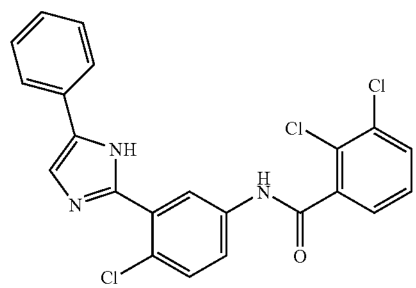 | 442.0 |
| 172 | 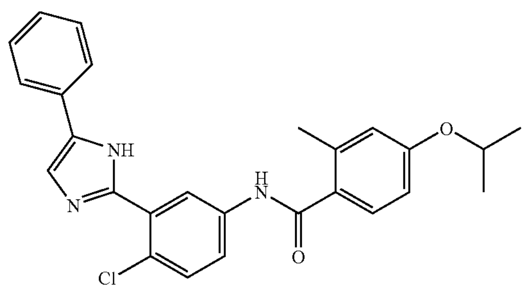 | 446.2 |
| 173 | 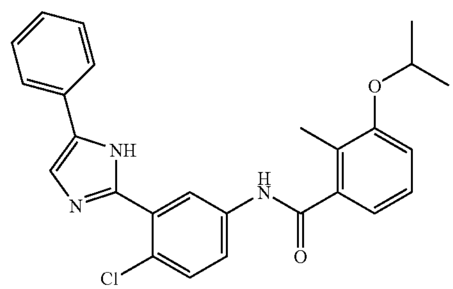 | 446.2 |
| 174 | 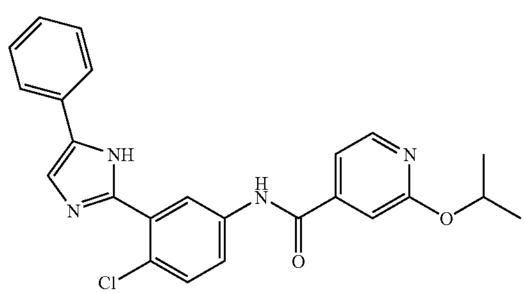 | 433.1 |
| 175 | 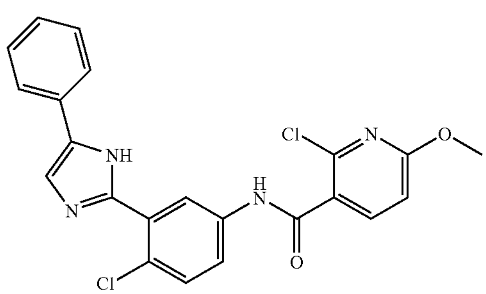 | 439.1 |

TABLE 1-continued

| Compound Number | Structure | Physical Data MS (m/z)/(M + 1) |
|---|---|---|
| 176 | 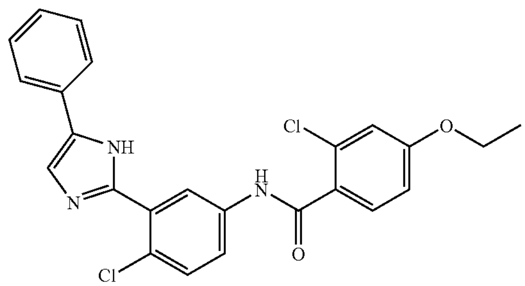 | 452.1 |
| 177 | 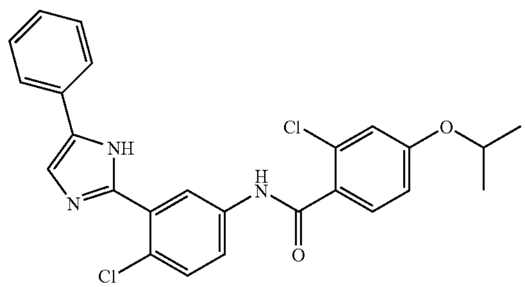 | 466.1 |
| 178 | 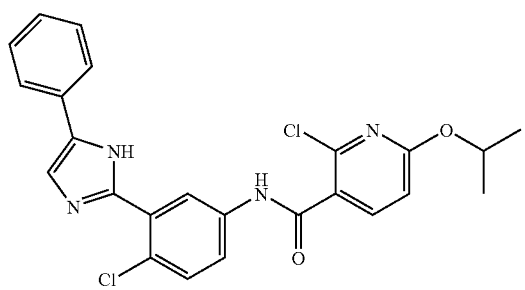 | 467.1 |
| 179 | 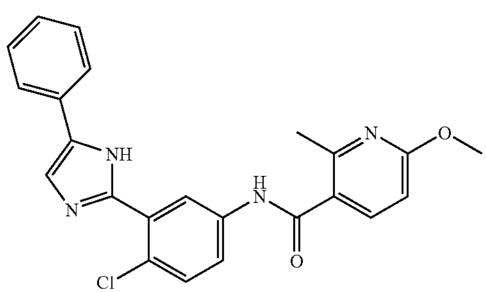 | 419.1 |
| 180 | 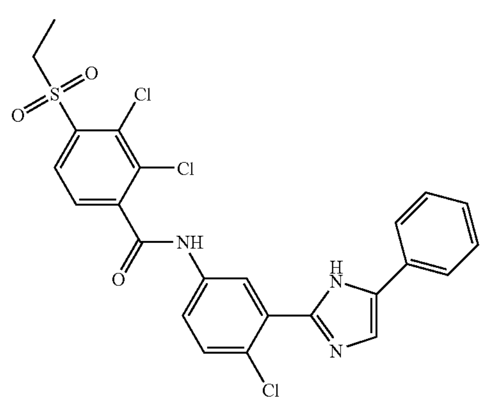 | 534.0 |

TABLE 1-continued

| Compound Number | Structure | Physical Data MS (m/z)/(M + 1) |
| --- | --- | --- |
| 181 | 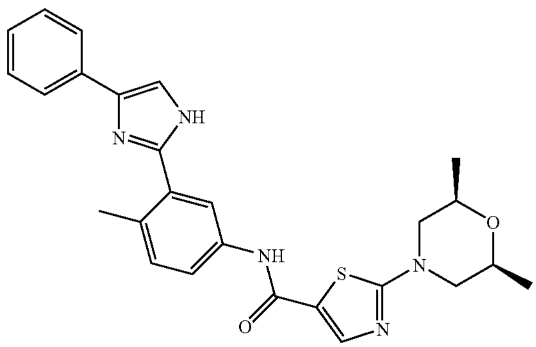 | 474.2 |
| 182 | 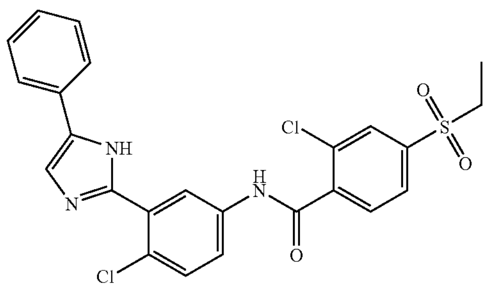 | 500.0 |
| 183 | 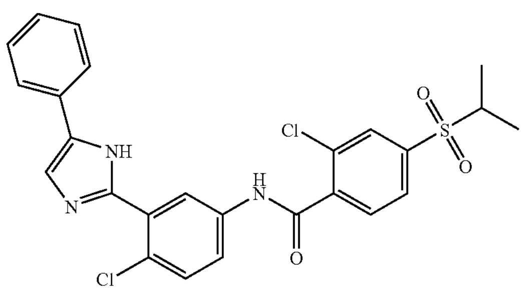 | 514.1 |
| 184 | 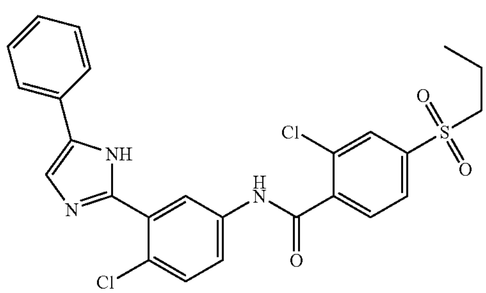 | 514.1 |
| 185 | 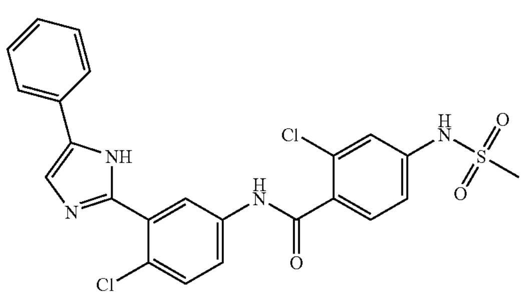 | 501.1 |

General materials and methods for the analysis of compounds of the invention are described in PCT application number PCT/US2007/038171 "Compounds and Compositions for Treating Lymphoma and Myeloma"; Dierks and Warmuth. The full disclosure of this application is incorporated herein by reference in its entirety and for all purposes. Compounds of the present invention are assayed to evaluate their capacity to inhibit the hedgehog signaling pathway.

Gli-Luc Reporter Assay for Hh Pathway Inhibition

Mouse TM3 cells (obtained from American Type Culture Collection, ATCC, Manassas, Va.) are cultured in DMEM/F12 medium (Gibco/Invitrogen, Carlsbad, Calif.) supplemented with 5% heat inactivated horse serum and 2.5% FBS (Gibco/Invitrogen, Carlsbad, Calif.), 50 unit/mL penicillin and 50 µg/mL of streptomycin (Gibco/Invitrogen, Carlsbad, Calif.) at 37° C. with 5% $CO_2$ in air atmosphere. TM3 cells were transfected with pTA-8xGli-Luc reporter plasmid. A stably transfected clone termed TMHh-12 was selected. TMHh-12 clone showed good response to Shh-N stimulation. To evaluate the IC50s of the antagonists, 8000 TMHh-12 cells were plated into each wells in 384-well plates with 50% DMEM/F12 medium supplemented with 2% FBS. After 12 hours, Hh pathway is activated by adding recombinant mouse Shh protein (expressed in $E.\ coli$, 8 µg/mL) or by adding Smo agonists. The testing compounds are added into plates with different concentrations. After 48 hours, the firefly luciferase luciferase activities are assayed with the Bright-Glo™ Luciferase Assay System (Promega, Madison, Wis.). The $IC_{50}$ is measured when the effect of the compound reduces the luminescence signal by 50%. Toxicity of these compounds are evaluated in TM3 cells using CellTiter Glo assays or by TM3-Luc cell line (a TM3 cell stably transfected with a constitutive luciferase expression vector).

Compounds of Formula I preferably have an $EC_{50}$ of less than 500 nM, more preferable less than 200 nM.

Inhibiting Hh Pathway Abrogates Lymphoma Expansion In Vivo

Stroma produced hedgehog ligands are important growth and survival factors for primary lymphoma cells under in-vitro culture conditions. Growth and expansion of lymphoma cells in-vivo is also dependent on Hh signaling. 1e6 lymphoma cells expressing luciferase were injected into syngeneic C57BL/6 mice. On day 2 post-injection, the mice were treated with either vehicle control or a compound of the invention (50, 25, 10 and 5 mg/kg/bid) for 10 days by oral administration. Luciferase levels were measured by bioluminescence imaging 3 times per week. Ten days post-injection, the control group shows high luminescence in the lymph nodes and spleens of all injected mice. Mice treated with a compound of the invention at 50, 25 and 10 mg/kg/bid showed a reduction of the luminescence signal to less than 10% compared to the control group (T/C below 10%). 5 mg/kg bid dosing group showed a partial response with a T/C from 40%. Therefore we conclude that hedgehog pathway inhibition reduces lymphoma growth in mice.

Embryonic Skin Punch Assay

Compounds of the invention are tested from their ability to treat non-melanoma skin cancer, i.e. basal cell carcinoma lesions using the skin punch assay. Mouse embryos from Ptch$^{+/-}$-LacZ mice, are collected and killed at late gestation (embryonic day 17.5) and their skins excised. Circular punches (4 mm in diameter are placed in a collagen-coated Transwell (BIOCOAT cell Culture Insert, Becton Dickinson Labware, Bedford, Mass.) and cultured at the air-liquid interface, with the epidermis side facing up. The culture medium contains 5% FBS in DMEM/F12 (3:1) with added epidermal growth factor, insulin, and hydrocortisone. To induce formation of basaloid nests, punches are grown in the presence of 1-2 µg/ml Shh for 4 or more days. Effects of compounds of the invention are tested by adding at the time of Shh addition or after 6 days of Shh pretreatment. Compounds of the invention show full inhibition (preventing lesion formation) at concentrations of 1 µM or less.

Compounds of Formula I preferably have an $EC_{50}$ of less than 500 nM, more preferable less than 200 nM to block basanoid formation.

Psoriasis Assay

Compounds of the invention are tested form their ability to treat psoriatic skin lesions according to the assay described in Tas & Avci, Pharmacology and Treatment, Dermatology 2004; 209:126-131.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

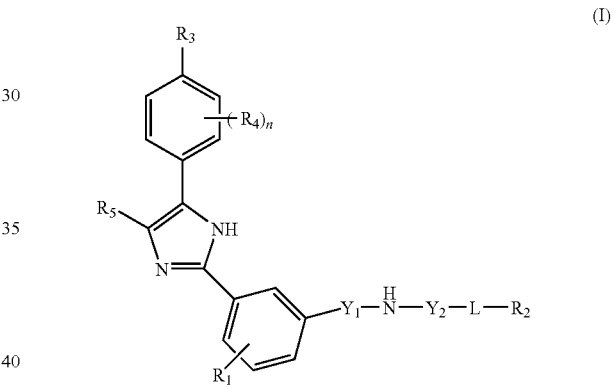

in which:

n is selected from 0, 1 and 2;

$Y_1$ is selected from a bond and C(O);

$Y_2$ is selected from a bond and C(O);

$R_1$ is selected from hydrogen, halo, cyano, $C_{1-2}$alkyl and halo-substituted-$C_{1-2}$alkyl;

$R_2$ is selected from hydrogen, halo, cyano, $C_{1-3}$alkyl, $C_{1-3}$alkoxy, halo-substituted-$C_{1-3}$alkyl, halo-substituted-$C_{1-3}$alkoxy, $C_{6-10}$aryl-$C_{0-4}$alkyl $C_{1-10}$heteroaryl-$C_{0-4}$-alkyl, $C_{3-12}$cycloalkyl-$C_{0-4}$alkyl, $C_{3-8}$heterocycloalkyl-$C_{0-4}$alkyl and phenoxy;

wherein said aryl, heteroaryl, cycloalkyl, heterocycloalkyl or phenoxy of $R_2$ can be optionally substituted with 1 to 3 radicals independently selected from $C_{1-6}$alkyl, halo-substituted-$C_{1-6}$alkyl, $C_{1-6}$alkoxy, halo-substituted-$C_{1-6}$alkoxy, $C_{6-10}$aryl-$C_{0-4}$alkyl $C_{1-10}$heteroaryl-$C_{0-4}$alkyl, $C_{3-12}$cycloalkyl and $C_{3-8}$heterocycloalkyl;

wherein said aryl-alkyl substituent of $R_2$ is optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy and methyl-piperazinyl;

$R_3$ is selected from hydrogen, halo, cyano, $C_{1-2}$alkyl, $C_{1-3}$alkoxy and halo-substituted-$C_{1-2}$alkyl;

$R_4$ is selected from hydrogen, halo, cyano, $C_{1-2}$alkyl and $C_{1-3}$alkoxy;

$R_5$ is selected from hydrogen and $C_{1-3}$alkyl;
L is a divalent radical selected from:

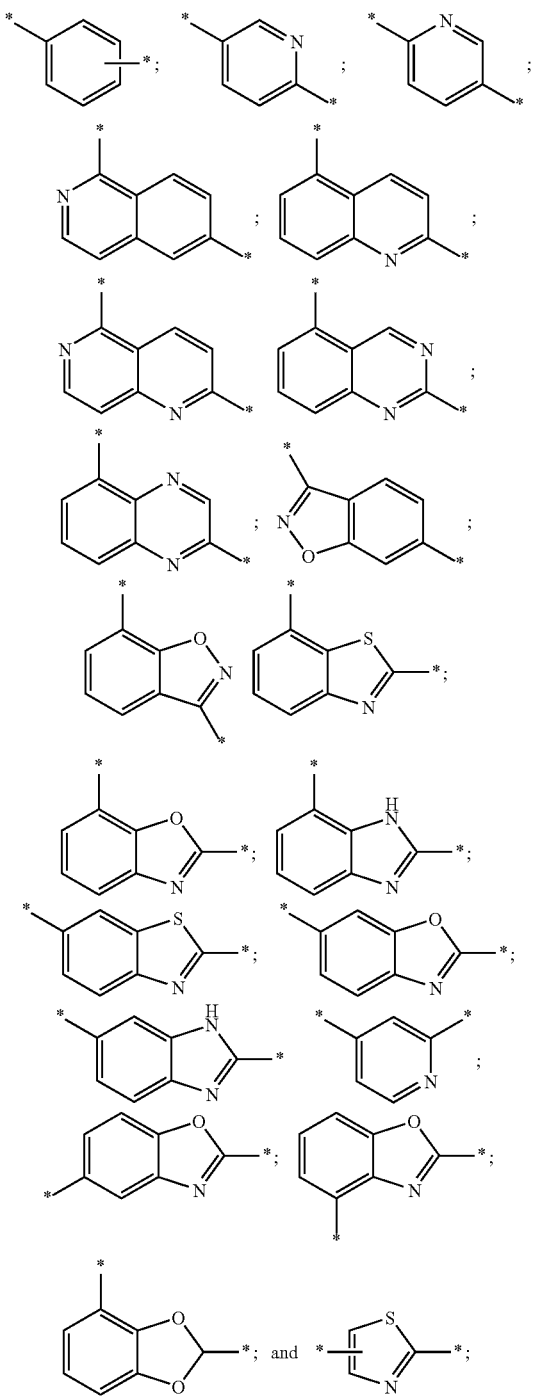

in which the asterisks indicate the point of attachment between $Y_2$ and $R_2$; wherein any divalent radical of L can be further substituted with 1 to 3 radicals independently selected from halo, hydroxy, cyano, $C_{1-4}$alkyl, $C_{1-4}$alkyl-carbonyl-amino, $C_{1-4}$alkoxy, $C_{1-4}$alkoxy-carbonyl, halo-substituted-$C_{1-4}$alkyl, $C_{1-3}$alkyl-sulfonyl, $C_{1-3}$alkyl-sulfonyl-amino, cyano-substituted-$C_{1-4}$alkyl and halo-substituted-$C_{1-4}$alkoxy; or a pharmaceutically acceptable salts thereof.

2. The compound of claim 1 in which:
n is selected from 0 and 1;
$Y_1$ is selected from a bond and C(O);
$Y_2$ is selected from a bond and C(O);
$R_1$ is selected from hydrogen, halo and $C_{1-2}$alkyl;
$R_2$ is selected from hydrogen, halo, cyano, $C_{1-3}$alkyl, $C_{1-3}$alkoxy, halo-substituted-$C_{1-3}$alkyl, halo-substituted-$C_{1-3}$alkoxy, $C_{6-10}$aryl-$C_{0-4}$alkyl, $C_{1-10}$heteroaryl-$C_{0-4}$alkyl, $C_{3-12}$cycloalkyl-$C_{0-4}$alkyl, $C_{3-8}$heterocycloalkyl-$C_{0-4}$alkyl and phenoxy;
wherein said aryl, heteroaryl, cycloalkyl, heterocycloalkyl or phenoxy of $R_2$ can be optionally substituted with 1 to 3 radicals independently selected from $C_{1-6}$alkyl, halo-substituted-$C_{1-6}$alkyl, $C_{1-6}$alkoxy and halo-substituted-$C_{1-6}$alkoxy;
$R_3$ is selected from hydrogen, halo, cyano, $C_{1-2}$alkyl, $C_{1-3}$alkoxy, halo-substituted-$C_{1-2}$alkyl and -$NR_{6a}R_{6b}$; wherein $R_{6a}$ and $R_{6b}$ are independently selected from hydrogen and $C_{1-4}$alkyl;
$R_4$ is selected from hydrogen, halo, cyano and $C_{1-2}$alkyl
$R_5$ is selected from hydrogen and $C_{1-3}$alkyl;
L is a divalent radical selected from:

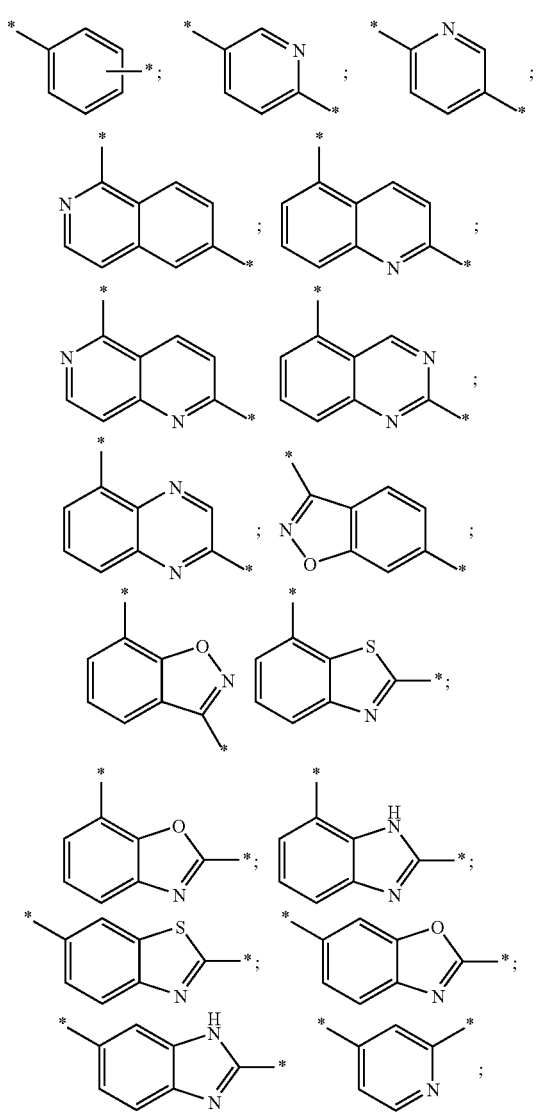

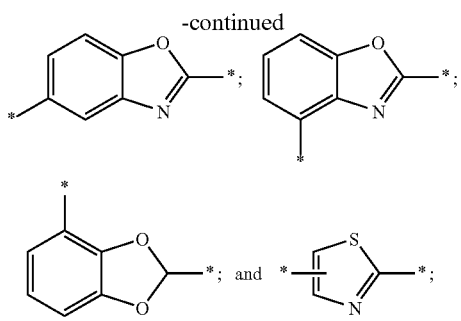

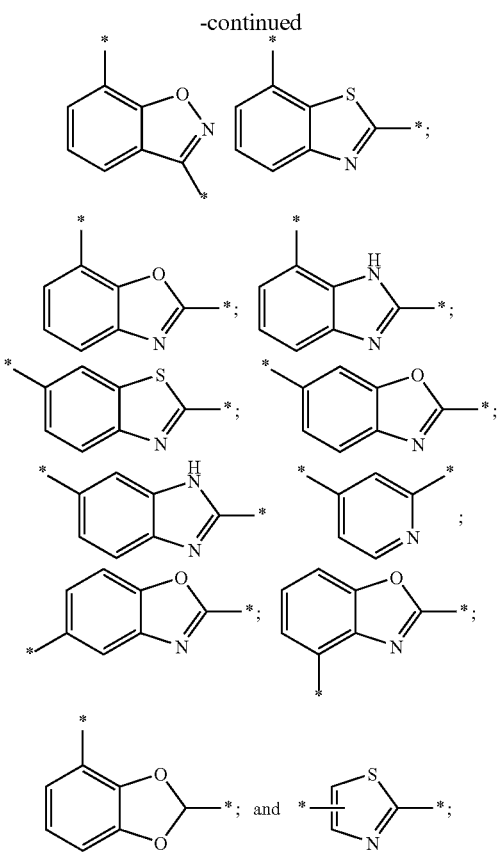

in which the asterisks indicate the point of attachment between $Y_2$ and $R_2$; wherein any divalent radical of L can be further substituted with 1 to 3 radicals independently selected from halo, hydroxy, cyano, $C_{1-4}$alkyl, $C_{1-3}$alkyl-sulfonyl, $C_{1-3}$alkyl-sulfonyl-amino, $C_{1-3}$ alkyl -carbonyl-amino, $C_{1-3}$alkoxy, $C_{1-3}$alkoxy-carbonyl, halo-substituted-$C_{1-3}$alkyl, cyano-substituted-$C_{1-3}$alkyl and halo-substituted-$C_{1-3}$alkoxy.

3. The compound of claim 2 in which: n is selected from 0 and 1; $Y_1$ is selected from a bond and C(O); $Y_2$ is selected from a bond and C(O); and $R_1$ is selected from hydrogen, chloro and methyl.

4. The compound of claim 3 in which $R_2$ is selected from hydrogen, halo, methyl, ethyl, cyano, methoxy, ethoxy, trifluoromethyl, trifluoromethoxy, phenoxy, morpholino, morpholino-methyl, cyclohexyl, thiomorpholino, 1H-tetrazol-1-yl, piperidinyl and azepan-1-yl; wherein said phenoxy, morpholino, morpholino-methyl, cyclohexyl, thiomorpholino, 1H-tetrazol-1-yl, piperidinyl or azepan-1-yl of $R_2$ can be optionally substituted with 1 to 3 methyl radicals; wherein said sulfur of thiomorpholino can be bound to 0, 1 or 2 oxygen atoms.

5. The compound of claim 4 in which: $R_3$ is selected from hydrogen, chloro, fluoro, cyano, trifluoromethyl, methoxy and diethylamino; $R_4$ is selected from hydrogen and chloro; $R_5$ is selected from hydrogen and methyl; and L is a divalent radical selected from:

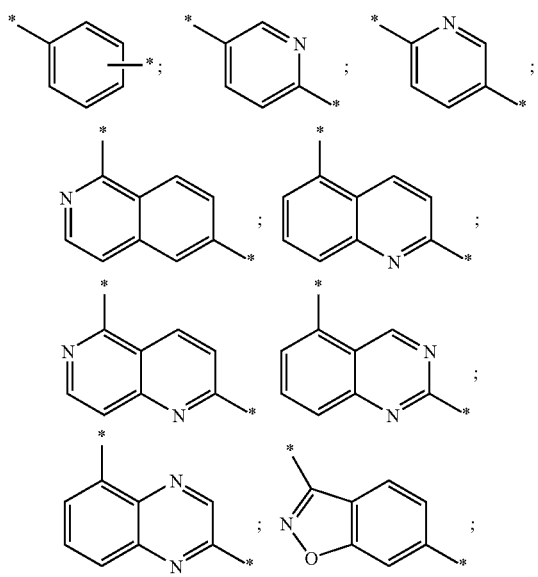

in which the asterisks indicate the point of attachment between $Y_2$ and $R_2$; wherein any divalent radical of L can be further substituted with 1 to 3 radicals independently selected from hydroxy, bromo, chloro, fluoro, methyl, ethyl, cyano, methyl-carbonyl-amino, butyl, methoxy, trifluoromethyl, trifluoroethoxy, 2-cyanopropan-2-yl, trifluoromethoxy, methoxy -carbonyl, propoxy, methyl-sulfonyl, methyl-sulfonyl-amino, ethyl-sulfonyl, propyl-sulfonyl, isopropyl-sulfonyl, isopropoxy and ethoxy.

6. A compound selected from [4-Chloro-3-(5-phenyl-1H-imidazol-2-yl)-phenyl]-[6-(2-methyl-morpholin-4-yl)-isoquinolin-1-yl]-amine, [4-Chloro-3-(5-phenyl-1H-imidazol-2-yl)-phenyl]-[2-(2-methyl-morpholin-4-yl)-quinolin-5-yl]-amine, [4-Chloro-3-(5-phenyl-1H-imidazol-2-yl)-phenyl]-[2-(2-methyl-morpholin-4-yl) -[1,6]naphthyridin-5-yl]-amine, [4-Chloro-3-(5-phenyl-1H-imidazol-2-yl)-phenyl]-[6-(2,6-dimethyl -morpholin-4-yl)-isoquinolin-1-yl]-amine, [4-Chloro-3-(5-phenyl-1H-imidazol-2-yl) -phenyl]-(6-morpholin-4-yl-isoquinolin-1-yl)-amine, N-[4-Chloro-3-(4-phenyl-1H-imidazol -2-yl)-phenyl]-4-morpholin-4-yl-benzamide, N-[4-Chloro-3-(4-phenyl-1H-imidazol-2-yl)-phenyl]-4-cyclohexyl-benzamide, [4-Chloro-3-(5-phenyl-1H-imidazol-2-yl)-phenyl]-(2-morpholin-4-yl-quinolin-5-yl)-amine, [4-Methyl-3-(5-phenyl-1H-imidazol-2-yl)-phenyl]-(6-piperidin-1-yl-isoquinolin-1-yl)-amine, (6-Azepan-1-yl-isoquinolin-1-yl)-[4-methyl-3-(5-phenyl-1H-imidazol-2-yl)-phenyl]-amine, N-[4-Methyl-3-(4-phenyl-1H-imidazol-2-yl)-phenyl]-4-morpholin-4-yl-benzamide, 4-Cyclohexyl-N-[4-methyl-3-(4-phenyl-1H-imidazol-2-yl)-phenyl]-benzamide, N-{3-[5-(4-Chloro-phenyl)-1H-imidazol-2-yl]-4-methyl-phenyl}-4-morpholin-4-yl-benzamide, [4-Methyl-3-(5-phenyl-1H-imidazol-2-yl)-phenyl]-(2-morpholin-4-yl-

[1,6]naphthyridin-5-yl)-amine, (6-Azepan-1-yl-isoquinolin-1-yl)-[4-chloro-3-(5-phenyl-1H-imidazol-2-yl)-phenyl]-amine, [4-Chloro-3-(5-phenyl-1H-imidazol-2-yl)-phenyl]-(7-morpholin-4-yl-isoquinolin-1-yl)-amine, [4-Chloro-3-(5-phenyl-1H-imidazol-2-yl)-phenyl]-(6-piperidin-1-yl-isoquinolin-1-yl)-amine, 3,5-Dimethoxy-N-[4-methyl-3-(5-phenyl-1H-imidazol-2-yl)-phenyl]-benzamide, N-{3-[4-(4-Diethylamino-phenyl)-1H-imidazol-2-yl]-4-methyl-phenyl}1-4-morpholin-4-yl-benzamide, N-{4-Chloro-3-[4-(4-chloro-phenyl)-1H-imidazol-2-yl]-phenyl}-4-morpholin-4-yl-benzamide, (6-Morpholin-4-yl-isoquinolin-1-yl)-[3-(5-phenyl-1H-imidazol-2-yl)-phenyl]-amine, N-{3-[5-(4-Fluoro-phenyl)-1H-imidazol-2-yl]-4-methyl-phenyl}-4-morpholin-4-yl-benzamide, (6-Morpholin-4-yl-isoquinolin-1-yl)-[3-(5-phenyl-1H-imidazol-2-yl)-phenyl]-amine, (2-Morpholin-4-yl-quinolin-5-yl)-[3-(5-phenyl-1H-imidazol-2-yl)-phenyl]-amine, 6-Morpholin-4-yl-N-[3-(4-phenyl-1H-imidazol-2-yl)-phenyl]-nicotinamide, N-{3-[5-(3-Chloro-phenyl)-1H-imidazol-2-yl]-4-methyl-phenyl}-4-morpholin-4-yl-benzamide, 4-Cyclohexyl-N-[3-(5-phenyl-1H-imidazol-2-yl)-phenyl]-benzamide, 4-Morpholin-4-yl-N-[3-(4-phenyl-1H-imidazol-2-yl)-phenyl]-benzamide, N-{3-[5-(2-Chloro-phenyl)-1H-imidazol-2-yl]-4-methyl-phenyl}-4-morpholin-4-yl-benzamide, 4-Cyclohexyl-N-{3-[4-(4-fluoro-phenyl)-1H-imidazol-2-yl]-phenyl}-benzamide, N-{3-[5-(4-Cyano-phenyl)-1H-imidazol-2-yl]-4-methyl-phenyl}-3,5-dimethoxy-benzamide, 6-Azepan-1-yl-N-[3-(4-phenyl-1H-imidazol-2-yl)-phenyl]-nicotinamide,4-Morpholin-4-yl-N-[3-(5-phenyl-1H-imidazol-2-yl)-phenyl]-benzamide, N-{4-Methyl-3-[5-(4-trifluoromethyl-phenyl)-1H-imidazol-2-yl]-pheny}-4-morpholin-4-yl-benzamide, [4-Chloro-3-(5-phenyl-1H-imidazol-2-yl)-phenyl]-isoquinolin-1-yl-amine, 4-Cyclohexyl-N-{3-[4-(4-methoxy-phenyl)-1H-imidazol-2-yl]-phenyl}-benzamide, 3,4,5,6-Tetrahydro-2H-[1,2]bipyridinyl-5'-carboxylic acid [3-(4-phenyl-1H-imidazol-2-yl)-phenyl]-amide, 6-Azepan-1-yl-N-[2-methyl-3-(4-phenyl-1H-imidazol-2-yl)-phenyl]-nicotinamide, N-{3-[4-(4-Cyano-phenyl)-1H-imidazol-2-yl]-phenyl}-4-cyc lohexyl-benzamide, 4-Morpholin-4-yl-N-[345-phenyl-1H-imidazol-2-yl)-phenyl]-benzene sulfonamide, [2-Methyl-3-(5-phenyl-1H-imidazol-2-yl)-phenyl]-(6-morpholin-4-yl-isoquinolin-1-yl)-amine, N-[4-Chloro-3-(5-methyl-4-phenyl-1H-imidazol-2-yl)-phenyl]-4-morpholin-4-yl-benzamide, N-[4-Methyl-3-(5-methyl-4-phenyl-1H-imidazol-2-yl)-phenyl]-4-morpholin-4-yl-benzamide, N-(6-Morpholin-4-yl-pyridin-3-yl)-3-(4-phenyl-1H-imidazol-2-yl)-benzamide, N-[2-Methyl-3-(4-phenyl-1H-imidazol-2-yl)-phenyl]-6-morpholin-4-yl-nicotinamide, 3,4,5,6-Tetrahydro-2H-[1,2]bipyridinyl-5'-carboxylic acid [2-methyl-3-(4-phenyl-1H-imidazol-2-yl)-phenyl]-amide, 4-Cyclohexyl-N-[2-methyl-3-(4-phenyl-1H-imidazol-2-yl)-phenyl]-benzamide, [4-Chloro-3-(5-phenyl-1H-imidazol-2-yl)-phenyl]-[2-(2,6-dimethyl-morpholin-4-yl)-quinolin-5-yl]-amine, [4-Chloro-3-(4-phenyl-1H-imidazol-2-yl)-phenyl]-[2-(2,6-dimethyl-morpholin-4-yl) -[1,6]naphthyridin-5-yll-amine, N-[4-Chloro-3-(5-phenyl-1H-imidazol-2-yl)-phenyl]-2-methoxy-isonicotinamide, 2-Chloro-N-[4-chloro-3-(5-phenyl-1H-imidazol-2-yl)-phenyl]-6-methyl-isonicotinamide, 2,6-Dichloro-N-[4-chloro-3-(5-phenyl-1H-imidazol-2-yl)-phenyl]-isonicotinamide, N-[4-Chloro-3-(5-phenyl-1H-imidazol-2-yl)-phenyl]-2-methoxy-isonicotinamide, 6-Chloro-N-[4-chloro-3-(5-phenyl-1H-imidazol-2-yl)-phenyl]-nicotinamide, N-[4-Chloro-3-(5-phenyl-1H-imidazol-2-yl)-phenyl]-6-trifluoromethyl-nicotinamide, 2-Chloro-N-[4-chloro-3-(5-phenyl-1H-imidazol-2-yl)-phenyl]-6-methoxy-isonicotinamide, Quinoline-3-carboxylic acid [4-chloro-3-(5-phenyl-1H-imidazol-2-yl)-phenyl]-amide, N-[4-Chloro-3-(5-phenyl-1H-imidazol-2-yl)-phenyl]-nicotinamide, N-[4-Chloro-3-(5-phenyl-1H-imidazol-2-yl)-phenyl]-5-methoxy-2-(2,2,2-trifluoro-ethoxy)-benzamide, N-[4-Chloro-3-(5-phenyl-1H-imidazol-2-yl)-phenyl]-3,4-diethoxy-benzamide, N-[4-Chloro-3-(5-phenyl-1H-imidazol-2-yl)-phenyl]-3-methoxy-4-methyl-benzamide, 4-Chloro-N-[4-chloro-3-(5-phenyl-1H-imidazol-2-yl)-phenyl]-3-methoxy-benzamide, 2,2-Difluoro-benzo[1,3]dioxole-4-carboxylic acid [4-chloro-3-(5-phenyl-1H-imidazol-2-yl)-phenyl]-amide, N-[4-Chloro-3-(5-phenyl-1H-imidazol-2-yl)-phenyl]-3-methoxy-2-methyl-benzamide, N-[4-Chloro-3-(5-phenyl-1H-imidazol-2-yl)-phenyl]-2,5-dimethoxy-benzamide, N-[4-Chloro-3-(5-phenyl-1H-imidazol-2-yl)-phenyl]-3,5-dimethoxy-4-methyl-benzamide, 6-Methyl-benzo[1,3]dioxole-5-carboxylic acid [4-chloro-3-(5-phenyl-1H-imidazol-2-yl)-phenyl]-amide, [4-Chloro-3-(4-phenyl -1H-imidazol-2-yl)-phenyl]-[7-(2,6-dimethyl-morpholin-4-yl)-quinolin-4-yl]-amine, [4-Chloro-3-(5-phenyl-1H-imidazol-2-yl)-phenyl]-[8-methyl-2-(2-methyl-morpholin-4-yl)-quinolin-5-yl]-amine, [4-Chloro-3-(5-phenyl-1H-imidazol-2-yl)-phenyl]-[2-(2-methyl-morpholin-4-yl)-quinazolin-5-yl]-amine, [4-Chloro-3-(5-phenyl-1H-imidazol-2-yl)-phenyl]-[2-(2,6-dimethyl-morpholin-4-yl)-quinazolin-5-yl]-amine, [4-Chloro-3-(5-phenyl-1H-imidazol-2-yl)-phenyl]-[2-(2-methyl-morpholin-4-yl)-quinoxalin-5-yl]-amine, [2,6-Dimethyl-morpholin-4-yl)-quinoxalin-5-yl]-[4-methyl-3-(5-phenyl-1H-imidazol-2-yl)-phenyl]-amine, [4-Chloro-3-(5-phenyl-1H-imidazol-2-yl)-phenyl]-[3-(2-methyl-morpholin-4-yl)-benzo[d]isoxazol-7-yl1-amine, [4-Chloro-3-(5-phenyl-1H-imidazol-2-yl)-phenyl]-[6-(2-methyl-morpholin-4-yl)-benzo[d]isoxazol-3-yl]-amine, [4-Chloro-3-(5-phenyl-1H-imidazol-2-yl)-phenyl]-[2-(2-methyl-morpholin-4-yl)-benzooxazol-4-yl]-amine, [4-Chloro-3-(5-phenyl-1H-imidazol-2-$_3$1)-phenyl]-[2-(2-methyl-morpholin-4-yl)-1H-benzoimidazol-4-yl]-amine, [2-(2,6-Dimethyl-morpholin-4-yl)-benzothiazol-4-yl]-P-methyl-3-(5-phenyl-1H-imidazol-2-$_3$1)-phenyll-amine, [2-(2,6-Dimethyl-morpholin-4-yl)-benzothiazol-7-yl]-[4-methyl-3-(5-phenyl-1H-imidazol-2-$_3$1)-phenyl]-amine, [4-Chloro-3-(5-phenyl-1H-imidazol-2-yl)-phenyl]-[3-(2-methyl-morpholin-4-yl)-benzo[d]isoxazol-5-yl]-amine, [4-Chloro-3-(5-phenyl-1H-imidazol-2-$_3$1)-phenyl]-[2-(2-methyl-morpholin-4-yl)-benzooxazol-5-yl]-amine, [2-(2,6-Dimethyl-morpholin-4-yl)-1H-benzoimidazol-4-yl]-[4-methyl-3-(5-phenyl-1H-imidazol-2-$_3$1)-phenyl]-amine, N-(4-chloro-3-(5-phenyl-1H-imidazol-2-yl)phenyl)-3-methoxybenzamide, N-(4-chloro-3-(5-phenyl-1H-imidazol-2-yl)phenyl)-2-methylbenzamide, N-(4-chloro-3-(5-phenyl-1H-imidazol-2-yl)phenyl)-2-(trifluoromethyl)benzamide, N-(4-chloro-3-(5-phenyl-1H-imidazol-2-yl)phenyl)-2,3-dimethoxybenzamide, N-(4-chloro-3-(5-phenyl-1H-imidazol-2-yl)phenyl)benzo[d]thiazole-6-carboxamide, N-(4-chloro-3-(5-phenyl-1H-imidazol-2-yl)phenyl)picolinamide, N-(4-chloro-3-(5-phenyl-1H-imidazol-2-yl)phenyl)-3-(trifluoromethoxy)benzamide, N-(4-chloro-3-(5-phenyl-1H-imidazol-2-yl)phenyl)-4-methoxy-2-methylbenzamide, N-(4-chloro-3-(5-phenyl-1H-imidazol-2-yl)phenyl)-2-hydroxynicotinamide, N-(4-chloro-3-(5-phenyl-1H-imidazol-2-yl)phenyl)-2-hydroxy-6-methylnicotinamide, N-(4-chloro-3-(5-phenyl-1H-imidazol-2-yl)phenyl)-2-methoxyisonicotinamide, N-(4-chloro-3-(5-phenyl-1H-imidazol-2-yl)phenyl)-3-methylpicolinamide, N-(4-chloro-3-(5-phenyl-1H-imidazol-2-yl)phenyl)-3-ethoxy-2-methylbenzamide, N-(4-chloro-3-(5-phenyl-1H-imidazol-2-yl)phenyl)-6-(2,2,2-trifluoroethoxy)nicotinamide, 2-chloro-N-(4-chloro-3-(5-phenyl-1H-imidazol-2-yl)phenyl)-6-

(trifluoromethyl)nicotinamide, 6-bromo-N-(4-chloro-3-(5-phenyl-1H-imidazol-2-yl) phenyl)nicotinamide, N-(4-chloro-3-(5-phenyl-1H-imidazol-2-yl)phenyl)-6-cyanonicotinamide, N-(4-chloro-3-(5-phenyl-1H-imidazol-2-yl)phenyl)-6-methylnicotinamide, N-(4-chloro-3-(5-phenyl-1H-imidazol-2-yl)phenyl)-6-hydroxynicotinamide, N-(4-chloro-3-(5-phenyl-1H-imidazol-2-yl)phenyl)-2-methoxynicotinamide, N-(4-chloro-3-(5-phenyl-1H-imidazol-2-yl)phenyl)-5-methylnicotinamide, N-(4-chloro-3-(5-phenyl-1H-imidazol-2-yl)phenyl)-5-fluoronicotinamide, 5-bromo-N-(4-chloro-3-(5-phenyl-1H-imidazol-2-yl) phenyl)nicotinamide, N-(4-chloro-3-(5-phenyl-1H-imidazol-2-yl)phenyl)-2-ethoxynicotinamide, N-(4-chloro-3-(5-phenyl-1H-imidazol-2-yl)phenyl)-2-ethyl-3-methoxybenzamide, N-(4-chloro-3-(5-phenyl-1H-imidazol-2-yl)phenyl)-6-methoxynicotinamide, N-(4-chloro-3-(5-phenyl-1H-imidazol-2-yl)phenyl)-2-fluoronicotinamide, 2-chloro-N-(4-chloro-3-(5-phenyl-1H-imidazol-2-yl)phenyl)nicotinamide, 2-chloro-N-(4-chloro-3-(5-phenyl-1H-imidazol-2-yl)phenyl)-6-methylnicotinamide, 5,6-dichloro-N-(4-chloro-3-(5-phenyl-1H-imidazol-2-yl)phenyl)nicotinamide, N-(4-chloro-3-(5-phenyl-1H-imidazol-2-yl)phenyl)-2-methylnicotinamide, N-(4-chloro-3-(5-phenyl-1H-imidazol-2-yl)phenyl)-2-ethoxyisonicotinamide, 2-chloro-N-(4-chloro-3-(5-phenyl-1H-imidazol-2-yl)phenyl) isonicotinamide, N-(4-chloro-3-(5-phenyl-1H-imidazol-2-yl)phenyl)isonicotinamide, methyl 6-(4-chloro-3-(5-phenyl-1H-imidazol-2-yl)phenylcarbamoyl)nicotinate, N-(4-chloro-3-(5-phenyl-1H-imidazol-2-yl)phenyl)-2-(2-cyanopropan-2-yl)isonicotinamide, 2-tert-butyl-N-(4-chloro-3-(5-phenyl-1H-imidazol-2-yl)phenyl) isonicotinamide, 4'-cyano-2-methyl-N-(6-thiomorpholinopyridin-3-yl)biphenyl-3-carboxamide, N-(4-chloro-3-(5-phenyl-1H-imidazol-2-yl)phenyl)-3-fluoroisonicotinamide, 2-bromo-N-(4-chloro-3-(5-phenyl-1H-imidazol-2-yl)phenyl)isonicotinamide, 3-bromo-N-(4-chloro-3-(5-phenyl-1H-imidazol-2-yl)phenyl)-2-fluorobenzamide, 2-chloro-N-(4-chloro-3-(5-phenyl-1H-imidazol-2-yl)phenyl)-3,4-dimethoxybenzamide, 3-chloro-N-(4-chloro-3-(5-phenyl1H-imidazol-2-yl)phenyl) isonicotinamide, N-(4-chloro-3-(5-phenyl-1H-imidazol-2-yl)phenyl)-2-methylisonicotinamide, 4-chloro-N-(4-chloro-3-(5-phenyl-1H-imidazol-2-yl)phenyl)nicotinamide, 2,5-dichloro-N-(4-chloro-3-(5-phenyl-1H-imidazol-2-yl) phenyl)isonicotinamide, N-(4-chloro-3-(5-phenyl-1H-imidazol-2-yl)phenyl)-2-(1H-tetrazol-1-yl)isonicotinamide, 4-bromo-N-(4-chloro-3-(5-phenyl-1H-imidazol-2-yl)phenyl)picolinamide, 2,6-dichloro-N-(4-chloro-3-(5-phenyl-1H-imidazol-2-yl)phenyl)isonicotinamide, N-(4-chloro-3-(5-phenyl-1H-imidazol-2-yl)phenyl)-4-methylnicotinamide, N-(4-chloro-3-(5-phenyl-1H-imidazol-2-yl)phenyl)-2-hydroxy-6-(trifluoromethyl)nicotinamide, 2-acetamido-N-(4-chloro-3-(5-phenyl-1H-imidazol-2-yl)phenyl)isonicotinamide, 3-bromo-N-(4-chloro-3-(5-phenyl-1H-imidazol-2-yl) phenyl)-2-methylbenzamide, 2-chloro-N-(4-chloro-3-(5-phenyl-1H-imidazol-2-yl)phenyl)-6-methylbenzamide, N-(4-chloro-3-(5-phenyl-1H-imidazol-2-yl)phenyl)-3-(trifluoromethyl)benzamide, N-(4-chloro-3-(4-phenyl-1H-imidazol-2-yl)phenyl)-3-(morpholinomethyl)pyridin-2-amine, N-(4-chloro-3-(5-phenyl-1H-imidazol-2-yl)phenyl)-6-hydroxypicolinamide, N-(4-chloro-3-(5-phenyl-1H-imidazol-2-yl)phenyl)-3-hydroxypicolinamide, 6-bromo-N-(4-chloro-3-(5-phenyl-1H-imidazol-2-yl)phenyl)picolinamide, N-(4-chloro-3-(5-phenyl-1H-imidazol-2-yl)phenyl)-6-methylpicolinamide, 5-butyl-N-(4-chloro-3-(5-phenyl-1H-imidazol-2-yl)phenyl)picolinamide, 4-chloro-N-(4-chloro-3-(5-phenyl-1H-imidazol-2-yl)phenyl)picolinamide, N-(4-chloro-3-(5-phenyl-1H-imidazol-2-yl)phenyl)-2,6-dimethoxynicotinamide, N-(4-chloro-3-(5-phenyl-1H-imidazol-2-yl)phenyl)-6-phenoxynicotinamide, N-(4-chloro-3-(5-phenyl-1H-imidazol-2-yl)phenyl)-2,6-dimethoxyisonicotinamide, 6-chloro-N-(4-chloro-3-(5-phenyl-1H-imidazol-2-yl)phenyl)picolinamide, N-(4-chloro-3-(5-phenyl-1H-imidazol-2-yl)phenyl)-2-fluoroisonicotinamide, N-(4-chloro-3-(5-phenyl-1H-imidazol-2-yl)phenyl)-6-ethoxynicotinamide, N-(4-chloro-3-(5-phenyl-1H-imidazol-2-yl)phenyl)-2-(2,2,2-trifluoroethoxy)isonicotinamide, N-(4-chloro-3-(5-phenyl-1H-imidazol-2-yl)phenyl)-6-isopropoxynicotinamide, N-(4-chloro-3-(5-phenyl-1H-imidazol-2-yl)phenyl)-6-propoxynicotinamide, 2,3-dichloro-N-(4-chloro-3-(5-phenyl-1H-imidazol-2-yl)phenyl)isonicotinamide, N-(4-chloro-3-(5-phenyl-1H-imidazol-2-yl)phenyl)-2-hydroxy-6-methylisonicotinamide, N-(4-chloro-3-(5-phenyl-1H-imidazol-2-yl)phenyl)-2-propoxyisonicotinamide, N-(4-chloro-3-(5-phenyl-1H-imidazol-2-yl)phenyl)-2-methyl-6-(trifluoromethyl)nicotinamide, 5-chloro-N-(4-chloro-3-(5-phenyl-1H-imidazol-2-yl)phenyl)-2-methoxyisonicotinamide, 3-chloro-N-(4-chloro-3-(5-phenyl-1H-imidazol-2-yl)phenyl)-2-methoxyisonicotinamide, 3,5-dichloro-N-(4-chloro-3-(5-phenyl-1H-imidazol-2-yl)phenyl)isonicotinamide, 2,6-dichloro-N-(4-chloro-3-(5-phenyl-1H-imidazol-2-yl) phenyl)nicotinamide, 2-chloro-N-(4-chloro-3-(5-phenyl-1H-imidazol-2-yl)phenyl)-4-(methylsulfonyl)benzamide, 2,3-dichloro-N-(4-chloro-3-(5-phenyl-1H-imidazol-2-yl) phenyl)benzamide, N-(4-chloro-3-(5-phenyl-1H-imidazol-2-yl)phenyl)-4-isopropoxy-2-methylbenzamide, N-(4-chloro-3-(5-phenyl-1H-imidazol-2-yl)phenyl)-3-isopropoxy-2-methylbenzamide, N-(4-chloro-3-(5-phenyl-1H-imidazol-2-yl)phenyl)-2-isopropoxyisonicotinamide, 2-chloro-N-(4-chloro-3-(5-phenyl-1H-imidazol-2-yl)phenyl)-6-methoxynicotinamide, 2-chloro-N-(4-chloro-3-(5-phenyl-1H-imidazol-2-yl)phenyl)-4-ethoxybenzamide, 2-chloro-N-(4-chloro-3-(5-phenyl-1H-imidazol-2-yl)phenyl)-4-isopropoxybenzamide, 2-chloro-N-(4-chloro-3-(5-phenyl-1H-imidazol-2-yl)phenyl)-6-isopropoxynicotinamide, -(4-chloro-3-(5-phenyl-1H-imidazol-2-yl)phenyl)-6-methoxy-2-methylnicotinamide, 2,3-dichloro-N-(4-chloro-3-(5-phenyl-1H-imidazol-2-yl)phenyl)-4-(ethylsulfonyl) benzamide, 2-((2S,6R)-2,6-dimethylmorpholino)-N-(4-methyl-3-(4-phenyl-1H-imidazol-2-yl)phenyl)thiazole-5-carboxamide, 2-chloro-N-(4-chloro-3-(5-phenyl-1H-imidazol-2-yl)phenyl)-4-(ethylsulfonyl)benzamide, 2-chloro-N-(4-chloro-3-(5-phenyl-1H-imidazol-2-yl)phenyl)-4-(isopropylsulfonyl)benzamide, 2-chloro-N-(4-chloro-3-(5-phenyl-1H-imidazol-2-yl)phenyl)-4-(propylsulfonyl)benzamide, and 2-chloro-N-(4-chloro-3-(5-phenyl-1H-imidazol-2-yl)phenyl)-4-(methylsulfonamido) benzamide.

* * * * *